US012392583B2

(12) United States Patent
Bridge et al.

(10) Patent No.: US 12,392,583 B2
(45) Date of Patent: Aug. 19, 2025

(54) BODY SAFETY DEVICE WITH VISUAL SENSING AND HAPTIC RESPONSE USING ARTIFICIAL INTELLIGENCE

(71) Applicants: John Bridge, Hillsborough, NC (US); Frank L. Hammond, III, Atlanta, GA (US); Patrick Gibbons, Columbia, MD (US); Goktug Duman, Miami, FL (US); Arthi Abhyanker, Mountain View, CA (US); Joe Lanzi, Grover, MO (US); Nelson So, Dawsonville, GA (US); Raj Abhyanker, Mountain View, CA (US); Cameron Christensen, Mountain View, CA (US)

(72) Inventors: John Bridge, Hillsborough, NC (US); Frank L. Hammond, III, Atlanta, GA (US); Patrick Gibbons, Columbia, MD (US); Goktug Duman, Miami, FL (US); Arthi Abhyanker, Mountain View, CA (US); Joe Lanzi, Grover, MO (US); Nelson So, Dawsonville, GA (US); Raj Abhyanker, Mountain View, CA (US); Cameron Christensen, Mountain View, CA (US)

( * ) Notice: Subject to any disclaimer, the term of this patent is extended or adjusted under 35 U.S.C. 154(b) by 0 days.

(21) Appl. No.: 18/596,684

(22) Filed: Mar. 6, 2024

(65) Prior Publication Data

US 2025/0207894 A1    Jun. 26, 2025

Related U.S. Application Data

(60) Provisional application No. 63/614,022, filed on Dec. 22, 2023, provisional application No. 63/616,817,
(Continued)

(51) Int. Cl.
*F41H 1/00* (2006.01)
*A61B 5/00* (2006.01)
(Continued)

(52) U.S. Cl.
CPC .............. *F41H 1/00* (2013.01); *A61B 5/6805* (2013.01); *A61B 5/747* (2013.01); *G06F 40/58* (2020.01); *G08B 6/00* (2013.01); *G08B 21/02* (2013.01)

(58) Field of Classification Search
CPC ........... F41H 1/00; G06F 40/58; A61B 5/747; G08B 6/00; G08B 21/02
(Continued)

(56) References Cited

U.S. PATENT DOCUMENTS

| 1,337,920 A | 4/1920 | Ernest |
| 4,008,456 A | 2/1977 | Ewart |

(Continued)

FOREIGN PATENT DOCUMENTS

| AU | 2012201637 B2 | 9/2013 |
| CA | 2903640 A1 | 3/2017 |

(Continued)

OTHER PUBLICATIONS

"IAP Software", by the Response Group, Published in [2003] https://www.responsegroupinc.com/lap.
(Continued)

*Primary Examiner* — Jack K Wang
(74) *Attorney, Agent, or Firm* — LEGALFORCE RAPC WORLDWIDE

(57) ABSTRACT

Disclosed are a method, system, and apparatus of s body safety device with visual sensing and haptic response using artificial intelligence. In one embodiment, a body worn safety device includes a visual sensor integrated into a tactical gear and a haptic feedback device integrated in the
(Continued)

tactical gear. The haptic feedback device vibrates when the visual sensor detects an ambient threat to a wearer of the tactical gear. The haptic feedback device may detect the ambient threat using an artificial intelligence based threat detection model. The visual sensor may be part of an array of visual sensors around a torso of the wearer such that ambient threats around the wearer are captured through the artificial intelligence based threat detection model. A battery unit may be detachable from the tactical gear.

30 Claims, 24 Drawing Sheets

Related U.S. Application Data filed on Jan. 1, 2024, provisional application No. 63/622,514, filed on Jan. 18, 2024, provisional application No. 63/626,075, filed on Jan. 29, 2024, provisional application No. 63/552,265, filed on Feb. 12, 2024, provisional application No. 63/555,014, filed on Feb. 17, 2024, provisional application No. 63/554,360, filed on Feb. 16, 2024.

(51) Int. Cl.
*G06F 40/58* (2020.01)
*G08B 6/00* (2006.01)
*G08B 21/02* (2006.01)

(58) Field of Classification Search
USPC ...................................................... 340/573.1
See application file for complete search history.

(56) References Cited

U.S. PATENT DOCUMENTS

| | | |
|---|---|---|
| 4,231,311 A | 11/1980 | Longerich |
| 4,358,984 A | 11/1982 | Winblad |
| 4,367,752 A | 1/1983 | Jimenez et al. |
| 5,005,213 A | 4/1991 | Hanson et al. |
| 5,219,290 A | 6/1993 | Lapp et al. |
| 5,416,903 A | 5/1995 | Malcolm |
| 5,594,498 A | 1/1997 | Fraley |
| 5,677,979 A | 10/1997 | Squicciarini et al. |
| 5,815,093 A | 9/1998 | Kikinis |
| 5,864,481 A | 1/1999 | Gross et al. |
| 5,942,716 A | 8/1999 | Miller |
| 6,029,558 A | 2/2000 | Stevens et al. |
| 6,128,999 A | 10/2000 | Sepp et al. |
| 6,198,394 B1 | 3/2001 | Jacobsen et al. |
| 6,215,498 B1 | 4/2001 | Filo et al. |
| 6,219,646 B1 | 4/2001 | Cherny |
| 6,349,201 B1 | 2/2002 | Ford |
| 6,388,422 B1 | 5/2002 | Lew |
| 6,481,782 B2 | 11/2002 | Bond |
| 6,513,003 B1 | 1/2003 | Angell et al. |
| 6,522,531 B1 | 2/2003 | Quintana et al. |
| 6,567,503 B2 | 5/2003 | Engelke et al. |
| 6,595,102 B2 | 7/2003 | Stevens et al. |
| 6,613,001 B1 | 9/2003 | Dworkin |
| 6,690,932 B1 | 2/2004 | Barnier et al. |
| 6,784,833 B1 | 8/2004 | Evans |
| 6,820,055 B2 | 11/2004 | Saindon et al. |
| 6,831,556 B1 | 12/2004 | Boykin |
| 6,980,953 B1 | 12/2005 | Kanevsky et al. |
| 7,035,804 B2 | 4/2006 | Saindon et al. |
| 7,046,214 B2 | 5/2006 | Ebersole, Jr. et al. |
| 7,058,710 B2 | 6/2006 | McCall et al. |
| 7,091,852 B2 | 8/2006 | Mason et al. |
| 7,132,928 B2 | 11/2006 | Perricone |
| 7,173,437 B2 | 2/2007 | Hervieux et al. |
| 7,245,216 B2 | 7/2007 | Burkley et al. |
| 7,342,648 B2 | 3/2008 | Solomon et al. |
| 7,389,221 B1 | 6/2008 | Pearson et al. |
| 7,456,875 B2 | 11/2008 | Kashiwa |
| 7,538,666 B2 | 5/2009 | Campman |
| 7,539,086 B2 | 5/2009 | Jaroker |
| 7,570,301 B2 | 8/2009 | Gilor |
| 7,696,919 B2 | 4/2010 | Moraites |
| 7,719,428 B2 | 5/2010 | Fisher et al. |
| 7,747,434 B2 | 6/2010 | Flanagan et al. |
| 7,768,548 B2 | 8/2010 | Silvernail et al. |
| 7,827,900 B2 | 11/2010 | Beach et al. |
| 7,845,018 B1 | 12/2010 | Greer |
| 7,898,410 B2 | 3/2011 | Schurter |
| 7,900,548 B2 | 3/2011 | Hoadley et al. |
| 7,930,181 B1 | 4/2011 | Goffin et al. |
| 7,996,465 B2 | 8/2011 | Cromp et al. |
| 7,999,741 B2 | 8/2011 | Graves et al. |
| 8,018,320 B2 | 9/2011 | Struijk |
| 8,051,762 B2 | 11/2011 | Beach et al. |
| 8,078,551 B2 | 12/2011 | Bar |
| 8,141,470 B1 | 3/2012 | Farinella et al. |
| 8,154,844 B2 | 4/2012 | Brown |
| 8,205,537 B1 | 6/2012 | Dupont |
| 8,239,207 B2 | 8/2012 | Seligman et al. |
| 8,242,880 B2 | 8/2012 | Ghovanloo et al. |
| 8,274,377 B2 | 9/2012 | Smith et al. |
| 8,281,702 B2 | 10/2012 | Hoadley et al. |
| 8,316,753 B2 | 11/2012 | Beach et al. |
| 8,362,945 B2 | 1/2013 | Wootan et al. |
| 8,370,142 B2 | 2/2013 | Frankel et al. |
| 8,386,233 B2 | 2/2013 | Khuda |
| 8,464,949 B2 | 6/2013 | Namey et al. |
| 8,487,755 B2 | 7/2013 | Gudgel et al. |
| 8,526,934 B2 | 9/2013 | Sennett et al. |
| 8,593,286 B2 | 11/2013 | Razoumov et al. |
| 8,599,010 B2 | 12/2013 | Bose et al. |
| 8,639,396 B1 | 1/2014 | Hirsch et al. |
| 8,674,806 B1 | 3/2014 | Malik et al. |
| 8,676,234 B2 | 3/2014 | Conner et al. |
| 8,698,634 B2 | 4/2014 | Guedes Lopes Da Fonseca et al. |
| 8,755,839 B2 | 6/2014 | Parkulo et al. |
| 8,776,662 B1 | 7/2014 | Hoenes |
| 8,791,836 B2 | 7/2014 | Herman |
| 8,812,096 B2 | 8/2014 | Flaherty et al. |
| 8,838,459 B2 | 9/2014 | Uszkoreit et al. |
| 8,853,891 B2 | 10/2014 | Soar |
| 8,857,309 B2 | 10/2014 | Wentzel |
| 8,872,655 B2 | 10/2014 | Buller et al. |
| 8,896,696 B2 | 11/2014 | Ellsworth et al. |
| 8,945,328 B2 | 2/2015 | Longinotti-Buitoni et al. |
| 8,949,289 B2 | 2/2015 | Lasensky et al. |
| 8,965,129 B2 | 2/2015 | Rogowski et al. |
| 9,042,971 B2 | 5/2015 | Brumback et al. |
| 9,063,931 B2 | 6/2015 | Wu |
| 9,076,448 B2 | 7/2015 | Bennett et al. |
| 9,085,362 B1 | 7/2015 | Kilian et al. |
| 9,195,652 B2 | 11/2015 | Custer et al. |
| 9,229,535 B2 | 1/2016 | Vice et al. |
| 9,245,278 B2 | 1/2016 | Orsini et al. |
| 9,246,898 B2 | 1/2016 | McKeeman et al. |
| 9,282,893 B2 | 3/2016 | Aliverti et al. |
| 9,338,622 B2 | 5/2016 | Bjontegard |
| 9,342,976 B2 | 5/2016 | Pfeffer |
| 9,354,703 B2 | 5/2016 | Maggiali et al. |
| 9,466,187 B2 | 10/2016 | Grant et al. |
| 9,501,472 B2 | 11/2016 | Manuselis et al. |
| 9,507,772 B2 | 11/2016 | Parkinson et al. |
| 9,560,324 B2 | 1/2017 | Monaghan, Sr. et al. |
| 9,569,431 B2 | 2/2017 | Uszkoreit et al. |
| 9,582,035 B2 | 2/2017 | Connor |
| 9,589,448 B1 | 3/2017 | Schneider et al. |
| 9,602,993 B2 | 3/2017 | Vilrokx et al. |
| 9,614,969 B2 | 4/2017 | Aue et al. |
| 9,619,996 B1 | 4/2017 | Smith |
| 9,695,981 B2 | 7/2017 | Au et al. |
| 9,697,720 B1 | 7/2017 | Lassiter |
| 9,704,209 B2 | 7/2017 | Proud et al. |
| 9,710,819 B2 | 7/2017 | Cloran et al. |
| 9,712,730 B2 | 7/2017 | Phillips et al. |
| 9,720,737 B2 | 8/2017 | Ashtiani et al. |

(56) References Cited

U.S. PATENT DOCUMENTS

| | | |
|---|---|---|
| 9,734,820 B2 | 8/2017 | Rangarajan Sridhar et al. |
| 9,737,261 B2 | 8/2017 | Coza et al. |
| 9,740,686 B2 | 8/2017 | Johansson |
| 9,741,215 B2 | 8/2017 | Brav et al. |
| 9,804,946 B2 | 10/2017 | Conlon et al. |
| 9,805,273 B1 | 10/2017 | Seeber et al. |
| 9,826,557 B2 | 11/2017 | Smith |
| 9,881,477 B2 | 1/2018 | Hyde et al. |
| 9,886,833 B2 | 2/2018 | Noland et al. |
| 9,922,518 B2 | 3/2018 | Hannigan et al. |
| 9,922,537 B2 | 3/2018 | Shah et al. |
| 9,980,102 B2 | 5/2018 | Bohlander et al. |
| 9,996,168 B2 | 6/2018 | Menon et al. |
| 10,013,858 B2 | 7/2018 | Zerick et al. |
| 10,020,909 B2 | 7/2018 | Stamm et al. |
| 10,021,672 B2 | 7/2018 | Cole et al. |
| 10,025,991 B2 | 7/2018 | Seeber et al. |
| 10,025,993 B2 | 7/2018 | Seeber et al. |
| 10,043,033 B1 | 8/2018 | Hadsall |
| 10,043,354 B2 | 8/2018 | Man et al. |
| 10,070,260 B1 | 9/2018 | Miyazawa et al. |
| 10,084,500 B2 | 9/2018 | Davis et al. |
| 10,102,732 B2 | 10/2018 | Gersten |
| 10,103,835 B2 | 10/2018 | Morrow et al. |
| 10,105,101 B2 | 10/2018 | Fougere et al. |
| 10,108,306 B2 | 10/2018 | Khoo et al. |
| 10,129,704 B1 | 11/2018 | Huseth et al. |
| 10,137,363 B2 | 11/2018 | Parshionikar |
| 10,154,391 B2 | 12/2018 | Yoakum et al. |
| 10,178,973 B2 | 1/2019 | Venkatraman et al. |
| 10,204,520 B2 | 2/2019 | Demetriades et al. |
| 10,209,365 B2 | 2/2019 | Venkatraman et al. |
| 10,229,329 B2 | 3/2019 | Seeber et al. |
| 10,230,919 B2 | 3/2019 | Davis et al. |
| 10,234,938 B2 | 3/2019 | Moffat et al. |
| 10,237,012 B2 | 3/2019 | Morrow et al. |
| 10,257,434 B2 | 4/2019 | Arnold |
| 10,258,534 B1 | 4/2019 | Sills et al. |
| 10,271,591 B2 | 4/2019 | Bangera et al. |
| 10,306,094 B2 | 5/2019 | Miklautsch et al. |
| 10,317,506 B2 | 6/2019 | Seeber et al. |
| 10,327,674 B2 | 6/2019 | Hong et al. |
| 10,349,227 B2 | 7/2019 | Saxena et al. |
| 10,351,237 B2 | 7/2019 | Baruch |
| 10,370,102 B2 | 8/2019 | Boykin et al. |
| 10,370,122 B2 | 8/2019 | Fisher et al. |
| 10,455,187 B2 | 10/2019 | Callis, Jr. et al. |
| 10,539,787 B2 | 1/2020 | Haddick et al. |
| 10,542,222 B2 | 1/2020 | Arnold |
| 10,542,929 B2 | 1/2020 | Kimmel |
| 10,560,668 B2 | 2/2020 | Araya et al. |
| 10,567,107 B2 | 2/2020 | Morrow et al. |
| 10,573,164 B2 | 2/2020 | Singh et al. |
| 10,574,384 B2 | 2/2020 | Morrow et al. |
| 10,599,106 B2 | 3/2020 | Zeier |
| 10,599,929 B2 | 3/2020 | Cuban et al. |
| 10,600,295 B2 | 3/2020 | Asher et al. |
| 10,600,417 B2 | 3/2020 | Tormasov et al. |
| 10,613,248 B2 | 4/2020 | Benke et al. |
| 10,614,171 B2 | 4/2020 | Orsini et al. |
| 10,621,443 B2 | 4/2020 | Seeber et al. |
| 10,653,202 B2 | 5/2020 | Destrian et al. |
| 10,657,362 B2 | 5/2020 | Ranganath et al. |
| 10,668,356 B2 | 6/2020 | Bangera et al. |
| 10,701,520 B2 | 6/2020 | Singh et al. |
| 10,805,576 B2 | 10/2020 | Hanchett et al. |
| 10,812,755 B2 | 10/2020 | Davis et al. |
| 10,814,894 B2 | 10/2020 | Preston et al. |
| 10,854,098 B1 | 12/2020 | Welch et al. |
| 10,861,308 B1 | 12/2020 | Simpson et al. |
| 10,861,317 B2 | 12/2020 | Wengrovitz et al. |
| 10,861,320 B2 | 12/2020 | Martin et al. |
| 10,866,597 B1 | 12/2020 | Reinhold et al. |
| 10,896,598 B1 | 1/2021 | Boss et al. |
| 10,901,373 B2 | 1/2021 | Locke et al. |
| 10,970,934 B2 | 4/2021 | Rogers et al. |
| 10,977,452 B2 | 4/2021 | Wang et al. |
| 11,025,723 B2 | 6/2021 | Fortna et al. |
| 11,032,515 B2 | 6/2021 | Mazzarella et al. |
| 11,057,584 B2 | 7/2021 | Davis et al. |
| 11,062,584 B1 | 7/2021 | Magaletta |
| 11,076,134 B2 | 7/2021 | Govezensky et al. |
| 11,087,613 B2 | 8/2021 | Barber |
| 11,096,590 B2 | 8/2021 | Tang et al. |
| 11,122,237 B2 | 9/2021 | Nguyen et al. |
| 11,126,204 B2 | 9/2021 | Abramov et al. |
| 11,158,343 B2 | 10/2021 | Hershfield et al. |
| 11,160,504 B2 | 11/2021 | Yun et al. |
| 11,170,782 B2 | 11/2021 | Stoker et al. |
| 11,188,854 B2 | 11/2021 | Dimino et al. |
| 11,197,773 B2 | 12/2021 | Sakuma et al. |
| 11,216,954 B2 | 1/2022 | Peled et al. |
| 11,232,702 B2 | 1/2022 | Huseth et al. |
| 11,272,779 B2 | 3/2022 | Grinnell |
| 11,288,973 B2 | 3/2022 | Vacek |
| 11,297,164 B2 | 4/2022 | McCormack et al. |
| 11,304,778 B2 | 4/2022 | Shanjani et al. |
| 11,308,792 B2 | 4/2022 | Rao |
| 11,315,396 B2 | 4/2022 | Kaindl |
| 11,375,161 B2 | 6/2022 | Shimada et al. |
| 11,385,022 B2 | 7/2022 | Hatcher et al. |
| 11,388,546 B2 | 7/2022 | Williams |
| 11,425,653 B2 | 8/2022 | Hanchett et al. |
| 11,436,900 B2 | 9/2022 | Baron et al. |
| 11,521,128 B2 | 12/2022 | Moro et al. |
| 11,521,285 B2 | 12/2022 | Schuler et al. |
| 11,622,138 B2 | 4/2023 | MacDonald |
| 11,632,539 B2 | 4/2023 | Smith et al. |
| 11,645,904 B2 | 5/2023 | Trundle et al. |
| 11,706,391 B1 | 7/2023 | Heywood et al. |
| 11,717,185 B2 | 8/2023 | Cusey et al. |
| 11,741,820 B1 | 8/2023 | Bacco et al. |
| 11,749,074 B2 | 9/2023 | Attariani et al. |
| 11,790,741 B2 | 10/2023 | Williams |
| 11,819,324 B2 | 11/2023 | Cusey et al. |
| 11,877,614 B2 | 1/2024 | Berzowska et al. |
| 11,879,705 B2 | 1/2024 | Taveniku |
| 11,893,101 B2 | 2/2024 | Haraguchi et al. |
| 11,900,915 B2 | 2/2024 | Chen et al. |
| 11,902,871 B2 | 2/2024 | Pellegrini et al. |
| 11,920,901 B2 | 3/2024 | Basche et al. |
| 11,942,093 B2 | 3/2024 | Dubinsky et al. |
| 2001/0029455 A1 | 10/2001 | Chin et al. |
| 2002/0026431 A1 | 2/2002 | Pedersen et al. |
| 2002/0145849 A1 | 10/2002 | Peterson |
| 2002/0149510 A1 | 10/2002 | Salzeder |
| 2002/0196202 A1 | 12/2002 | Bastian et al. |
| 2003/0065503 A1 | 4/2003 | Agnihotri et al. |
| 2003/0115059 A1 | 6/2003 | Jayaratne |
| 2003/0125998 A1 | 7/2003 | McKenney et al. |
| 2004/0219491 A1 | 11/2004 | Shlomo |
| 2005/0054940 A1 | 3/2005 | Almen |
| 2005/0264412 A1 | 12/2005 | Levesque et al. |
| 2006/0028556 A1 | 2/2006 | Bunn et al. |
| 2006/0077253 A1 | 4/2006 | VanRiper et al. |
| 2006/0107829 A1 | 5/2006 | Shumov et al. |
| 2006/0190250 A1 | 8/2006 | Saindon et al. |
| 2006/0211404 A1 | 9/2006 | Cromp et al. |
| 2006/0225566 A1 | 10/2006 | Lloyd |
| 2007/0213088 A1 | 9/2007 | Sink |
| 2007/0229356 A1 | 10/2007 | Kodrin |
| 2007/0268368 A1 | 11/2007 | Bradford |
| 2008/0001764 A1 | 1/2008 | Douglas et al. |
| 2008/0114220 A1 | 5/2008 | Banet et al. |
| 2008/0133299 A1 | 6/2008 | Sitarski |
| 2008/0165047 A1 | 7/2008 | Fisher et al. |
| 2008/0219100 A1 | 9/2008 | Fisher et al. |
| 2008/0258063 A1 | 10/2008 | Rapanotti |
| 2008/0291075 A1 | 11/2008 | Rapanotti |
| 2009/0031467 A1 | 2/2009 | Swindells et al. |
| 2009/0055347 A1 | 2/2009 | Hollman et al. |
| 2009/0174547 A1 | 7/2009 | Greene et al. |
| 2009/0257603 A1 | 10/2009 | Chan et al. |
| 2009/0311928 A1 | 12/2009 | McClintock et al. |

(56) References Cited

U.S. PATENT DOCUMENTS

| | | |
|---|---|---|
| 2010/0057435 A1 | 3/2010 | Kent et al. |
| 2010/0246328 A1 | 9/2010 | Gudgel et al. |
| 2010/0315228 A1 | 12/2010 | Grilliot et al. |
| 2010/0319524 A1 | 12/2010 | Farinella et al. |
| 2011/0077933 A1 | 3/2011 | Miyamoto et al. |
| 2011/0113952 A1 | 5/2011 | Rosenwasser et al. |
| 2011/0187524 A1 | 8/2011 | Cochran, III |
| 2011/0279270 A1 | 11/2011 | Marckwald et al. |
| 2012/0011994 A1 | 1/2012 | Hoadley et al. |
| 2012/0126960 A1 | 5/2012 | Steger et al. |
| 2012/0174299 A1 | 7/2012 | Balzano |
| 2012/0198593 A1 | 8/2012 | Beck et al. |
| 2012/0259554 A1 | 10/2012 | Chen et al. |
| 2012/0271121 A1 | 10/2012 | Della Torre et al. |
| 2012/0275272 A1 | 11/2012 | Mullen et al. |
| 2012/0286933 A1 | 11/2012 | Hsiao |
| 2012/0299751 A1 | 11/2012 | Verna et al. |
| 2012/0299826 A1 | 11/2012 | Moeller |
| 2012/0330643 A1 | 12/2012 | Frei et al. |
| 2013/0057693 A1 | 3/2013 | Baranek |
| 2013/0090931 A1 | 4/2013 | Ghovanloo et al. |
| 2013/0200118 A1 | 8/2013 | Johnson |
| 2013/0300535 A1 | 11/2013 | Gorman |
| 2014/0030982 A1 | 1/2014 | Cardona |
| 2014/0081091 A1 | 3/2014 | Abolfathi et al. |
| 2014/0102288 A1 | 4/2014 | Yeshurun et al. |
| 2014/0118554 A1 | 5/2014 | Bucknor |
| 2014/0135593 A1 | 5/2014 | Jayalth et al. |
| 2014/0266705 A1 | 9/2014 | McKinley et al. |
| 2014/0349597 A1 | 11/2014 | Abolfathi et al. |
| 2014/0358516 A1 | 12/2014 | Lin et al. |
| 2014/0368814 A1 | 12/2014 | Krupkin et al. |
| 2015/0172520 A1 | 6/2015 | Lindman et al. |
| 2015/0189133 A1 | 7/2015 | Sandy |
| 2015/0241153 A1 | 8/2015 | Mardirossian |
| 2015/0290453 A1 | 10/2015 | Tyler et al. |
| 2015/0301619 A1 | 10/2015 | Menon |
| 2015/0346840 A1 | 12/2015 | Alonaizi |
| 2016/0000548 A1 | 1/2016 | Aiden et al. |
| 2016/0038083 A1 | 2/2016 | Ding et al. |
| 2016/0073025 A1 | 3/2016 | Cilia |
| 2016/0078020 A1 | 3/2016 | Sumita et al. |
| 2016/0088498 A1 | 3/2016 | Sharawi |
| 2016/0117940 A1 | 4/2016 | Gomory et al. |
| 2016/0125705 A1 | 5/2016 | Hurtig et al. |
| 2016/0154468 A1 | 6/2016 | Kimmel |
| 2016/0178326 A1 | 6/2016 | Strauss et al. |
| 2016/0182850 A1 | 6/2016 | Thompson |
| 2016/0310022 A1 | 10/2016 | Stivoric et al. |
| 2016/0360146 A1 | 12/2016 | Smith |
| 2016/0367188 A1 | 12/2016 | Malik et al. |
| 2017/0061784 A1 | 3/2017 | Clough |
| 2017/0092138 A1 | 3/2017 | Trundle et al. |
| 2017/0102460 A1 | 4/2017 | Harris |
| 2017/0116874 A1* | 4/2017 | Holcomb ............... G09B 9/003 |
| 2017/0127257 A1 | 5/2017 | Saxena et al. |
| 2017/0135633 A1 | 5/2017 | Connor |
| 2017/0154521 A1 | 6/2017 | Zamorano-Larrate |
| 2017/0163956 A1 | 6/2017 | Lorenzetti |
| 2017/0187876 A1 | 6/2017 | Hayes et al. |
| 2017/0193308 A1 | 7/2017 | Buyse et al. |
| 2017/0238129 A1 | 8/2017 | Maier et al. |
| 2017/0253330 A1 | 9/2017 | Saigh et al. |
| 2017/0272707 A1 | 9/2017 | Davis et al. |
| 2017/0277700 A1 | 9/2017 | Davis et al. |
| 2017/0337791 A1 | 11/2017 | Gordon-Carroll |
| 2017/0339741 A1 | 11/2017 | K et al. |
| 2017/0364349 A1 | 12/2017 | Conant et al. |
| 2018/0047387 A1 | 2/2018 | Nir |
| 2018/0050800 A1 | 2/2018 | Boykin et al. |
| 2018/0059660 A1 | 3/2018 | Heatzig et al. |
| 2018/0122205 A1* | 5/2018 | Mujeeb ............... G08B 5/006 |
| 2018/0233019 A1 | 8/2018 | Werronen et al. |
| 2018/0249133 A1* | 8/2018 | Thiel ............... H01M 50/242 |
| 2018/0292542 A1 | 10/2018 | Anand |
| 2018/0300008 A1 | 10/2018 | Rasanen |
| 2018/0325187 A1 | 11/2018 | Coalson, Jr. |
| 2018/0327091 A1 | 11/2018 | Burks et al. |
| 2018/0341262 A1 | 11/2018 | Yeshurun |
| 2018/0367237 A1 | 12/2018 | Morrow et al. |
| 2019/0004596 A1 | 1/2019 | Henrique Barbosa Postcard et al. |
| 2019/0037166 A1* | 1/2019 | Davis ............... A41D 1/06 |
| 2019/0037934 A1 | 2/2019 | Swank et al. |
| 2019/0041975 A1 | 2/2019 | Anderson et al. |
| 2019/0122516 A1 | 4/2019 | Lorenzetti et al. |
| 2019/0130913 A1 | 5/2019 | Li |
| 2019/0248391 A1 | 8/2019 | Preston et al. |
| 2019/0283247 A1 | 9/2019 | Chang et al. |
| 2019/0302894 A1 | 10/2019 | Alvarado et al. |
| 2019/0369939 A1 | 12/2019 | Levesque et al. |
| 2020/0020356 A1 | 1/2020 | Smith et al. |
| 2020/0106818 A1 | 4/2020 | Luong |
| 2020/0225684 A1 | 7/2020 | Anderson et al. |
| 2020/0229739 A1 | 7/2020 | Reddy |
| 2020/0288089 A1 | 9/2020 | Thiel et al. |
| 2020/0371227 A1 | 11/2020 | Malhi |
| 2020/0375528 A1 | 12/2020 | Flanagan |
| 2020/0380959 A1 | 12/2020 | Chen |
| 2021/0071972 A1 | 3/2021 | Deng et al. |
| 2021/0085247 A1 | 3/2021 | Meirav |
| 2021/0137382 A1 | 5/2021 | Koster |
| 2021/0145450 A1 | 5/2021 | Gruentzig |
| 2021/0148679 A1 | 5/2021 | Basche et al. |
| 2021/0152788 A1 | 5/2021 | Ross |
| 2021/0192918 A1 | 6/2021 | Samadani et al. |
| 2021/0256246 A1 | 8/2021 | Dagdeviren et al. |
| 2021/0312143 A1 | 10/2021 | Trehan |
| 2021/0326563 A1 | 10/2021 | Kossor |
| 2021/0345118 A1 | 11/2021 | Guzik |
| 2021/0346738 A1 | 11/2021 | Howland |
| 2021/0364256 A1 | 11/2021 | Piro et al. |
| 2021/0401075 A1 | 12/2021 | Gruentzig |
| 2022/0004251 A1 | 1/2022 | Vega Gálvez et al. |
| 2022/0067394 A1 | 3/2022 | Suksi et al. |
| 2022/0096207 A1 | 3/2022 | Shanjani et al. |
| 2022/0148320 A1 | 5/2022 | Alakarhu et al. |
| 2022/0163658 A1* | 5/2022 | Yoshioka ............... G01S 7/411 |
| 2022/0172585 A1 | 6/2022 | Wedig et al. |
| 2022/0198597 A1 | 6/2022 | Hanchett et al. |
| 2022/0223247 A1 | 7/2022 | Davidson et al. |
| 2022/0231873 A1 | 7/2022 | Werfelli et al. |
| 2022/0270610 A1 | 8/2022 | Spitzer-Williams et al. |
| 2022/0288390 A1 | 9/2022 | Papay et al. |
| 2022/0300719 A1 | 9/2022 | Raina |
| 2022/0303449 A1 | 9/2022 | Bohlander et al. |
| 2022/0311979 A1 | 9/2022 | Wexler et al. |
| 2022/0353478 A1 | 11/2022 | Alakarhu et al. |
| 2022/0364829 A1 | 11/2022 | Wallack et al. |
| 2023/0009588 A1 | 1/2023 | Alphonse et al. |
| 2023/0021300 A9 | 1/2023 | Rathnam et al. |
| 2023/0049184 A1 | 2/2023 | Alakarhu |
| 2023/0073359 A1 | 3/2023 | Kukuk |
| 2023/0073517 A1 | 3/2023 | Jones et al. |
| 2023/0074279 A1 | 3/2023 | Spitzer-Williams et al. |
| 2023/0097676 A1 | 3/2023 | Liew et al. |
| 2023/0102363 A1 | 3/2023 | Mehring |
| 2023/0104514 A1* | 4/2023 | Chen ............... A63F 13/92 340/691.5 |
| 2023/0149143 A1 | 5/2023 | Shanjani et al. |
| 2023/0157564 A1 | 5/2023 | Zuckerman-Stark et al. |
| 2023/0169881 A1 | 6/2023 | Evans et al. |
| 2023/0188243 A1 | 6/2023 | Reynolds et al. |
| 2023/0209156 A1 | 6/2023 | Lambert et al. |
| 2023/0209440 A1 | 6/2023 | Frusina et al. |
| 2023/0223038 A1 | 7/2023 | Shastry et al. |
| 2023/0252647 A1* | 8/2023 | Nakazato ............... H04N 7/18 382/103 |
| 2023/0260070 A1 | 8/2023 | Smith et al. |
| 2023/0262426 A1 | 8/2023 | Bohlander et al. |
| 2023/0280125 A1 | 9/2023 | Prodzenko |
| 2023/0284004 A1 | 9/2023 | Pellegrini et al. |
| 2023/0300591 A1 | 9/2023 | Hamre et al. |
| 2023/0316897 A1* | 10/2023 | Koga ............... G08G 1/005 340/944 |

(56) References Cited

U.S. PATENT DOCUMENTS

| | | | |
|---|---|---|---|
| 2023/0336958 A1 | 10/2023 | Mehta et al. | |
| 2023/0349667 A1 | 11/2023 | Wagner et al. | |
| 2023/0386212 A1* | 11/2023 | Singh | G06V 40/174 |
| 2023/0388416 A1 | 11/2023 | Srivastava et al. | |
| 2023/0400551 A1 | 12/2023 | Parker et al. | |
| 2023/0417919 A1 | 12/2023 | Goldstein et al. | |
| 2024/0031522 A1 | 1/2024 | Davis et al. | |
| 2024/0046952 A1 | 2/2024 | Davis et al. | |
| 2024/0048673 A1 | 2/2024 | Thiel | |
| 2024/0053819 A1 | 2/2024 | Browy | |
| 2024/0099934 A1 | 3/2024 | Kozin et al. | |
| 2024/0191958 A1* | 6/2024 | Asbach | F41C 23/16 |

FOREIGN PATENT DOCUMENTS

| | | |
|---|---|---|
| CA | 2997443 C | 2/2021 |
| CN | 100577095 C | 1/2010 |
| CN | 101849713 A | 10/2010 |
| CN | 102120070 A | 7/2011 |
| CN | 102783193 A | 11/2012 |
| CN | 102903361 A | 1/2013 |
| CN | 103576691 A | 2/2014 |
| CN | 104635243 A | 5/2015 |
| CN | 104207761 B | 5/2016 |
| CN | 106127123 A | 11/2016 |
| CN | 206026321 U | 3/2017 |
| CN | 106652625 A | 5/2017 |
| CN | 103533129 B | 6/2017 |
| CN | 207039772 U | 2/2018 |
| CN | 105741514 B | 3/2018 |
| CN | 108806356 A | 11/2018 |
| CN | 105632049 A | 6/2019 |
| CN | 110177334 A | 8/2019 |
| CN | 111199668 A | 5/2020 |
| CN | 112419661 A | 2/2021 |
| CN | 213238622 U | 5/2021 |
| CN | 214906815 U | 11/2021 |
| CN | 114580980 A | 6/2022 |
| CN | 111124125 B | 6/2023 |
| CN | 116308944 B | 9/2023 |
| CN | 116943088 A | 10/2023 |
| DE | 102015003323 B4 | 2/2020 |
| EP | 3789966 A1 | 3/2021 |
| ES | 2343398 B1 | 6/2011 |
| IT | 202100017246 A1 | 12/2022 |
| JP | 2002230238 A | 8/2002 |
| JP | 2008529354 A | 7/2008 |
| JP | 2013171476 A | 9/2013 |
| JP | 2016131604 A | 7/2016 |
| JP | 2021027408 A | 2/2021 |
| JP | 7369507 B2 | 10/2023 |
| KR | 200453024 Y1 | 3/2011 |
| KR | 101197435 B1 | 11/2012 |
| KR | 101245165 B1 | 3/2013 |
| KR | 101440362 B1 | 9/2014 |
| KR | 101480302 B1 | 1/2015 |
| KR | 101613022 B1 | 4/2016 |
| KR | 20200104759 A | 9/2020 |
| KR | 102298763 B1 | 9/2021 |
| KR | 102442179 B1 | 9/2022 |
| KR | 102495287 B1 | 2/2023 |
| KR | 20230128744 A | 9/2023 |
| TW | 201545132 A | 12/2015 |
| TW | 1825793 B | 12/2023 |
| WO | 2001035044 A1 | 5/2001 |
| WO | 2006090371 A2 | 8/2006 |
| WO | 2008018947 A2 | 2/2008 |
| WO | 2011092553 A1 | 8/2011 |
| WO | 2011119673 A2 | 9/2011 |
| WO | 2012075292 A2 | 6/2012 |
| WO | 2012079791 A1 | 6/2012 |
| WO | 2014176485 A1 | 10/2014 |
| WO | 2014197463 A2 | 12/2014 |
| WO | 2015019360 A1 | 2/2015 |
| WO | 2015034149 A1 | 3/2015 |
| WO | 2016069052 A1 | 5/2016 |
| WO | 2017053693 A1 | 3/2017 |
| WO | 2018190748 A1 | 10/2018 |
| WO | 2018195704 A1 | 11/2018 |
| WO | 2020036643 A2 | 2/2020 |
| WO | 2020069512 A1 | 4/2020 |
| WO | 2020112245 A2 | 6/2020 |
| WO | 2020256906 A1 | 12/2020 |
| WO | 2021064490 A1 | 4/2021 |
| WO | 2022251371 A2 | 12/2022 |
| WO | 2022256698 A1 | 12/2022 |
| WO | 2023043965 A1 | 3/2023 |
| WO | 2023086851 A1 | 5/2023 |
| WO | 2023247811 A1 | 12/2023 |

OTHER PUBLICATIONS

"Next-Generation Incident Command System (NICS)", by Kontur, Found Online on [Mar. 12, 2024] https://www.kontur.io/portfolio/nics/.

"Next-Generation Incident Command System", by MIT Lincoln Laboratory, Found Online on [Mar. 12, 2024] https://www.ll.mit.edu/r-d/projects/next-generation-incident-command-system.

"Next-Generation Incident Command System Fact Sheet", by U.S. Department of Homeland Security, Published Online on [Jun. 5, 2024] https://www.dhs.gov/sites/default/files/publications/Next%20Generation%20Incident%20Command%20System-NICS_0.pdf.

"Response Tools", by NJ Resources, Found Online on [Mar. 12, 2024] https://njr.net/response-tools/.

"Axon Body 4", by Patrick W. Smith et al., Published In [1993] https://www.axon.com/products/axon-body-4.

"Digital Evidence Management, In-Car Video, and Advanced Body Cameras.", by Utility, Found Online on [Mar. 12, 2024] https://www.utility.com/.

"DisasterTech", by Roger Coleman et al., Published in [2019] https://www.disastertech.com/.

"Using Unmanned Aerial Vehicles (UAVs) as Mobile Sensing Platforms (MSPs) for Disaster Response, Civil Security and Public Safety", Published at Fundamental and Applied Research in Unmanned Aircraft Systems Technology, by Hanno Hildmann et al, Published Online on [Jul. 29, 2019] https://www.mdpi.com/2504-446X/3/3/59.

"Toward UAV-Based Airborne Computing", Published at IEEE Wireless Communications, by Kejie Lu et al., Published Online on [Aug. 5, 2019] https://par.nsf.gov/servlets/purl/10110848.

"Unmanned Aerial Vehicles for Wildland Fires: Sensing, Perception, Cooperation and Assistance", Published at Feature Papers of Drones, by Moulay A. Akhloufi et al., Published Online on [Feb. 22, 2021] https://www.mdpi.com/2504-446X/5/1/15.

"UAV-Enabled Disaster Management: Applications, Open Issues, and Challenges", Published at Journal of Field Robotics, by Amina Khan et al., Published Online on [Nov. 15, 2022] https://gmsarnjournal.com/home/wp-content/uploads/2023/06/vol18no1-6.pdf.

"Drone Swarms in Fire Suppression Activities: A Conceptual Framework", Published at UAV Application for Wildfire Detection, Prevention and Management, by Elena Ausonio et al., Published Online on [Mar. 7, 2021] https://www.mdpi.com/2504-446X/5/1/17.

"An Exploratory Study of the Use of Drones for Assisting Firefighters During Emergency Situations", Published at Conference on Human Factors in Computing Systems Proceedings, by Md. Nafiz Hasan Khan et al., Published Online on [May 2, 2019] http://clab.iat.sfu.ca/pubs/Khan-DronesFirefighters-CHI2019.pdf.

"The Good, the Bad and the Indispensable—Insights into the Practical Potential of Emergency Response Information Systems and Drones for Firefighters", Published at Hawaii International Conference on System Sciences, by Julian Weidinger, Published Online in [2018] https://core.ac.uk/download/pdf/143480849.pdf.

"Autonomous First Response Drone-Based Smart Rescue System for Critical Situation Management in Future Wireless Networks", Published at Journal on Innovative Communication Technologies, by Joel P. Lemayian et al., Published Online on [May 23, 2020] https://assets.pubpub.org/ybmy2nbl/71604609477880.pdf.

(56) References Cited

OTHER PUBLICATIONS

"Tactile Feedback in Defence & Security: The Next Frontier", by Haptic, Published Online on [May 13, 2023] https://www.haptic.ro/tactile-feedback-in-defence-security-the-next-frontier/.

"Wearable Technologies for Law Enforcement", Published at National Istitute of Justice, by Richard Silberglitt et al., Published Online on [Sep. 8, 2017] https://www.rand.org/content/dam/rand/pubs/research_reports/RR2000/RR2012/RAND_RR2012.pdf.

"IoT based Smart Vest and Helmet for Defence Sector", Published at IEEE International Conference on Communication Information and Computing Technology, by Ninad V. Joshi, Published Online on [Jun. 25, 2021] https://shorturl.at/inKQ8.

Utilizing Glove-Based Gestures and a Tactile Vest Display for Covert Communications and Robot Control, Published at Army Research Laboratory, by Linda R. Elliott et al., Published Online in [2014] https://apps.dtic.mil/sti/pdfs/ADA607637.pdf.

"Wearable Technologies Can Help Soldiers Survive in Adverse Environment", Published at Chakraview, by Dr. Jayakrishnan N. Nair, Published Online on [Dec. 18, 2020] https://defence.capital/2020/12/18/wearable-technologies-can-help-soldiers-survive-in-adverse-environment/.

"IOT Based Soldier E-Jacket Using GPS", Published at Journal of Interdisciplinary Cycle Research, by Prof. Swapnil Chaudhari et al., Published Online in [Mar. 2020] https://shorturl.at/euRZ7.

"Police Body-Worn Cameras and Privacy: Views and Concerns of Officers and Citizens", Published at International Journal of Police Science & Management, by Brigitte Poirier et al., Published Online on [Nov. 21, 2023] https://journals.sagepub.com/doi/pdf/10.1177/14613557231214383.

"LORA Based Soldier Tracking and Health Monitoring Device", Published at International Research Journal of Engineering and Technology, by Kruthikaran et al., Published Online in [Mar. 2023] https://www.irjet.net/archives/V10/I3/IRJET-V10I367.pdf.

"A Literature Review on IOT-Based Soldier Health Monitoring E-Jacket", Published at International Research Journal of Modernization in Engineering Technology and Science, by Ms. Dnyanada Meshram et al., Published Online in [Feb. 2023] https://www.irjmets.com/uploadedfiles/paper/issue_2_february_2023/33517/final/fin_irjmets1676464912.pdf.

"Body-Worn Cameras' Effects on Police Officers and Citizen Behavior: A Systematic Review", Published at Campbell Systematic Reviews, by Cynthia Lum et al., Published Online on [Sep. 9, 2020] https://onlinelibrary.wiley.com/doi/epdf/10.1002/cl2.1112.

"Enhancing Response Capabilities with Smartwatches in Public Safety", Published at the Public Safety Network, Found Online on [Mar. 12, 2024] https://www.publicsafety.network/wp-content/uploads/2021/01/Smartwatches-in-Public-Safety-White-Paper_FINAL.pdf.

"Police Tactical Vest: IoT and AI to Enhance Safety on Operations", Published at Mechatronics Canada, Published Online on [Mar. 1, 2024] https://www.mechatronicscanada.ca/product-news/police-tactical-vest-iot-ai/.

"Body-Worn Video Cameras for Law Enforcement Market Survey Report", Published at Homeland Security, Published Online in [Jun. 2015] https://www.dhs.gov/sites/default/files/publications/Body-Worn-Cams-MSR_0615-508_1.pdf.

"Police Body-Worn Cameras: Perceptions of Law Enforcement Leadership", Published at Springerlink, by John Ortiz Smykla, Oublished Online on [Dec. 4, 2015] https://link.springer.com/content/pdf/10.1007/s12103-015-9316-4.pdf.

"Geolocation Wearables for Enhanced Law Enforcement", Published at Utilities One, Published Online on [Nov. 15, 2023] https://utilitiesone.com/geolocation-wearables-for-enhanced-law-enforcement#anchor-0.

"Want to control your electronics with your tongue?", Published at ZDNET, by Jada Jones, Published Online on [May 13, 2023] https://www.zdnet.com/article/want-to-control-your-electronics-with-your-tongue-this-company-is-making-that-happen/.

"A Magnetic Wireless Tongue-Computer Interface", Published at IEEE Xplore, by Xueliang Huo et al., Published Online on [Jun. 11, 2007] https://www.researchgate.net/publication/4252014_A_Magnetic_Wireless_Tongue-Computer_Interface.

"A Hands-Free, Mouth Operated Joystick Computer Mouse Designed Specifically for Individuals With Disabled Hand Movement", by Quadlife, Published Online on [Sep. 17, 2020] https://quad.life/product.

"MouthPad Turns Your Tongue into a Mouse for Your Phone", Published at Engadget, by Cherlynn Low, Published Online on [Jan. 12, 2024] https://www.engadget.com/the-mouthpad-turns-your-tongue-into-a-mouse-for-your-phone-184541021.html?_fsig=dqmn468RiJE_pgKZXmIOHw--%7EA.

"Evaluation of the Tongue Drive System by Individuals with High-Level Spinal Cord Injury", Published at Conf Proc IEEE Eng Med Biol Soc, by Xueliang Huo et al., Published Online on [Mar. 12, 2024] https://www.ncbi.nlm.nih.gov/pmc/articles/PMC4467691/pdf/nihms698831.pdf.

"An Arch-Shaped Intraoral Tongue Drive System with Built-in Tongue-Computer Interfacing SoC", Published at Miniaturized Wireless Biosensors, by Hangue Park et al., Published Online on [Nov. 14, 2014]. https://www.mdpi.com/1424-8220/14/11/21565.

"Introducing Generative AI for Law Enforcement", by C3 AI, Published at Youtube, Published Online on [Aug. 10, 2023] https://www.youtube.com/watch?v=eO4cQjnwqgo.

"Vanderbilt Engineering Students Create "Smart Vest" to Save Police Officers", by Vanderbilt University, Published at Youtube, Published Online on [Apr. 27, 2017] https://www.youtube.com/watch?v=jq5DO3717E8.

"Smart Vest", by Harley-Davidson, Published at Youtube, Published Online on [Apr. 9, 2024] https://www.youtube.com/watch?v=C42bk5h4y-E.

"This Vest Can Save Lives", by Virginia Tech, Published at Youtube, Published online on [Sep. 1, 2015] https://www.youtube.com/watch?v=79x7_N6mTYo&t=6s.

"Vanderbilt Students Create Smart Police Vest", by Sarah McCarthy, Published at Newschannel 5, Published online on [Apr. 27, 2017] https://www.newschannel5.com/news/vanderbilt-students-create-smart-police-vest.

"Vanderbilt Students Develop Smart Police Vest That Calls for Backup", by Ariana Maia Sawyer, Published at the Tennessee, Published Online on [Apr. 25, 2017] https://www.tennessean.com/story/news/crime/2017/04/24/vanderbilt-students-develop-smart-police-vest-calls-backup/100854078/.

"Prototype "Smart Vest" Could Greatly Reduce Highway Worker Deaths and Injuries byTalking to Traffic", by Tom Jackson, Published at EquipmentWorld, Published Online on [Sep. 22, 2015] https://www.equipmentworld.com/roadbuilding/video/14963694/prototype-smart-vest-could-greatly-reduce-highway-worker-deaths-and-injuries-by-talking-to-traffic.

"Smart Vest: Wearable Multi-Parameter Remote Physiological Monitoring System", by P.S. Pandian, Published at Medical Engineering & Physics, Published Online on [Sep. 14, 2007] https://www.sciencedirect.com/science/article/abs/pii/S1350453307000975?via%3Dihub.

"Robust Speech Recognition via Large-Scale Weak Supervision", by Alec Radford et al., Published at Cornell University, Published Online on [Dec. 6, 2022] https://arxiv.org/pdf/2212.04356.

"Faster-whisper", Published at Github, Found Online on [May 1, 2024] https://github.com/SYSTRAN/faster-whisper.

"Insanely Fast Whisper", Published at Github, Found Online on [May 1, 2024] https://github.com/Vaibhavs10/insanely-fast-whisper.

"WhisperLive", Published at Github, Found Online on [May 1, 2024] https://github.com/collabora/WhisperLive.

"Whisper.cpp", Published at Github, Found Online on [May 1, 2024] https://github.com/ggerganov/whisper.cpp/tree/master.

"Exploration of Alerting Methods on Vest-Worn System", by Kristen P. Hines, Published at Virginia Polytechnic Institute and State University, Published online on [May 4, 2016] https://vtechworks.lib.vt.edu/server/api/core/bitstreams/af47ee5d-2b50-462d-9da7-bd7982a1ecf3/content.

(56) References Cited

OTHER PUBLICATIONS

"Artificial Intelligence and Face Recognition for Body Cams", by Hernan Cafiel, Published at Ebenezer Technologies, Published Online on [Dec. 9, 2022] https://ebenezertechs.com/face-recognition-body-cams/.
"Integrating Body-Worn Cameras, Drones, and AI: A Framework or Enhancing Police Readiness and Response", by Amanda Davies et al., Published at Oxford University Press, Published Online on [Dec. 13, 2023] https://academic.oup.com/policing/article/doi/10.1093/police/paad083/7471863.
"Security Analysis of First Responder Mobile and Wearable Devices", by Joshua M. Franklin, Published at National Institute of Standards and Technology Interagency, Published Online in [May 2020] https://nvlpubs.nist.gov/nistpubs/ir/2020/NIST.IR.8196.pdf.
"Body Worn Cameras With Facial Recognition Technology: When It Constitutes a Search", by Kelly Blount, Published at American University Washington College of Law, Published Online in [2017] https://core.ac.uk/download/pdf/327253044.pdf.
"Towards On-Device Face Recognition in Body-worn Cameras", by Ali Almadan, Published at IEEE International Workshop on Biometrics and Forensics, Published Online on [Apr. 7, 2021] https://arxiv.org/pdf/2104.03419.
"Law Enforcement's Pairing of Facial Recognition Technology with Body-Worn Cameras Escalates Privacy Concerns", by Katelyn Ringrose, Published at Virginia Law Review, Published Online on [Feb. 18, 2019] https://virginialawreview.org/wp-content/uploads/2020/12/04.%20Final%20Ringrose.pdf.
"Police use of facial recognition technology: The potential for engaging the public through co-constructed policy-making", by Dallas Hill, Published at International Journal of Police Science & Management, Published Online on [Apr. 4, 2022] https://journals.sagepub.com/doi/epub/10.1177/14613557221089558.
"Information Technology on the Beat: The Impacts of Body-Worn Camera and Facial Recognition Technology on Public Safety", by Jiyong Park, Published at University of North Carolina, Published Online on [Jul. 24, 2019] https://shorturl.at/bfqL.4.
"Chilling: The Constitutional Implications of Body-Worn Cameras and Facial Recognition Technology at Public Protests", by Julian R. Murphy, Published at Washington and Lee University, Published Online on [Aug. 30, 2018] https://scholarlycommons.law.wlu.edu/cgi/viewcontent.cgi?article=1104&context=wluir-online.
"Recent Advances in Wearable Sensors for Health Monitoring", by Mary M. Rodgers, Published at IEEE Sensors Journal, Published online on [Sep. 16, 2014] https://shorturl.at/nwxY2.
"Dress for Success: Embedded Health Sensors in the Future Soldier", by Paul Dhillon, Published at Journal of Military, Veteran and Family Health, Published Online in [2022] https://jmvfh.utpjournals.press/doi/pdf/10.3138/jmvfh-2021-0095.
"How Biometric Monitoring Will Save Law Enforcement Lives", by Lt. Grant Bedford, Published at Police1, Published Online on [Dec. 18, 2019] https://www.police1.com/health-fitness/articles/how-biometric-monitoring-will-save-law-enforcement-lives-91PHTP83yHZNAOdw/#:~:text=These%20devices%20could%20be%20placed,monitoring%20program%20to%20other%20departments.
"Biometrics and Policing: A Protocol for Multichannel Sensor Data Collection and Exploratory Analysis of Contextualized Psychophysiological Response During Law Enforcement Operations", by Robert D Furberg et al., Published at JMIR Research Protocols, Published Online on [Mar. 17, 2017] https://pdfs.semanticscholar.org/e725/3d89aa98ffc8036163acdea18137db13464d.pdf.
"Real-Time Remote Health Monitoring Systems Using Body Sensor Information and Finger Vein Biometric Verification: A Multi-Layer Systematic Review", by A. H. Mohsin et al., Published at Journal of Medical Systems, Published Online on [Oct. 16, 2018] https://shorturl.at/IJPQ5.
"Warfighter Physiological and Environmental Monitoring", by G.A. Shaw et al., Published at Massachusetts Institute of Technology, Published Online on [Nov. 1, 2024] https://apps.dtic.mil/sti/tr/pdf/ADA428022.pdf.
"Wearable Health Devices—Vital Sign Monitoring, Systems and Technologies", by Duarte Dias et al., Published at Wearable Smart Devices, Published Online on [Jul. 25, 2018] https://www.mdpi.com/1424-8220/18/8/2414.
"On the Real-Time Prevention and Monitoring of Exertional Heat Illness in Military Personnel", by M.J. Buller, Published at Journal of Science and Medicine in Sport, Published Online on [Apr. 26, 2021] https://www.jsams.org/action/showPdf?pii=S1440-2440%2821%2900104-3.
"The Power of Biometrics: A Game-Changer for Officer Wellness", by Deputy Chief Aaron Johnson, Published at Police1, Published online on [Mar. 2, 2024] https://www.police1.com/wellness-week/the-power-of-biometrics-a-game-changer-for-officer-wellness.
"Wearable Tech for Law Enforcement", Published at inTime, Found Online on [May 3, 2024] https://intime.com/industries/police/wearable-tech-for-law-enforcement/.
"Can Body Cameras Reduce Altercations in a Correctional Facility?", by Dawn Lenzmeier, published at NEWCOM, Published Online on [Nov. 30, 2022] https://newcomglobal.com/wp-content/uploads/2022/11/NEWCOM-Body-Cameras-Reduce-Altercations-in-a-Correctional-Facility.pdf.
"Body Cameras in Corrections? Get ready for Game-Changing Benefits", Published at Utility, Published online on [Feb. 29, 2024] https://www.utility.com/blog/body-cameras-in-corrections-get-ready-for-game-changing-benefits/.
"Body-Worn Camera Activation in Prisons: Understanding Correctional Officers' Decision-Making and Use of Discretion", by Dodd, Published at Security Journal, Published Online on [May 26, 2023] https://research-repository.griffith.edu.au/server/api/core/bitstreams/b534906f-5064-4e5e-94a7-e0f8cf1c99a8/content.
"A Randomized Controlled Trial of the Impact of Body-Worn Cameras in the Loudoun County, VA, Adult Detention Center", by Brittany C. Cunningham et al., Published at CNA, Published Online in [Jun. 2023] https://www.ojp.gov/pdffiles1/nij/grants/307338.pdf.
"Body-Worn Camera Activation in Prisons: Understanding Correctional Officers' Decision-Making and Use of Discretion", by Shanon Dodd et al., Published at Security Journal, Published on https://hizligecisodemesi.net/body-worn-camera-scholarly-articles-7cf3.
"Policing Universities: Exploring the use of body-worn cameras (BWCs) by private campus security officers", by Francesca Menichelli, Published at Policing and Society, Published Online on [Feb. 17, 2024] https://www.tandfonline.com/doi/epdf/10.1080/10439463.2024.2315583?needAccess=true.
"Transition of Body-Worn Cameras from Policing to Corrections", by Jasmine Kaur, Published at EBP Society, Published online on [Mar. 24, 2023] https://www.ebpsociety.org/blog/education/547-transition-of-body-worn-cameras-from-policing-to-corrections.
"Life-Saving Suits for Law Enforcement: Looking Ahead at Wearable Technology", by Thomas B. Cashion et al., Published at International Association of Chiefs of Police, Published Online on [Jun. 27, 2018] https://www.policechiefmagazine.org/life-saving-wearable-technology/.
"Policing Faces: The Present and Future of Intelligent Facial Surveillance", by Lachlan Urquhart et al., Published at Information & Communication Technology Law, Published online on [Oct. 28, 2021] https://www.pure.ed.ac.uk/ws/portalfiles/portal/239314767/UrquhartLMirandaD2021ICTLPolicingFaces.pdf.
"Hardware to Protect Against Drones", by Dedrone, Found Online on [May 3, 2024] https://www.dedrone.com/products/counter-drone-technology.
"Counter-Drone Solutions", ARDRONIS, Found Online on [May 3, 2024] https://www.rohde-schwarz.com/hk/products/aerospace-defense-security/counter-drone-systems_250881.html.
"Protectors of Critical Infrastructure are Enabled by Spotter Radars to Prevent Harm", by Spotter Global, Found Online on [May 3, 2024] https://www.spotterglobal.com/.
"Development of Equipment for Satellite Navigation Systems GLONASS, GPS, GALILEO", by KB Center, Found Online on [May 3, 2024] http://www.kbcentr.com.ua/.
"Design Smart Antenna for GPS/GLONASS Using Adaptive Beamforming", Herasymenko K.V et al., Lviv Polytechnic National University Institutional Repository, Published Online in [Jan. 2012] https://shorturl.at/osIS5.

(56) References Cited

OTHER PUBLICATIONS

"Equipment Optimization for Weather Balloon and Ground-Based Weather Stations Using GNSS", by A. G. Laush, Published at International Conference on Antenna Theory and Techniques (ICATT), Published Online in [2017] https://sci-hub.yncjkj.com/10.1109/icatt.2017.7972662.

"A Novel Dual Band Microstrip Antenna Array for Receiving of Satellite Navigational Signals GPS/GLONASS/GALILEO", by Sergiy Y. Martynyuk et al., Published at International Conference on Antenna Theory and Techniques Published Online in [2015] https://sci-hub.yncjkj.com/10.1109/icatt.2015.7136781.

"Model of Mapping Function for the Calculation of Zenith Tropospheric Delay", by V.I. Lutsenko et al., Published at International Kharkov Symposium on Physics and Engineering of Microwaves, Millimeter and Submillimeter Waves, Published Online in [2013] https://sci-hub.53yu.com/10.1109/msmw.2013.6622052.

"Body-Worn Camera Activation in Prisons: Understanding Correctional Officers' Decision-Making and Use of Discretion", Published at Security Journal, Published by Shannon Dodd et al., Published Online on [May 26, 2023] https://link.springer.com/article/10.1057/s41284-023-00380-7.

"Airfence", by Sensofusion, Found Online on [Jul. 19, 2024] https://sensofusion.com/airfence/.

"A Real-Time End-to-End Multilingual Speech Recognition Architecture", Published at IEEE Journal of Selected Topics in Signal Processing, Published by Javier Gonzalez-Dominguez et al., Published Online on [Oct. 23, 2014] https://ieeexplore.ieee.org/stamp/stamp.jsp?tp=&arnumber=6935076.

"Real-Time Multilingual Speech Recognition and Speaker Diarization System Based on Whisper Segmentation"; Published at PeerJ Computer Science, Published by Ke-Ming Lyu et al., Published Online on [Mar. 29, 2024] https://peerj.com/articles/cs-1973.pdf.

"Simultaneous Speech-To-Speech Translation System With Neural Incremental ASR, MT, and TTS", Published at Nara Institute of Science and Technology, Published by Katsuhito Sudoh et al., Published Online on [Nov. 10, 2020] https://arxiv.org/pdf/2011.04845.

"Simple, Lexicalized Choice of Translation Timing for Simultaneous Speech Translation", Published at Nara Institute of Science and Technology, Published by Tomoki Fujita, Published Online in [Jan. 2013] https://www.isca-archive.org/interspeech_2013/fujita13_interspeech.pdf.

"Real Time Speech Translator", Published at Czech Technical University (CTU), Published by Xavier Garcia Cabrera, Published Online on [Jun. 25, 2008] https://upcommons.upc.edu/bitstream/handle/2099.1/6128/memoria.pdf?sequence=1&isAllowed=y.

"An Empirical Simulation-based Study of Real-Time Speech Translation for Multilingual Global Project Teams", Published at International Symposium on Empirical Software Engineering and Measurement, Published by Fabio Calefato et al., Published Online on [Sep. 18, 2014] https://collab.di.uniba.it/fabio/wp-content/uploads/sites/5/2014/05/ESEM2014_camera-ready.pdf.

"Turning Whisper into Real-Time Transcription System", Published at International Joint Conference on Natural Language Processing (IJCNLP) and the 3rd Conference of the Asia-Pacific Chapter of the Association for Computational Linguistics (AACL), Published by Dominik Macháček et al., Published Online in [Nov. 2023] https://aclanthology.org/2023.ijonlp-demo.3.pdf.

"Precision Payload Delivery System", by Corvo, Found Online on [Jul. 19, 2024] https://corvouas.com.au/wp-content/uploads/CORVO-PPDS-web-version-23082023-compressed.pdf.

"RQ-20 Puma", by AeroVironment, Inc., Published Online on [Aug. 4, 2020] https://english.iswnews.com/14555/military-knowledge-rq-20-puma-drone/.

"Counter Drone Systems", by Adani Defence and Aerospace, Found Online on [Jul. 19, 2024] https://www.adanidefence.com/en/counter-drone-systems.

"Dragon Eye Miniature UAV", by Defence Update, Published Online on [Aug. 23, 2005] https://defense-update.com/20050823_dragon-eye.html#google_vignette.

"Countering the UAS Threat", by Defence Update, Published by Tamir Eshel, Published Online on [Jun. 27, 2024] https://defense-update.com/20240627_c-uas-2.html#google_vignette.

"Multilingual Speech Transcription and Translation System", Published at International Journal of Advanced Research in Science, Communication and Technology (IJARSCT), Published by Dheeraj K N et al., Published Online in [Jun. 2024] https://ijarsct.co.in/Paper18843.pdf.

"Real Time Direct Speech-to-Speech Translation", Published at International Research Journal of Engineering and Technology (IRJET), Published by Sanchit Chaudhari et al., Published Online in [Jan. 2022] https://www.irjet.net/archives/V9/11/IRJET-V9I1104.pdf.

"Methods and algorithms of correction of propagation factor influence on errors of measurement coordinates receivers GNSS", Published at International Crimean Conference Microwave & Telecommunication Technology, Published by V.I. Lutsenko et al., Published Online on [Oct. 22, 2012] https://ieeexplore.ieee.org/document/6335995/authors#authors.

"Elimination of abnormally high errors of determining the coordinates of global navigation satellite system receivers", Published at International Crimean Conference Microwave & Telecommunication Technology, Published by V.I. Lutsenko et al., Published Online on [Nov. 4, 2013] https://ieeexplore.ieee.org/document/6652840/authors#authors.

"Interpolation method of introducing differential corrections into measurements of coordinate and pseudoranges in global navigation systems", Published at International Crimean Conference Microwave & Telecommunication Technology, Published by V.I. Lutsenko et al., Published Online on [Nov. 4, 2013] https://ieeexplore.ieee.org/document/6652837/authors#authors.

"Fixed-Wing UAV Systems: Modular VTOL, Long-Range Maritime UAV, Tactical ISR UAS", by Tekever, Found Online on [Jul. 19, 2024] https://www.unmannedsystemstechnology.com/company/tekever/.

* cited by examiner

FIG. 15

USER INTERFACE

NAVIGATION AND CONTROL TOOL 1502

STOP ANALYZING

ALL INCIDENTS — 1506

SHARE — 1508

TITLE OF THE VIDEO

● LIVE

1504

REALTIME ANALYSIS    TRANSCRIPT VIEW

ENVIRONMENT
THE ENVIRONMENT APPEARS TO BE AN URBAN OUTDOOR SETTING, LIKELY IN A DEVELOPED CITY AREA, WITH A FOCUS ON A ROADSIDE SCENE. IT IS DAYTIME, THE READ MORE

PERSONS

SUSPECT 1
THE INDIVIDUAL IS A MALE (20-30 YO) BASED ON THE UNIFORM WITH BADGE AND GANG AFFILIATION WITH LOS OLIVOS CRIPS

ATTENTIVE    FOCUS

OVERALL
THE SCENE SEEMS DYNAMIC AND THERE ARE IMMEDIATE INDICATIONS OF SAFETY CONCERNS FROM THE ENVIRONMENT OR THE VISIBLE INDIVIDUAL. THE SITUATION APPEARS TO BE ABNORMAL FOR A POLICE OFFICER IN THE LINE OF DUTY. CONTINUOUS ASSESSMENT IS REQUIRED DUE TO THE POTENTIALLY DYNAMIC NATURE OF LAW ENFORCEMENT ENCOUNTERS. READ MORE

THREATS

THREAT

GUN 132G (2:13)
SEEN IN THE SUSPECT HAS GUN IN HIS HAND AS THEY EXIT CAR

SHERATON HOTEL, 15 CENTRAL AVE, LOS OLIVOS

FEBRUARY 13, 2026 (8:45 PM)

USER INTERFACE VIEW 1550

| | BODY WORN CAMERAS 216 | TACTICAL GEAR 104 |
|---|---|---|
| DETECTS AND ALERTS OFFICER OF WEAPONS | ✗ | ✓ |
| ALERTS OFFICER OF OPIOID AND ALCOHOL SYMPTOMS | ✗ | ✓ |
| REAL TIME LANGUAGE TRANSLATION | ✗ | ✓ |
| DESCRIBES WHAT HAPPENED IN WORDS | ✗ | ✓ |
| RECORDS BODY VIDEO AT INCIDENTS | ✓ | OPTIONAL |

TABLE VIEW 1750

FIG. 17

| | TRADITIONAL TACTICAL VEST | TACTICAL GEAR 104 |
|---|---|---|
| DETECTS AND ALERTS OFFICER OF WEAPONS | ☒ | ☑ |
| ALERTS OFFICER OF OPIOID AND ALCOHOL SYMPTOMS | ☒ | ☑ |
| REAL TIME LANGUAGE TRANSLATION | ☒ | ☑ |
| DESCRIBES WHAT HAPPENED IN WORDS | ☒ | ☑ |
| PROTECTS FROM GUNSHOTS | ☑ | ☑ |

TABLE VIEW 1850

FIG. 18

BODY SAFETY DEVICE WITH VISUAL SENSING AND HAPTIC RESPONSE USING ARTIFICIAL INTELLIGENCE

CLAIM OF PRIORITY

This Application is a conversion Application of, claims priority to, and incorporates by reference herein the entirety of the disclosures of:

U.S. Provisional Patent Application No. 63/614,022 titled MULTI-FUNCTIONAL WEARABLE AI-ENABLED PENDANT APPARATUS, SYSTEM, AND METHOD OF AMBIENT DATA ANALYSIS AND COMMUNICATION IN LAW ENFORCEMENT, FIRE, MEDICAL RESPONDER, PRIVATE SECURITY, JOURNALISM, COMMERCIAL AND MILITARY OPERATIONAL ENVIRONMENTS filed on Dec. 22, 2023, U.S. Provisional Patent Application No. 63/616,817 titled EMOTIONALLY INTELLIGENT AERIAL DRONE SYSTEM FOR ENHANCED SITUATIONAL AWARENESS AND RESPONSIVE OPERATIONS filed on Jan. 1, 2024, U.S. Provisional Patent Application No. 63/622,514 titled HAPTIC FEEDBACK RESPONSIVE TO A THREAT IDENTIFIED THROUGH A GENERATIVE ARTIFICIAL INTELLIGENCE BODY WORN APPARATUS filed on Jan. 18, 2024, U.S. Provisional Patent Application No. 63/626,075 titled SECURE EDGE MESH NETWORK SYSTEM FOR ENHANCED VISUAL INTERPRETATION AND REAL-TIME SITUATIONAL AWARENESS IN COMBAT ZONES filed on Jan. 29, 2024, U.S. Provisional Patent Application No. 63/552,265 titled MODULAR INTEGRATED BODY CAMERA SYSTEM FOR ENHANCED ERGONOMICS, OPERATIONAL EFFICIENCY, AND TECHNOLOGICAL ADAPTABILITY IN LAW ENFORCEMENT EQUIPMENT filed on Feb. 12, 2024, and U.S. Provisional Patent Application No. 63/554,360 titled ENHANCED SITUATIONAL AWARENESS THROUGH A HAPTIC WEARABLE DEVICE OF A POLICE OFFICER OR A WARFIGHTER, ACTIVATED BY A NEARBY NETWORKED VEHICLE OR A STATIONARY SENSOR UPON DETECTING A THREAT filed on Feb. 16, 2024; and U.S. Provisional Patent Application No. 63/555,014 titled TRAUMATIC INJURY COMMUNICATION METHODOLOGY AND SYSTEM THROUGH A BODY WORN DEVICE filed on Feb. 17, 2024.

FIELD OF TECHNOLOGY

The present disclosure relates generally to the field of wearable personal safety technology. This disclosure relates generally to a body safety device with visual sensing and haptic response using artificial intelligence.

BACKGROUND

Police and military peacekeepers may face threats that they may not immediately perceive. These threats can come in various forms and may not always be easily identifiable. For example, in conflict zones and volatile areas, peacekeepers may not always be aware of hidden dangers like landmines or improvised explosive devices (IEDs). These threats can be concealed and may not be immediately visible, posing a significant risk to the safety of peacekeepers. Hostile forces may plan and execute ambushes against peacekeeping forces. These ambushes can occur suddenly, catching peacekeepers off guard and leading to casualties. In some situations, combatants may blend in with the civilian population, making it difficult for peacekeepers to identify potential threats. This can create a situation where peacekeepers do not perceive the danger until it's too late. Snipers and sharpshooters can pose a threat from a distance, making it challenging for peacekeepers to perceive their presence until shots are fired.

Insurgent groups may employ guerrilla tactics, hit-and-run attacks, and hit-and-hide strategies. These tactics can create an environment where peacekeepers may not always perceive the imminent threat. Enemy combatants might infiltrate peacekeeping camps or units, posing as friendly forces. This infiltration can lead to internal threats that peacekeepers may not initially perceive. Psychological warfare can be used to manipulate perceptions and create confusion among peacekeepers. Disinformation and propaganda can make it difficult to accurately assess threats.

In active combat zones such as in the Middle East or Ukraine, there are various potential threats that military personnel may encounter. Warfighters and police may be faced with ambushes and surprise attack's, as insurgents may exploit the terrain and urban environments for cover and concealment. This can be particularly acute in low light and nighttime conditions, where potholes, hidden persons, and/or navigational challenges can pose difficulties. In areas with tall buildings or dense urban areas, snipers and sharpshooters can pose a significant threat to military personnel. IEDs placed along patrol routes are a constant danger, with insurgents frequently using them to target military convoys. There may be a risk of attacks using non-conventional methods, such as chemical or biological agents, which can have devastating effects.

Insurgent groups may employ guerrilla warfare tactics, including blending in with the civilian population and launching hit-rand-run attacks, Unexploded bombs or mines from previous conflicts that remain active and dangerous can be a hazard in combat zones. The use of small unmanned aerial vehicles (UAVs) equipped with cameras or explosives for surveillance or direct attacks is a growing concern. Electronic interference, such as jamming or intercepting communications and disrupting electronic devices, can hinder military operations. In addition, individuals carrying explosive devices on their person, intending to detonate them in close proximity to military targets, may pose a significant and immediate threat.

In densely populated urban areas, individuals may carry concealed firearms or weapons, Police officers may not always perceive the presence of these weapons until a situation escalates, posing a significant dancer. Criminal activities such as drug dealing, illegal gambling, or human trafficking can occur discreetly within urban neighborhoods. Officers may need to rely on intelligence and investigative work to uncover these hidden threats, which may not always be possible. Gangs operating within urban environments can be a constant threat. Gang members may blend into the community, making it difficult for officers to identify them until a confrontation arises.

Urban areas may witness protests and civil unrest. These events can quickly escalate, with officers facing threats like projectiles. Molotov cocktails, and/or aggressive crowds may not be immediately anticipated. In densely populated urban areas, hostage situations can develop rapidly, and officers may not perceive a threat until it is too late. Pursuits through city streets can endanger officers and the public. The threat of a suspect fleeing at high speeds may not be immediately apparent until a pursuit begins. Criminals may plan ambushes against police officers, especially during routine patrols or traffic stops. These ambushes can catch officers off guard, Responding to domestic violence calls can be unpredictable. Officers may not always perceive the potential for violence until they arrive at the scene, making de-escalation skills crucial, Officers can sometimes encounter individuals in mental health crises. These situations can quickly escalate, with officers unable to assess the level of threat and respond accordingly.

SUMMARY

Disclosed are a method, system, and apparatus of a body safety device with visual sensing and haptic response using artificial intelligence.

In one aspect, a body worn safety device includes a visual sensor integrated into a tactical gear and a haptic feedback device is integrated in the tactical gear. The haptic feedback device vibrates when the visual sensor detects an ambient threat to a wearer of the tactical gear.

The haptic feedback device may detect the ambient threat using an artificial intelligence based threat detection model. The visual sensor may be part of an array of visual sensors around the torso of the wearer. The artificial intelligence based threat detection model may detect and/or analyze human emotion of an individual in an ambient area to the wearer using computer vision and/or auditory sensing to detect the presence and/or absence of the ambient threat. The visual sensor may be a front-facing visual sensor embedded in both shoulder areas of the tactical gear such that the wearer is able to sense the ambient threat through the haptic feedback device when the ambient threat approaches the wearer of the tactical gear. The visual sensor may be embedded in a center back area of the tactical gear such that the wearer may be able to sense the ambient threat through the haptic feedback device when the ambient threat approaches from behind the wearer of the tactical gear.

A language translator module may be integrated in a center front area through which the wearer is able to bi-directionally communicate with an individual in the ambient environment using any language other than a primary language spoken by the wearer when the language translator module is activated.

A combined memory and power module may be removable from the tactical gear. The combined memory and power module may power the visual sensor and/or the haptic feedback device. The combined memory and power module may include a memory storage which auto downloads sensory data captured from the visual sensor and the haptic feedback device when the combined memory and power module is docked in a docking station. The combined memory and power module may simultaneously charge multiple devices on the wearer including a mobile phone, a body worn camera, and/or the visual sensor. A processing unit may be removable from the tactical gear and which provides optional processing and sensor capabilities to the body worn safety device. A user authentication means may activate the visual sensor and the haptic feedback device if the wearer is an authorized user.

The visual sensor may serve as a visual recording device. The haptic feedback device may be part of an array of haptic feedback device to vibrate at different locations of a body of the wearer depending on a directional location of the ambient threat. An intensity of vibration of the haptic feedback device may be dependent on the proximity of the ambient threat to the wearer. A pattern of vibration of the haptic feedback device may be dependent on a type of threat. The visual sensor may automatically document a health condition of an injured individual in the ambient environment and communicate that information to a nearby hospital where the injured individual is to be transported. The haptic feedback device may vibrate when a different wearer of a different body worn safety device detects a different ambient threat in the same ambient environment to the wearer. The different body worn safety device may be communicatively coupled with the body worn safety device through an ad-hoc edge mesh network formed between the body worn safety device and the different body worn safety device.

The body worn safety device may solely be a real time observation device that provides early warnings to the wearer of any one of a pre-assaultive threat, an opioid addiction warning, an intoxicated state warning, and a mental health warning in an ambient environment.

The body worn safety device may vibrate when an unmanned aerial vehicle networked with the body worn safety device in an active incident area perceives an ambient threat nearby to the wearer. The unmanned aerial vehicle may be part of an emotionally aware drone swarm which uses any one of a plurality of sensors to detect aggressive emotions in a riotous gathering. The body worn safety device may vibrate when a land vehicle networked with the body worn safety device perceives an ambient threat nearby to the wearer. Only a subset of an array of haptic feedback device on the body worn safety device closest to the ambient threat may vibrate based on a directionality of the ambient threat. The body worn safety device may include a global positioning system.

The body worn safety device may also vibrate when a stationary sensory device networked with the body worn safety device perceives an ambient threat nearby to the wearer. The visual sensor may be embedded in a flush manner in a shoulder area of the tactical gear such that movement of a tactical rifle is not impeded by the visual sensor. The body worn safety device may not permanently store real-time threat analysis.

A biometric sensor of the tactical gear may measure the biometric information of the wearer. The biometric sensor may be detachable from the tactical gear and placeable on an injured person nearby to the wearer through an armband extendable from the biometric sensor when it is removed from the tactical gear. The biometric sensor may automatically store and/or communicate the biometric information of the injured person to a hospital when removed from the tactical gear and placed on an arm of the injured person, when the injured person is en route to the hospital.

A single-chip Software-Defined Vision Sensor (SDVS) with integrated neuromorphic sensing and processing may deliver real time vision intelligence with privacy at source to the body worn safety device to detect an obstacle and/or the ambient threat in a path of the wearer during low light conditions and trigger the haptic feedback device when the obstacle and/or the ambient threat is detected.

A spherical disc may be wirelessly coupled with the body worn safety device that is carryable and/or throwable by the wearer. The spherical disc may automatically unfurl when it is thrown by the wearer onto a level surface, such that a camera of the spherical disc is perpendicularly manifested and actively records when in the unfurled state. The haptic feedback device on the body worn safety device may vibrate when an ambient threat is visible to the camera of the spherical disc in the unfurled state.

A retainer placed in a mouth of the wearer may bookmark a geospatial location based on an action in the mouth of the wearer and/or to request help to arrive at the geospatial location. The body worn safety device may communicate without electronic signature through a non-radiative, human-body-centered communication network. The body worn safety device may include a taser integrated into the tactical gear to automatically deliver an electric shock to an attacker who is physically wrestling with the wearer when the artificial intelligence based threat detection model detects a physical assault. The visual sensor may be a thermal imaging sensor that detects heat signatures emitted by objects and converts them into visual data. An audiovisual data of the visual sensor closest to the haptic feedback device may be automatically stored in a combined memory and power module for a configurable one of (1) a short period of time prior to the vibration of the haptic feedback device, (2) during the vibration of the haptic feedback device, and/or (3) another short period of time after the vibration of the haptic feedback device stops vibrating.

In another aspect, a body worn safety device, includes an array of visual sensors around a torso of a wearer such that ambient threats around the wearer are captured through an artificial intelligence based threat detection model, and an array of haptic feedback device to vibrate at different locations of a body of the wearer depending on a directional location of the ambient threat using the artificial intelligence based threat detection model.

In yet another aspect, a body worn safety device, includes a visual sensor embedded in a center front area of the tactical gear such that the wearer is able to sense the ambient threat through the haptic feedback device when the ambient threat approaches from the front of the wearer of the tactical gear. A language translator module is integrated with center front area through which the wearer is able to bi-directionally communicate with an individual in the ambient environment using any language other than a primary language spoken by the wearer when the language translator module is activated and a haptic feedback device integrated in the tactical gear vibrates when the visual sensor detects an ambient threat to a wearer of the tactical gear.

The methods and systems disclosed herein may be implemented in any means for achieving various aspects, and may be executed in a form of a non-transitory machine-readable medium embodying a set of instructions that, when executed by a machine, cause the machine to perform any of the operations disclosed herein. Other features will be apparent from the accompanying drawings and the detailed description that follows.

BRIEF DESCRIPTION OF THE DRAWINGS

The embodiments of this invention are illustrated by way of example and not limitation in the figures of the accompanying drawings, in which like references indicate similar elements and in which:

FIG. 15 is another user interface view of the system of the body worn safety device of FIG. 1, illustrating a realtime analysis of a video and a transcript of an incident displayed on the user device, according to one embodiment.

FIG. 17 is a table view illustrating the comparative analysis of the generative artificial intelligence (AI) of body worn safety device of FIG. 1, to analyze video footage, according to one embodiment.

FIG. 18 is another table view illustrating the comparative analysis of the generative artificial intelligence (AI) of body worn safety device of FIG. 1, according to one embodiment.

Figure 1:
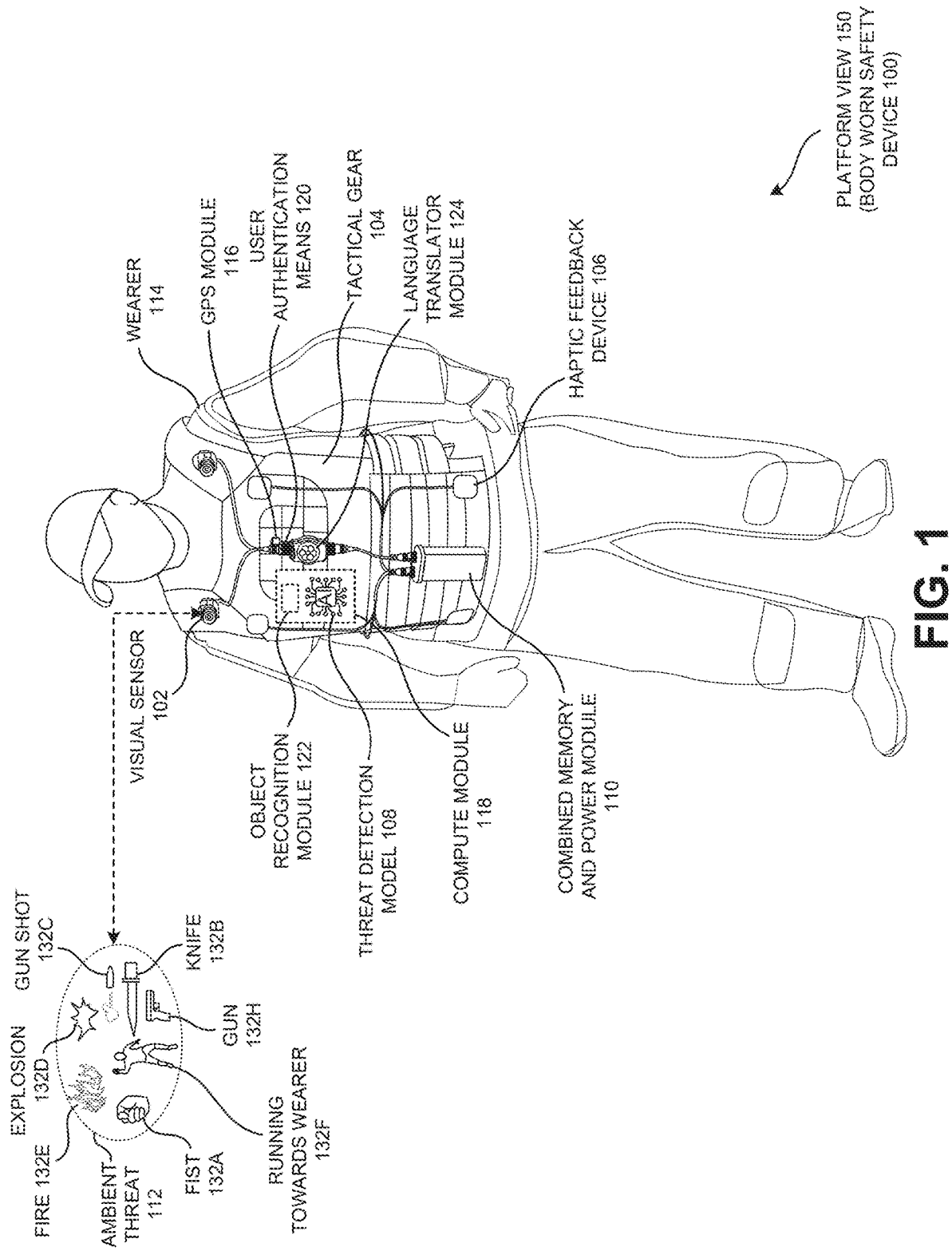
FIG. 1 is a platform view illustrating a body worn safety device with an array of visual sensors to detect an ambient threat using an artificial intelligence based threat detection model to generate a haptic response, according to one embodiment.

Other features of the present embodiments will be apparent from the accompanying drawings and from the detailed description that follows.

DETAILED DESCRIPTION

Disclosed is a method, system of a body safety device with visual sensing and haptic response using artificial intelligence. The GovGPT DragonFly™ represents a significant advancement in personal security technology, according to one embodiment. By harnessing the power of generative AI and haptic feedback, it provides a highly intuitive, responsive, and personalized threat detection system, significantly enhancing the safety and operational effectiveness of those in high-risk environments, according to one embodiment.

The methods and systems disclosed herein may be implemented in any means for achieving various aspects, and may be executed in a form of a non-transitory machine-readable medium embodying a set of instructions that, when executed by a machine, cause the machine to perform any of the operations disclosed herein. Other features will be apparent from the accompanying drawings and the detailed description that follows.

In one embodiment, a body worn safety device 100 includes a visual sensor 102 integrated into a tactical gear 104 and a haptic feedback device 106 integrated into the tactical gear 104. The haptic feedback device 106 vibrates when the visual sensor 102 detects an ambient threat 112 to a wearer 114 of the tactical gear 104. The haptic feedback device 106 may detect the ambient threat 112 using an artificial intelligence based threat detection model 108. The visual sensor 102 may be part of an array of visual sensors 200 around a torso 1900 of the wearer 114. The artificial intelligence based threat detection model 108 may detect and/or analyze human emotion of an individual in an ambient area to the wearer 114 using computer vision and/or auditory sensing to detect the presence or absence of the ambient threat 112.

The visual sensor 102 may be a front-facing visual sensor 202 embedded in both shoulder areas 1902 of the tactical gear 104 such that the wearer 114 is able to sense the ambient threat 112 through the haptic feedback device 106 when the ambient threat 112 approaches the wearer 114 of the tactical gear 104 (e.g.m from a blindspot area). The visual sensor 102 may be embedded in a center of a back area 214 of the tactical gear 104 such that the wearer 114 may be able to sense the ambient threat 112 through the haptic feedback device 106 when the ambient threat 112 approaches from behind the wearer 114 of the tactical gear 104.

A language translator module 124 may be integrated with center front area 216 through which the wearer 112 is able to bi-directionally communicate with an individual 606 in the ambient environment 600 using any language 602 other than a primary language 608 spoken by the wearer 112 when the language translator module 124 is activated. In one embodiment, the visual sensor 102 may be a thermal imaging sensor or thermal camera that detects infrared radiation emitted by objects, and heat signatures emitted by objects and converts them into images or video footage.

A combined memory and power module 110 may be removable from the tactical gear 104. The combined memory and power module 110 may power the visual sensor 102 and/or the haptic feedback device 106. The combined memory and power module 110 may include a memory storage which auto downloads sensory data 704 captured from the visual sensor 102 and the haptic feedback device 106 when the combined memory and power module 110 is docked in a docking station 702. An audiovisual data of the visual sensor closet to the haptic feedback device 106 may be automatically stored in a combined memory and power module 110 for a configurable one of (1) a short period of time prior to the vibration of the haptic feedback device 106, (2) during the vibration of the haptic feedback device 106, and/or (3) another short period of time after the vibration of the haptic feedback device 106 stops vibrating. The combined memory and power module 110 may simultaneously charge multiple devices on the wearer 112 including a mobile phone, a body worn camera 216, and/or the visual sensor 102. A processing unit may be removable from the tactical gear 104 and which provides optional processing and sensor capabilities to the body worn safety device 100. A user authentication means 120 may activate the visual sensor 102 and the haptic feedback device 106 if the wearer 112 is an authorized user.

The visual sensor 102 may serve as a visual recording device (e.g., a body worn camera 216). The haptic feedback device 106 may be part of an array of haptic feedback devices 210 to vibrate at different locations of a body of the wearer 112 depending on a directional location of the ambient threat 112. An intensity 910 of vibration of the haptic feedback device 106 may be dependent on the proximity of the ambient threat 500 to the wearer 114. A pattern (e.g., a haptic pattern 902, 904, 906) of vibration of the haptic feedback device 106 may be dependent on a type of threat (e.g., a fist 132A, weapon 132B, gun shot 132C, explosion 132D, fire 132E, attacker running towards wearer 132F, a gun 132H, etc.). The visual sensor 102 may automatically document a health condition (e.g., biometric information 1006 using biometric sensor 1002) of an injured individual 1000 in the ambient environment 600 and communicate that information to a nearby hospital 1008 where the injured individual 1000 is to be transported. The haptic feedback device 106 may vibrate when a different wearer 2314 of a different body worn safety device 100 to detect a different ambient threat 112 in the same ambient environment 600 to the wearer 114. The different body worn safety device may be communicatively coupled with the body worn safety device 100 through an ad-hoc edge mesh network formed between the body worn safety device 100 and the different body worn safety device.

The body worn safety device 100 may solely be a real time observation device that provides early warnings to the wearer 114 of any one of a pre-assaultive threat (e.g., ambient threat 112), an opioid addiction warning, an intoxicated state warning, and a mental health warning in an ambient environment 600. The visual sensor 102 may be a front facing visual sensor 202 embedded in a flush manner in a shoulder area 1902 of the tactical gear 104 such that movement of a tactical rifle 1906 is not impeded by the visual sensor 102. The body worn safety device 100 may not permanently store real-time threat analysis.

The body worn safety device 100 may vibrate when an unmanned aerial vehicle 802 networked with the body worn safety device 100 in an active incident area perceives the ambient threat 112 nearby to the wearer 114. The unmanned aerial vehicle 802 may be part of an emotionally aware drone swarm 800 which uses any one of a plurality of sensors to detect aggressive emotions in a riotous gathering 806. The body worn safety device 100 may vibrate when a land vehicle 804 networked with the body worn safety device 100 perceives the ambient threat 112 nearby to the wearer 114. Only a subset of an array of haptic feedback device 210 on the body worn safety device 100 closest to the ambient threat 112 may vibrate based on a directionality of the ambient threat 112. The body worn safety device 100 may include a global positioning system (e.g., GPS module 116).

The body worn safety device 100 may also vibrate when a stationary sensory device 808 networked with the body worn safety device 100 perceives an ambient threat nearby to the wearer 114. The visual sensor 102 may be embedded in a flush manner in a shoulder area 1902 of the tactical gear 104 such that movement of a tactical rifle 1906 is not impeded by the visual sensor 102. The body worn safety device 100 may not permanently store real-time threat analysis.

A biometric sensor 1002 of the tactical gear 104 may measure a biometric information 1006 of the wearer 114. The biometric sensor 1002 may be detachable from the tactical gear 104 and placeable on an injured person 1000 nearby to the wearer 114 through an armband 1004 extendable from the biometric sensor 1002 when it is removed from the tactical gear 104. The biometric sensor 1002 may automatically store and/or communicate the biometric information 1006 of the injured person 1000 to a hospital 1008 when removed from the tactical gear 104 and placed on an arm of the patient, when the injured person 1000 is en route to the hospital 1008.

A single-chip Software-Defined Vision Sensor (SDVS) with integrated neuromorphic sensing and processing may deliver real time vision intelligence with privacy at source to the body worn safety device 100 to detect an obstacle and/or the ambient threat 112 in a path of the wearer 114 during low light conditions and trigger the haptic feedback device 106 when the obstacle and/or the ambient threat 112 is detected.

A spherical disc (e.g., a sentinel device 1100) may be wirelessly coupled with the body worn safety device 100 that is carryable and/or throwable by the wearer 114. The spherical disc (e.g., a sentinel device 1100) may automatically unfurl when it is thrown by the wearer 114 onto a level surface, such that a camera of the spherical disc is perpendicularly manifested and actively records when in the unfurled state 1100B. The haptic feedback device 106 on the body worn safety device 100 may vibrate when ambient threat 112 is visible to the camera of the spherical disc in the unfurled state 1100B.

A retainer 400A, 400B placed in a mouth of the wearer 114 may bookmark 402 a geospatial location based on an action in the mouth of the wearer 114 and/or to request help 404 to arrive at the geospatial location. The body worn safety device 100 may communicate without electronic signature through a non-radiative, human-body-centered communication network. The body worn safety device may include a taser 2302 integrated into the tactical gear 104 to automatically deliver an electric shock 2304 to an attacker 2306 who is physically wrestling with the wearer 114 when the artificial intelligence based threat detection model 108 detects a physical assault. The visual sensor 102 may be a thermal imaging sensor that detects heat signatures emitted by objects and converts them into visual data. An audiovisual data of the visual sensor 102 closest to the haptic feedback device 106 may be automatically stored in a combined memory and power module 110 for a configurable one of (1) a short period of time prior to the vibration of the haptic feedback device 106, (2) during the vibration of the haptic feedback device 106, and/or (3) another short period of time after the vibration of the haptic feedback device 106 stops vibrating.

In another embodiment, a body worn safety device 100 includes an array of visual sensors 200 around a torso 1900 of a wearer 114 such that ambient threats 112 around the wearer 114 are captured through an artificial intelligence based threat detection model 108, and an array of haptic feedback device 210 to vibrate at different locations of a body of the wearer 114 depending on a directional location of the ambient threat 112 using the artificial intelligence based threat detection model 108.

In yet another embodiment, a body worn safety device 100, includes a visual sensor 102 embedded in a center front area 212 of the tactical gear 104 such that the wearer 114 is able to sense the ambient threat 112 through the haptic feedback device 106 when the ambient threat 112 approaches from the front of the wearer 114 of the tactical gear 104. A language translator module 124 is integrated with center front area 212 through which the wearer 114 is able to bi-directionally communicate with an individual 606 in the ambient environment 600 using any language 602 other than a primary language 608 spoken by the wearer 114 when the language translator module 124 is activated. A haptic feedback device 106 integrated in the tactical gear 104 vibrates when the visual sensor 102 detects an ambient threat 112 to a wearer 114 of the tactical gear 104.

FIG. 1 is a platform view 150 designed for personnel engaged in security operations, according to one embodiment. Within FIG. 1, we observe the depiction of an individual, referred to herein as the "wearer" 114, who may represent various security personnel, including private security guards, police officers, or firefighters, tasked with safeguarding areas prone to potential threat, according to one embodiment. Notably, the wearer 114 may be outfitted with a tactical gear 104, specifically designed to be worn in hazardous environments, according to one embodiment.

The tactical gear 104 may be any wearable torso covering apparel designed for military and/or law enforcement purposes to enhance the efficiency, safety, and capability of the wearer 114 during operations, such as a tactical vest or a tactical carrier. Tactical gear 104, encompassing tactical vests, inner vests, and carriers, may include a wide range of equipment designed for military, law enforcement, and security personnel, and for civilian use in certain contexts like hunting, shooting sports, and outdoor activities. Tactical vest embodiments of tactical gear 104 may be designed to carry essential gear and provide quick access to ammunition, communications devices, and medical kits, and may have multiple pockets and pouches for organization, according to one embodiment. Tactical carrier embodiments of tactical gear 104 may be plate carriers specifically designed to hold ballistic armor plates for protection against bullets and shrapnel, and may also carry additional gear, according to one embodiment. Tactical gear 104 may also include body armor including bulletproof vests and/or other garments (worn inside a uniform or outside a uniform) designed to protect against ballistic threats. In one embodiment, tactical gear 104 may include ghillie suits and camo netting for blending into the environment during surveillance and/or hunting. In an alternative embodiment, the tactical gear may not have ballistic or bullet proof protection, but may be a simple garment having the various haptic and visual sensors described herein.

The visual sensor 102 may be a device integrated into a tactical gear 104 capable of detecting ambient threats 112 through visual inputs, functioning in various lighting conditions to enhance the wearer's situational awareness. Object recognition module 122 may be a computational unit within the system that analyzes visual data from the visual sensor 102 to identify objects and classify them, potentially as threats or non-threats. Threat detection model 108 may be one or more artificial intelligence algorithms designed to analyze inputs from the visual sensor 102 and/or other modules to identify potential threats in the environment surrounding the wearer 114. Compute module 118 may be the main processing unit that executes the software algorithms, including threat detection and object recognition, to analyze data collected by the system's sensors. Combined memory and power module 110 may be a unit that provides both power to the device's components and storage for data captured by the system, such as visual recordings and sensor data. The wearer 114 may be a person equipped with the tactical gear 104 that incorporates the body safety device, who benefits from enhanced situational awareness and threat detection.

The user authentication means 120 may be a security feature ensuring that the device's functionalities are accessible only by verified users, possibly through biometric verification or a digital passcode. GPS module 116 may be a component that offers geolocation capabilities, enabling the device to track the wearer's position and potentially record the locations of detected threats. Tactical vest 104 may be a wearable garment that houses the visual sensor 102, haptic feedback device 106, and other modules (e.g., object recognition module 122, compute module 118, a combined memory and power module 110, GPS module 116, a threat detection model 108, etc.), designed for use in security, military, or emergency response scenarios. In one embodiment, the tactical gear 104 having the sensor array may be a gear carrier in which a standard bullet proof gear can be inserted.

The distinguishing feature of this embodiment of FIG. 1 lies in the incorporation of an array of visual sensors 200, one of which is labeled as visual sensor 102, according to one embodiment. While FIG. 1 illustrates two visual sensors positioned on either shoulder area 1902, it is important to note that the tactical gear 104 may house multiple visual sensors 102 on both the front area 204 and back area 214 of the tactical gear 104, offering 360 degree surveillance capabilities, according to one embodiment. These visual sensors, akin to cameras, possess the ability to operate in low-light conditions, utilizing advanced visual processing capability technology or similar low-light detection mechanisms, according to one embodiment. Rather than principally recording video footage, their primary function is to detect ambient threats in the wearer's vicinity, according to one embodiment.

The term "ambient threats," referenced as number 112 in FIG. 1, encompasses various potential dangers, as depicted in FIG. 1, according to one embodiment. These threats include but are not limited to a fist (132A) attack, knife (132B), gunshots (132C), explosions (132D), fires (132E), a gun 132H, or even individuals running toward the wearer from obscure angles (132F), according to one embodiment. Upon the detection of such threats by the visual sensors 102, the corresponding haptic feedback device 106 embedded within the wearer's body activates, providing tactile feedback in the form of vibrations, according to one embodiment. While FIG. 1 illustrates the placement of haptic feedback device 106 primarily in the torso 1900 area, alternative configurations are feasible, allowing for adaptable sensor distribution across the wearer's body, according to one embodiment.

The connectivity between the visual sensors 200, haptic feedback device 210, and the combined memory and power module 110, as depicted in FIG. 1, may be concealed within the gear to ensure a streamlined design, according to one embodiment. Notably, the activation of haptic alerts, exemplified by haptic alert 500, may serve as the trigger for the gear to respond to detected threats, according to one embodiment. Moreover, the presence of the object recognition module 122 and the threat detection model 108, housed within the computational core (e.g., compute module 118), may serve as the operational brain of the device, according to one embodiment. In one embodiment, the compute module 118 is upgradable and is available in a number of potential configurations, according to one embodiment. Different versions of the compute module 118 may employ advanced algorithms to recognize one or more potential threats, such as pre-assaultive indicators, firearms or bladed weapons, opioid addiction, alcohol addiction, enhancing the wearer's situational awareness, according to one embodiment.

The combined memory and power module 110, a pivotal component of the system, may not only provide power to the device's electronics, including haptic feedback device 106 and computational modules but also features combined non-volatile memory for data storage when the combined memory and power module 110 is docked, according to one embodiment. This may enable the seamless uploading of critical information to a central server, facilitating post-incident analysis, according to one embodiment. Additionally, the module 110 may capture and store the wearer's GPS coordinates (e.g., using GPS module 116) during active duty, ensuring accurate documentation of deployment locations, according to one embodiment.

In operational terms, the system may remain dormant until the wearer 114 is dispatched to an active incident location 1406, conserving battery life, according to one embodiment. Upon activation, all computational modules and sensor arrays are initiated, remaining operational for the duration of the assignment, according to one embodiment. The threat detection module 108, an integral part of the system, may employ artificial intelligence algorithms trained to identify ambient threats 132 in the wearer's vicinity, enhancing the device's proactive threat detection capabilities, according to one embodiment.

In summary, FIG. 1 illustrates a comprehensive depiction of the innovative body-worn safety device 100, integrating advanced visual sensors 102, haptic feedback mechanisms (e.g., array of haptic feedback device 210), computational modules (e.g., compute module 112), and combined memory and power technology (e.g., using combined memory and power module 110) to enhance the safety and effectiveness of security personnel in challenging environments, according to one embodiment.

Figure 2:
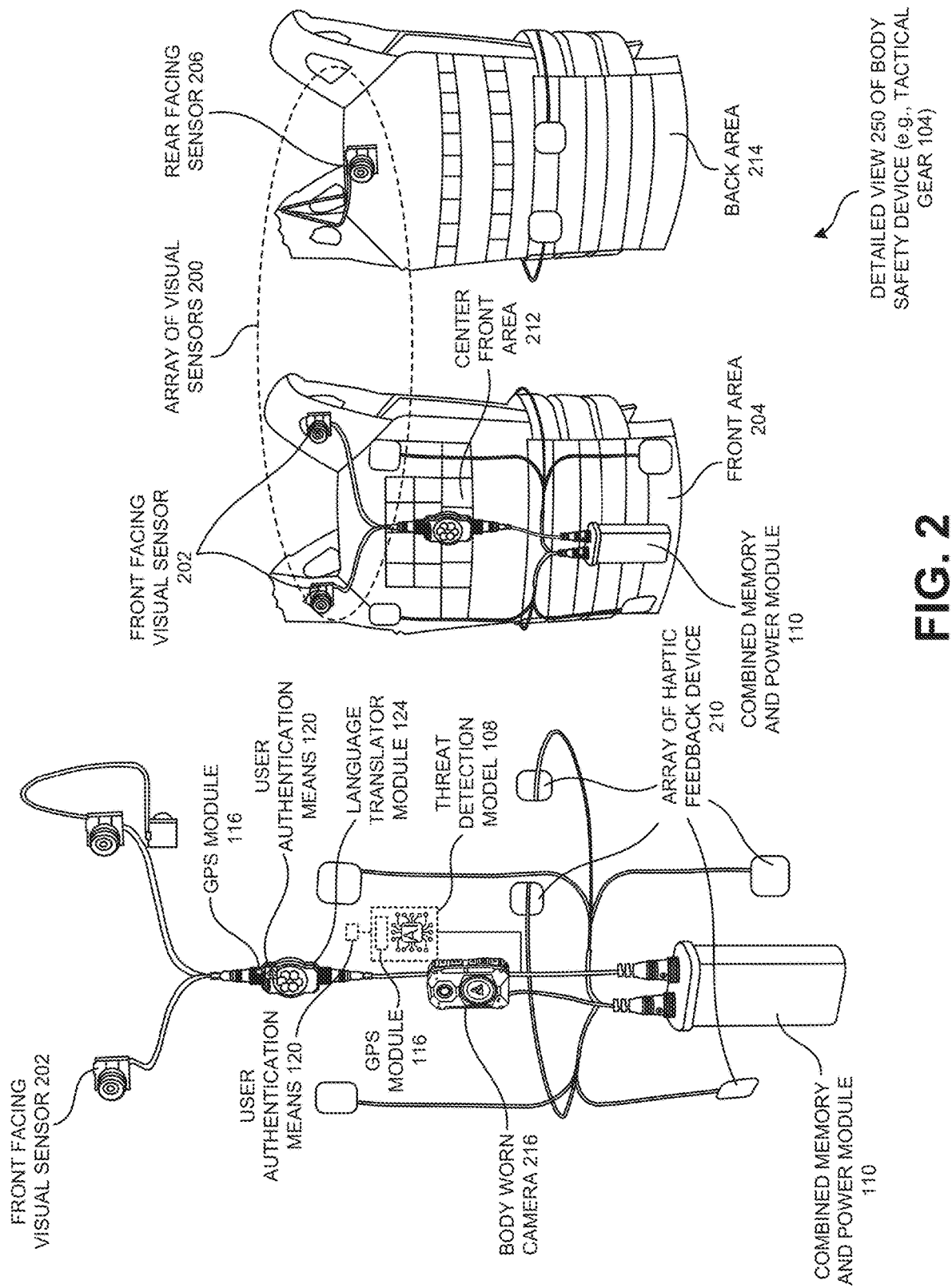
FIG. 2 is a detailed view of the body safety device of FIG. 1 illustrating an exemplary arrangement of its internal components, according to one embodiment.

FIG. 2 is a detailed view 250 of the body worn safety device 100 of FIG. 1 illustrating the arrangement of its internal components, according to one embodiment. Particularly, FIG. 2 builds on FIG. 1, and further adds, an array of visual sensors 200, a front-facing visual sensor 202, a front area 204, a rear facing sensor 206, an array of haptic feedback device 210, a center front 212, a back area 214, and a body worn camera 216, according to one embodiment.

The array of visual sensors 200 may be an assembly of a number of small, high-resolution cameras and/or sensors distributed strategically across the tactical gear 104. These sensors may be embedded within the fabric and/or attached to the gear's surface in a manner that optimizes the field of view and coverage area. Each sensor may be capable of capturing visual data in various spectrums, including visible light, infrared, and possibly thermal imaging to provide situational awareness in different environmental conditions. These sensors may be designed to cover a 360-degree field of view around the wearer, providing a comprehensive visual feed of the surrounding environment, according to one embodiment.

The sensors may be interconnected, likely through a secure, low-latency network that allows for real-time data processing and analysis. The AI component of the threat detection model 108 can be crucial for interpreting the vast amounts of visual data collected by the array of visual sensors 200. The threat detection model 108 may utilize machine learning algorithms to identify and categorize objects, detect motion, recognize faces and/or behavioral patterns to assess potential threats automatically, according to one embodiment.

The AI system of the threat detection model 108 may process the visual data in real-time, using advanced algorithms for object recognition using the object recognition module 122, threat assessment, and situational awareness. It may highlight points of interest, identify known individuals 606 and/or objects, and flag potential hazards. The threat detection model 108 may be trained to recognize specific patterns, uniforms, weapons, and even behavioral cues that might indicate a threat to the wearer 114, according to one embodiment.

The threat detection model 108 might also be designed to adapt and learn from new situations, improving its accuracy and response over time. It may provide the wearer 114 with actionable insights through a heads-up display (HUD) and/or other augmented reality (AR) interfaces, haptic feedback (e.g., haptic alert 500 using the haptic feedback device 106 and threat detection model 106), and/or audio alerts. Moreover, the threat detection model 108 of the compute module 118 may be programmed to work collaboratively with other systems within the tactical gear 104, such as communication arrays, navigation tools (e.g., using the GPS module 116), and health monitoring devices, to provide a comprehensive, integrated operational platform for the wearer 114, according to one embodiment.

This advanced integration of visual sensors and AI may not only enhance the situational awareness and response capabilities of the wearer 114 but can also contribute to team-level strategies and tactics by sharing processed information across a networked battlefield or operational environment. The front-facing visual sensor 202 may be an electronic device that detects and responds to a stimulus from the physical environment in its surrounding. The front-facing visual sensor 202 may be a sophisticated component integrated within the front area 204 of the tactical gear 104 designed for real-time data acquisition and processing to assist the wearer 114 in identifying and reacting to threats and other important environmental cues, according to one embodiment.

The front-facing visual sensor 202 may include an advanced camera capable of capturing high-definition video in a range of lighting conditions, from bright daylight to low-light scenarios. It may also possess infrared capabilities for night vision, allowing the wearer 114 to see in the dark. In addition, the front-facing visual sensor 202 may include thermal imaging to detect heat signatures, which can be especially useful for identifying living targets at night and/or through obstructions like smoke or foliage, according to one embodiment.

The AI component of the front-facing visual sensor 202 may be responsible for analyzing the visual feed. It can use machine learning algorithms to perform tasks such as facial recognition, uniform and insignia identification, object detection, and even behavioral analysis to assess potential threats. For example, the AI of the front-facing visual sensor 202 might be trained to recognize the subtle movements that precede an aggressive action, allowing for preemptive response, according to one embodiment.

The AI component of the front-facing visual sensor 202 may also have a decision-making capability to prioritize and alert the wearer 114 to the most immediate threats through auditory, visual, or haptic feedback. This can be conveyed through an earpiece, a visual display inside a helmet, or vibrations in specific areas of the threat detection model 108 to indicate the direction of a threat. Integration with other systems can include network connectivity to share real-time data with team members or command centers, GPS module 116 for location tracking, and databases for cross-referencing individuals and/or objects detected by the sensor, according to one embodiment.

Durability and discretion may be the key design aspects of the array of visual sensors 200, ensuring that it is robust enough to withstand the rigors of field operations while being inconspicuous enough not to draw attention or hinder the wearer's mobility. Its placement on the tactical gear 104 may be strategic to maximize field of view while minimizing blind spots, ensuring comprehensive coverage of the area in front of the wearer 114, according to one embodiment.

The front area 204 may be an anterior portion of the tactical gear 104 on which the front-facing visual sensor 202 are installed such that it is capable of capturing visual data covering a 360-degree field of view around the wearer 114, providing a comprehensive visual feed of the surrounding environment, according to one embodiment.

Analogous to the front-facing visual sensor 202, the rear-facing sensor 206 may be an electronic device that detects and responds to a stimulus from the physical environment in its surroundings in the rear of the wearer 114 of the tactical gear 104. The rear-facing sensor 206 may be integrated within the back area 214 of the tactical gear 104 designed for real-time data acquisition and processing to assist the wearer 114 in identifying and reacting to threats and other important environmental cues, according to one embodiment.

The array of haptic feedback device 210 may constitute a network of tactile feedback devices designed to communicate information through the sense of touch. Here's an outline of a system of array of haptic feedback device 210 of the tactical gear 104 may include:

Placement and Integration: The array of haptic feedback device 210 may be distributed across the tactical gear 104 in key locations, such as over the shoulders, back, and sides primarily in the torso area of the wearer 114. The sensors may be embedded into the fabric of the tactical gear 104 and/or attached to the inner lining to maintain comfort and mobility, according to one embodiment.

Functionality: Each sensor in the array of haptic feedback device 210 may be capable of producing different types of tactile feedback, such as vibrations, pressure, and/or temperature changes. This feedback can inform the wearer 114 of various conditions and alerts without relying on visual or auditory cues, which is critical in stealth and/or high-noise environments, according to one embodiment.

AI Processing: The array of haptic feedback device 210 may be connected to the threat detection model 108 of the compute module 118 incorporated directly into the gear. This unit may receive input from various data sources, such as visual or auditory sensors, GPS, and/or other monitoring devices. The threat detection model 108 may analyze this data to detect threats, navigate terrain, and/or relay tactical information, according to one embodiment.

Communication Through Tactile Signals: Based on the threat detection model's 108 analysis, the compute module 118 may send signals to the array of haptic feedback device 210 to deliver specific patterns of tactile feedback. For example, a pulsing vibration on the left side may indicate an approaching threat from that direction, while a steady pressure on the back might signal the wearer to halt. The threat detection model 108 may use different rhythms, intensities, or durations of feedback to convey different messages or levels of urgency, according to one embodiment.

Adaptive Learning: The threat detection model 108 of the compute module 118 may be capable of learning from the wearer's responses and the environment to optimize the haptic feedback. For instance, if the wearer 114 consistently reacts more quickly to certain types of vibrations, the AI may prioritize those for urgent alerts, according to one embodiment.

Interactivity: The tactical gear 104 may also allow the wearer 114 to communicate back to the AI through touch, perhaps by tapping certain areas of the gear to confirm receipt of a message or to request specific information, according to one embodiment.

Power Efficiency and Durability: Given the potential for extended field use, the array of haptic feedback device 210 and AI system may be designed for low power consumption and high durability. They may be powered by advanced, long-lasting combined memory and power module 110 batteries integrated within the tactical gear 104, according to one embodiment.

User Customization: The system may allow for user customization and authentication using the user authentication means 120, enabling each wearer 114 to adjust the intensity, location, and type of haptic feedback according to personal preference and mission requirements. Overall, this AI-driven array of haptic feedback device 210 may enhance the situational awareness and survivability of the wearer 114 by providing an intuitive, non-disruptive means of receiving critical information, according to one embodiment.

The body worn camera 216 (e.g., Axon® Body 4 body worn camera) may be an electronic device for recording visual images in the form of photographs, film, and/or video signals for both real-time analysis and after-action review. The body worn camera 216 may be integrated within the center front 212 area of the tactical gear 104. The body worn camera 216 may have a wide-angle lens to capture a broad field of view. In a preferred embodiment, the body worn camera 216 may work along with the body worn safety device 100. While the body worn safety device 100 focuses on real time threat detection in one embodiment, the body worn camera 216 may focus on storage for later review.

Given the various environments that tactical operations may encounter, the body worn safety device 100 may be equipped with low-light capabilities for low-light adaptability. The body worn safety device 100 may utilize night vision and/or thermal imaging technologies to maintain visibility in near-darkness and/or through obscurants like smoke. To ensure that the sensor feed is clear even when the wearer 114 is in motion, the body worn safety device 100 may have advanced image stabilization technology for each of its visual sensors 102, according to one embodiment.

The AI system within the body worn safety device 100 may be capable of running complex algorithms for facial recognition, license plate reading, and/or detecting specific patterns of behavior that may indicate a threat. It may also tag and categorize different elements within the video for easy retrieval. The body worn safety device 100 may be able to stream footage to a command center and/or other team members, allowing for coordinated responses and situational awareness sharing. This streaming can be done over encrypted channels to ensure operational security, according to one embodiment.

Footage data may be stored in a secure, encrypted format, with the ability to upload data to a cloud server and/or local storage depending on the operational needs and security protocols. The body worn safety device 100 may be ruggedized to withstand impacts, water, dust, and other environmental factors typically encountered in field operations, according to one embodiment.

While the visual sensors 102 of the body worn safety device 100 may autonomously record based on certain triggers or AI detections, the wearer 114 can also have the ability to manually activate or deactivate recording as necessary. The body worn safety device 100 may be integrated with the array of sensors 200 and systems on the tactical gear 104, such as GPS module 116 for geotagging footage, biometric sensors for monitoring the wearer's vitals, and array of haptic feedback device 210 for alerting the wearer 114 to specific AI detections.

Since the body worn safety device 100 may be worn and used potentially over long periods, it may be designed to be power-efficient, with a battery life suitable for extended missions and the ability to be recharged using the combined memory and power module 110 of the the tactical gear 104 or have its recharged in the docking station 702. This body worn safety device 100 may serve as a proactive tool to enhance the operational capabilities and safety of the wearer 114 through its AI-driven insights and connectivity, according to one embodiment.

Figure 3:
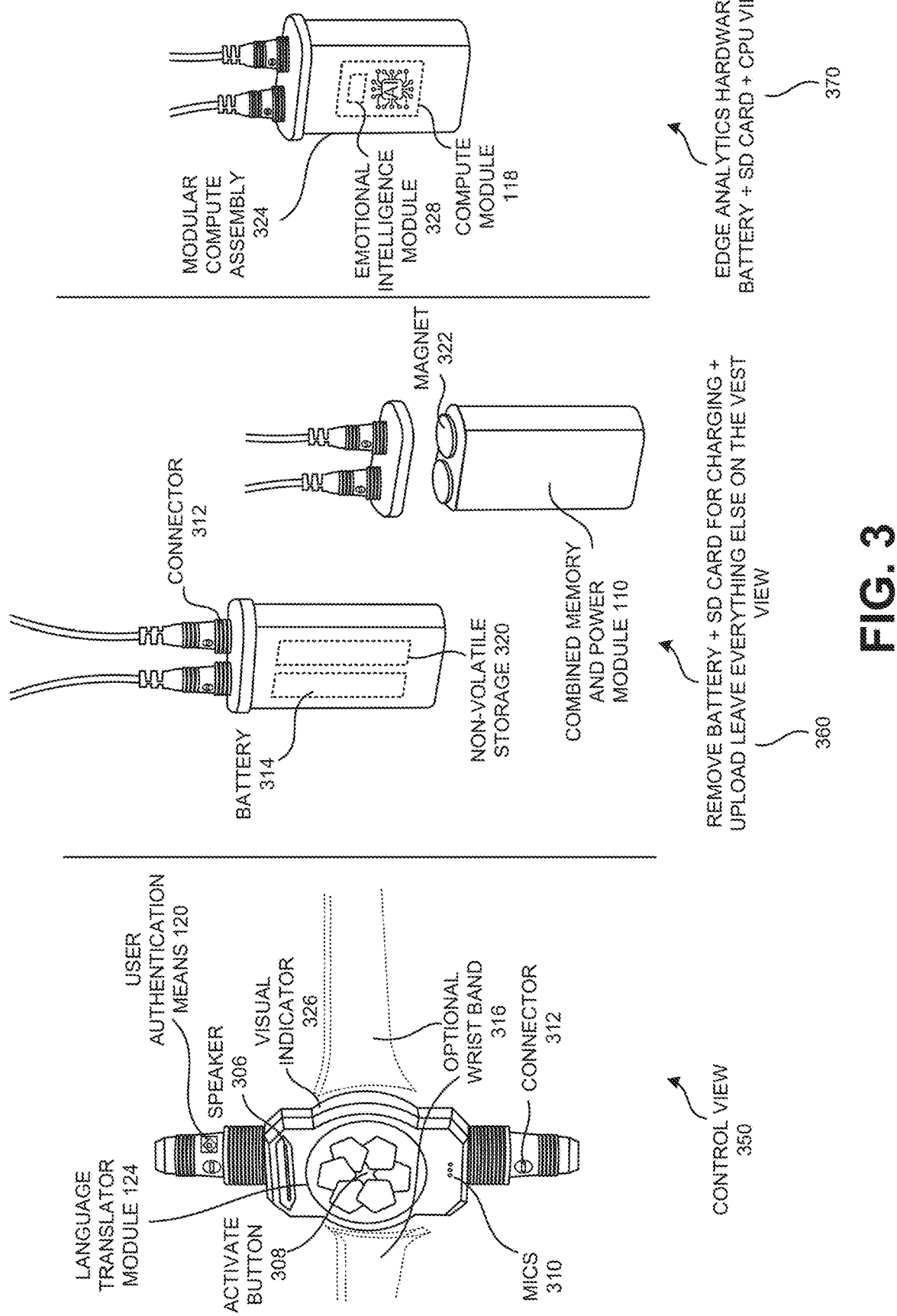
FIG. 3 is a control view of the tactical gear of FIG. 1 illustrating the various components of the language translator module and the combined memory and power module of the body worn safety device, according to one embodiment.

FIG. 3 is a control view 350 of the tactical gear 104 of FIG. 1 illustrating the various components of the language translator module 124 and the combined memory and power module 110 of the tactical gear 104, according to one embodiment. Particularly, FIG. 3 builds on FIGS. 1 and 2, and further describes the language translator module 124, and adds the compute module 118, a speaker 306, a activate button 308, a mics 310, a connector 312, a battery 314, an optional wrist band 316, a non-volatile storage 320, a magnet 322, an modular compute assembly 324, and a visual indicator 326, according to one embodiment.

The language translator module 124 may be an instrument installed within the tactical gear 104 The language translator module 124 system may be designed for hands-free operation, with the possibility of voice control (considering the presence of multiple microphones) and a visual interface for interaction. The AI capabilities within the language translator module 124 system may be used for real-time communication in any language of the world, according to one embodiment. The integration of user authentication means 120 implies a high level of security and personalization for the tactical gear 104, according to one embodiment.

The compute module 118 may be the brain of the system, which can house the AI processor, data storage, and software needed to operate the language translator module 124 and the haptic feedback device 106, analyze data, and communicate with other devices. The compute module 118 may serve as the central hub for operation, data processing, and interaction for the body worn safety device 100. The compute module 118 may house the processors necessary for running AI algorithms. These may analyze the video feed in real-time, identify objects and/or individuals, flag threats, and even process voice commands through the integrated microphones (e.g., using mics 310). AI in the compute module 118 may be leveraged for advanced tasks like facial recognition, behavior prediction, and situation assessment, according to one embodiment.

The user authentication means 120 may be a security mechanism to ensure that only authorized users can access and operate the body worn safety device 100. This can involve biometric verification, such as fingerprint or voice recognition, or a secure digital keycard system, according to one embodiment.

The speaker 306 may be an output device for audio feedback, alerts, and/or communication. The speaker 306 may provide auditory feedback and/or allow for two-way communication, possibly with a command center and/or other team members, according to one embodiment.

The visual indicator 326 may light up when the translation is occurring, and when activate button 308 is pressed by the wearer 114 to start translation. The visual indicator 326 may display information from the AI analysis, such as identified threats, navigation data, or operational status of the camera, according to one embodiment.

The activate button 308 may be a manual control to start and/or stop real time language translation in any language. The mics 310 may be a transducer that converts sound into an electrical signal. The mics 310 may be microphones for audio capture, which can be used to record surrounding sounds and/or for voice command recognition, according to one embodiment.

The optional wrist band 316 may be a strip of material worn around the wrist. The optional wrist band 316 may allow the language translation module 124 to be attached to a wristband on a patient in the field, and may transform the language translation module 124 into a biometric reader of vital signals of the patient, through sensors on the underside of the language translation module 124, according to one embodiment.

The combined memory and power module 110 may be a unit that combines both memory and battery functionality, which charges and uploads data when docked. The combined memory and power module 110 may encapsulate the dual functionality of the device-providing power and storing data, with the added capability of data transfer upon connection to a docking station 702 and/or a host device. The combined memory and power module 110 may combine several functionalities that are typically found separately in traditional devices. The connector 312 may be an element used to connect a body worn camera 216 and/or the combined memory and power module 110 to the language translation module 124, according to one embodiment.

The combined memory and power module 110 may be the main unit that houses both the energy storage components and the data storage hardware. The combined memory and power module 110 may be compact and rugged to withstand the wear and tear of field operations. The combined memory and power module 110 may use a modular design for easy insertion and removal from the tactical gear 104 for maintenance, charging, or data transfer, according to one embodiment.

The combined memory and power module 110 may include a high-capacity rechargeable battery, possibly utilizing lithium-ion technology, such as the 21700 battery cells, known for their optimal balance of power density and longevity. The energy stored may be used to power the gear's electronics, including communication devices, sensors, and the processing unit for the AI. The design may incorporate features for power management, such as voltage regulation and power distribution to various tactical gear 104 components, according to one embodiment.

The combined memory and power module 110 may have magnet connectors 322 to interface with the gear's systems, enabling both power and data flow. The magnetic connectors 322 may be used for ease of attachment and removal, providing a secure connection that's also quick to detach when necessary, according to one embodiment.

The AI system of the tactical gear 104 may rely on the combined memory and power module 110 to store algorithms, learned data, and operational logs. The AI may also manage power consumption, optimizing the battery life by adjusting the power supply based on the gear's operational state and demand, according to one embodiment.

Indicators for power levels and memory capacity may be part of the combined memory and power module 110, giving the wearer 114 real-time status updates. The combined memory and power module 110 may be designed to alert the wearer 114 when power is low and/or when memory capacity is nearing its limit. The combined memory and power module 110 may be designed for field conditions, allowing users to replace or recharge batteries and transfer data without specialized equipment. It may also support secure data encryption to protect sensitive information stored on the device, according to one embodiment.

According to one embodiment, the wearer 114 may be able to rely on the combined memory and power module 110 to power the gear's essential functions over an extended period while securely capturing and storing valuable data generated by the gear's sensors and AI analysis. The integration of both power and memory into a single module may simplify the system's complexity, reducing weight and conserving space, which is critical in tactical situations, according to one embodiment.

The combined memory and power module 110 may provide the electrical power necessary for the gear's electronics and AI components. A rechargeable battery 314 may be housed within the combined memory and power module 110. Non-volatile storage 320 may be a memory unit capable of retaining data without the need for power, likely used for storing important data such as transcripts generated by the AI, and optionally video feeds, gps data, maps, mission details, or AI analytical data. Non-volatile storage 320 may ensure that data, like mission parameters, surveillance footage, and AI processing information, is preserved without a continuous power supply. The storage might be solid-state in nature (akin to an SD card and/or built-in flash memory) to offer fast data access speeds and reliability, according to one embodiment.

The connector 312 may be an interface for connecting the combined memory and power module 110 to other parts of the gear and/or external devices. The wires leading from the connector 312 may be used for power distribution and data transfer. The battery 314 may be a specific type of battery cell, known for their high energy density, indicating the module uses two of these cells, according to one embodiment.

The magnet 322 may be an object and/or a component capable of magnetically attaching the combined memory and power module 110 to the tactical gear 104. The magnetic attachment mechanism of the magnet 322 may allow for easy removal and attachment of the combined memory and power module 110 to the tactical gear 104, according to one embodiment.

In an exemplary embodiment, the "Remove Battery+SD Card for Charging+Upload Leave Everything Else on The Vest View 360" illustrates that the battery and a possible SD card (not explicitly depicted but commonly used for memory storage) may be detached from the tactical gear 104 for recharging and data transfer. This design may enable the wearer 114 to maintain the tactical gear 104 in a ready state while the power and memory components are being refreshed and/or data is being uploaded, likely contributing to operational efficiency and ease of maintenance, according to one embodiment.

The modular compute assembly 324 may be a detachable computing unit with customizable AI processing power tailored to specific sensors and needs, which houses the compute module 118. The modular compute assembly 324 may be the processing unit of the system, where the computational tasks occur, including running AI algorithms. The modular compute assembly 324 may be flexible and modular in nature, allowing for adjustments in processing capabilities based on the requirements of different sensors and applications. Such a device may enable users to swap, replace, and/or upgrade AI processing components to match specific computational needs, making it highly adaptable for various use cases, from robotics to smart home devices, according to one embodiment.

According to one embodiment, as shown in Edge Analytics Hardware Battery+SD Card+CPU View 370, the modular compute assembly 324 may include a CPU (Central Processing Unit), battery, and SD card within it. The "edge analytics hardware" capability of the modular compute assembly 324 may allow processing data at the edge of the network. The modular compute assembly 324 may perform real-time data analysis locally without needing to send data back to a central system. This local processing is crucial for rapid decision-making in the field, according to one embodiment.

The overall design of the modular compute assembly 324 may be a self-contained unit that may handle the demands of processing and storage with the added capability of working in a decentralized manner, providing on-the-spot analytics and insights powered by AI. The modular compute assembly 324 may be designed for quick deployment and ease of use in a tactical environment, where reliability and efficiency are paramount. FIG. 3 also illustrates an emotional intelligence module 328, which may detect and analyze human emotions of individuals in an ambient area to the wearer 114 using computer vision and auditory sensing to detect the presence or absence of an ambient threat 112, according to one embodiment.

Figure 4:
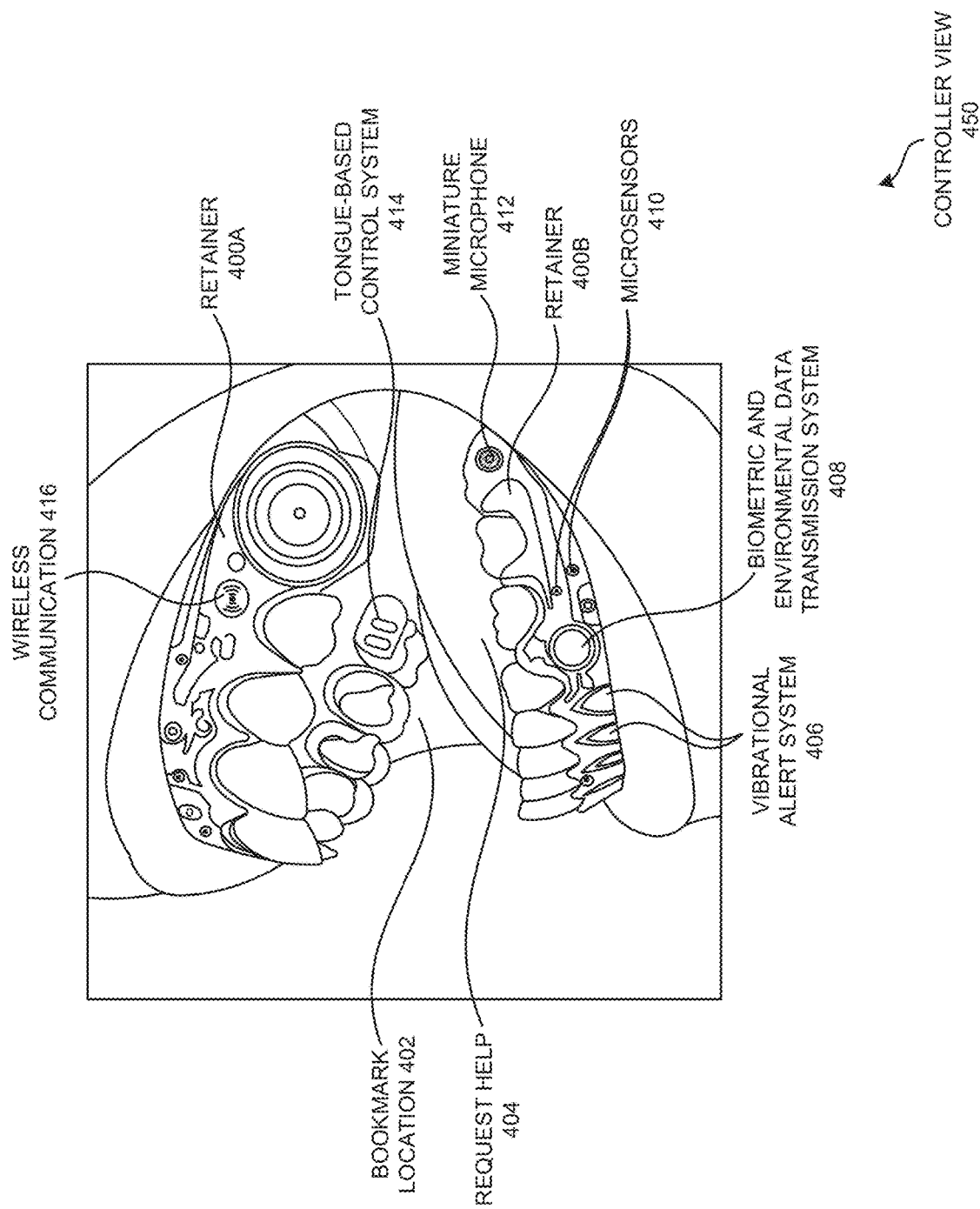
FIG. 4 is a controller view of a retainer that can perform commands such as bookmark a location or request help to ambient threat using an artificial intelligence based threat detection model of FIG. 1, according to one embodiment.
Figure 11:
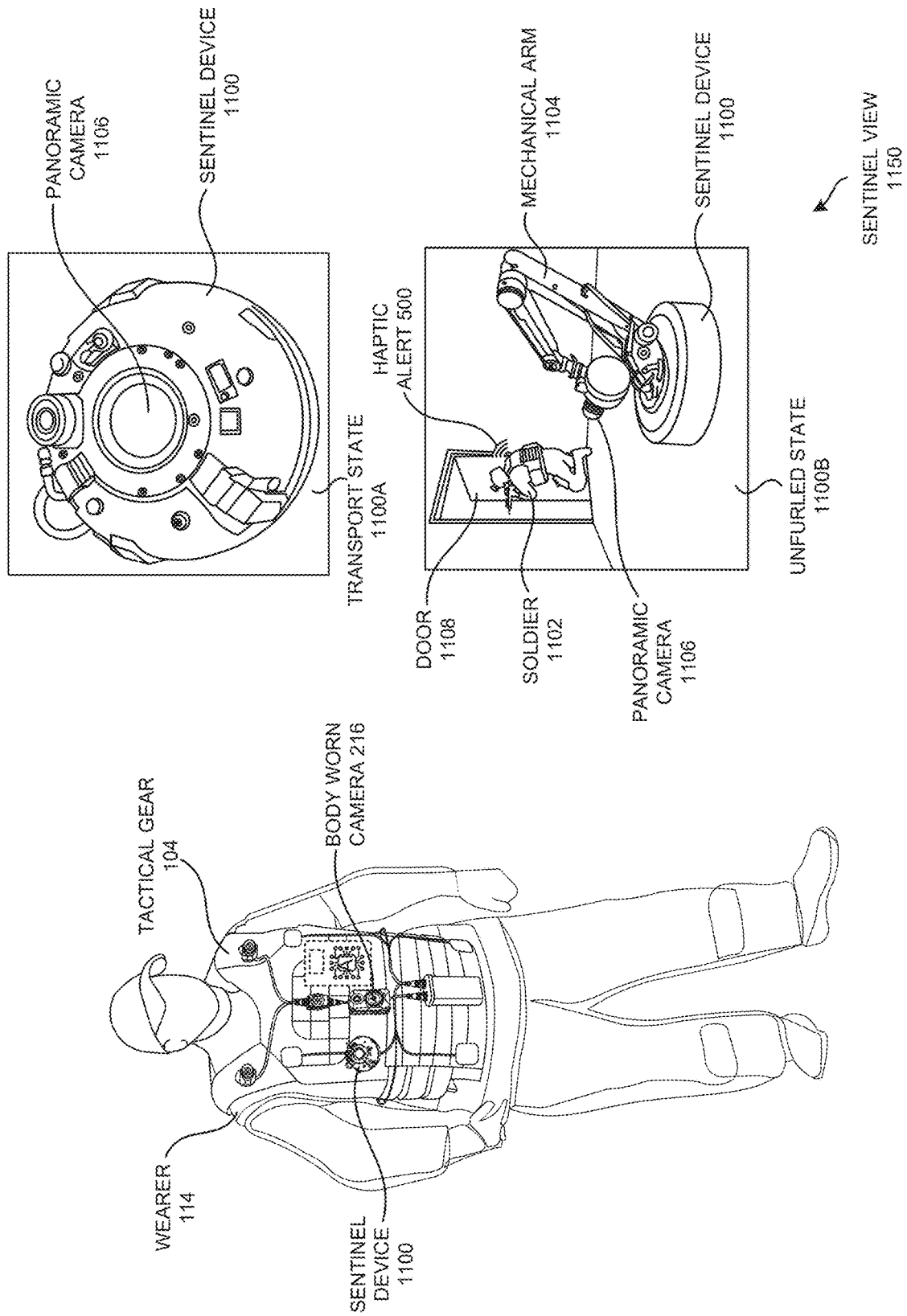
FIG. 11 is a sentinel view illustrating a sentinel device integrated within the tactical gear system of FIG. 1 to alert a security personnel to movements and/or threats detected at potential entry and/or breaching points of a building, according to one embodiment.

FIG. 4 is a controller view 450 using an advanced oral device of a retainer 400 that can perform commands such as bookmark a location 402 and/or request help 404 while the body worn safety device 100 is used in high threat situations such as the one shown in FIG. 11, according to one embodiment. In such a system, the sentinel device 1100 may be detonated through the retainer 400 by a wearer 114 having the retainer 400 in their mouth.

According to one embodiment, the body worn safety device 100 of FIG. 1 may be designed as an advanced oral device of a retainer 400A and 400B as shown in FIG. 4. The retainer 400A, 400B may be designed to function as both a threat sensor and control interface for a generative AI wearable system that can perform commands such as bookmark a location 402 and/or request help 404, according to one embodiment.

The advanced oral device of the retainer 400A, 400B may be designed to customizably fit comfortably inside the user's mouth, similar to dental retainers. The retainer 400A and 400B may be crafted from durable, biocompatible materials resistant to moisture and wear. The ergonomic design of the retainer 400A, 400B may ensure comfortable, extended wear for the user (e.g., wearer 114) without interfering with speech and/or breathing, according to one embodiment.

According to one embodiment, a general interpretation of the elements typically involved in such a device is described below:

The advanced oral device of the retainer 400A, 400B may utilize a bone conduction technology for discreet alerts transmitted to the inner ear of the wearer 114. The bone conduction technology may be a part of the vibrational alert system 406 which can transmit sound vibrations directly to the inner ear, bypassing the eardrum of the wearer 114, according to one embodiment.

The upper retainer 400A and the lower retainer 400B may include embedded microsensors 410 for analyzing voice patterns and detecting environmental changes. These small sensors may be dispersed throughout the device and might be the small, numerous dots and/or nodes. The microsensors 410 may be designed to analyze voice patterns and detect environmental changes, according to one embodiment.

The retainer 400 may include a tongue-based control system 414 to detect every movement and gesture of the wearer's tongue in real-time to support a sensitive inner surface for tongue movement-based commands. The tongue-based control system 414 may be a touch-sensitive area on the inner surface of the device that responds to the tongue's movements, allowing the wearer 114 to issue commands without speaking, according to one embodiment. The retainer 400 may be placed in a mouth of the wearer to bookmark a geospatial location based on an action in the mouth of wearer 114, and/or request help to arrive at the geospatial location.

The miniature microphones 412 may be integrated into the device to pick up whispered and/or subvocalized commands for hands-free operations. They can be the small, grille-like features that can function as an input for voice commands. The retainer 400 may have a wireless communication 416 to allow for secure connectivity with external AI systems via Bluetooth and/or another wireless communication standard, according to one embodiment.

The retainer 400A, 400B may include the biometric and environmental data transmission system 408 for real-time data sharing to enhance situational awareness. The biometric and environmental data transmission system 408 may utilize microsensors 410 to monitor physiological and environmental data. The various nodes and microsensors 410 may serve the purpose of collecting and transmitting real-time data to enhance situational awareness. The biometric and environmental data transmission system 408 may include subvocal communication to allow silent communication through throat and mouth movement detection, according to one embodiment.

The retainer 400A, 400B may support wireless charging. The retainer 400A, 400B may have specialized features for tactical environments, such as a tactical command table. This may be a machine learned pattern of the tongue that can move or press against to issue specific commands. For example, the wearer 114 may request help 404 by moving their tongue in a specific pattern to issue specific commands. A notification may be generated by the biometric and environmental data transmission system 408 based on a non-natural movement of the tough (e..g, must be intentional to prevent false positives) by the wearer 114 and may be sent to the command center for requisite action, according to one embodiment.

The microsensors 410 of the retainer 400A, 400B may enable health monitoring of the wearer 114 by assessing vital signs. The retainer 400A, 400B may have proximity alerts integrated with the microsensors and the AI system to analyze data and provide alerts, according to one embodiment.

Figure 5:
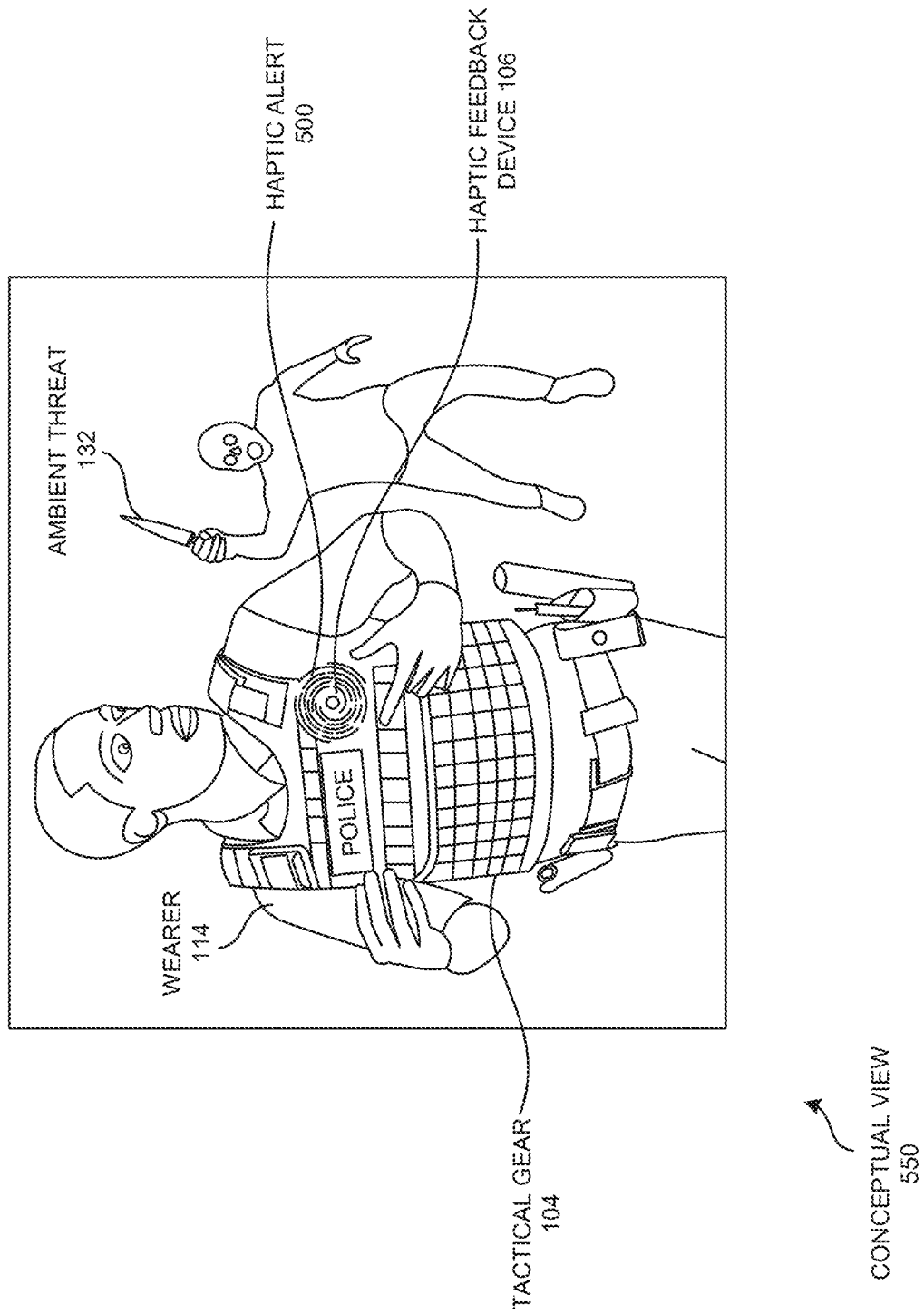
FIG. 5 is a conceptual view of the body safety device of FIG. 1 illustrating the tactical gear worn by a law enforcement personnel during a hostile situation, according to one embodiment.

FIG. 5 is a conceptual view 550 of the body worn safety device 100 of FIG. 1 illustrating the tactical gear 104 worn by a law enforcement personnel during a hostile situation, according to one embodiment. As described in various embodiments of FIG. 1-4, the tactical gear 104 worn by law enforcement personnel shown in FIG. 5 may be integrated with advanced visual sensors (e.g., array of visual sensors 202), haptic feedback mechanisms (e.g., using array of haptic feedback device 210), computational modules (e.g., threat detection model 108, compute module 118), and combined memory and power technology (e.g., combined memory and power module 110) to enhance the safety and effectiveness of security personnel in challenging environments, according to one embodiment.

As shown in FIG. 5, the tactical gear 104 may be equipped with a haptic feedback device 106, which includes capabilities to sense various forms of threats, such as sharp objects, firearms, and/or other potential weapons. The object recognition module 122 may analyze data from these sensors to determine the presence of the ambient threat 132 such as a gun, knife, bomb and/or weapon. The object recognition module 122 may analyze data from these sensors to determine the presence of the ambient threat 132 such as a gun, knife, bomb and/or weapon. Upon detecting a potential ambient threat 132, the system may use AI to quickly assess the level of danger and the appropriate response. The system may then send a haptic alert 500 to the wearer 114. This alert may be a vibration and/or other tactile signals that inform the wearer 114 of the direction and proximity of the threat without requiring them to look at a display and/or listen to audio cues, which may be critical when visual or auditory senses are already overloaded due to loud, chaotic, and/or low-visibility environment. By providing immediate physical feedback, the tactical gear 104 may enhance the wearer's situational awareness, enabling them to react quickly to the threat. The threat detection model 108 may assist in decision-making by recommending actions based on the type of detected threat and previous training data. For instance, the GPS module 116 integrated within the tactical gear 104 may direct the wearer 114 to a safe route in the proximity of the anticipated hostile attack. The threat detection model 108 may further suggest taking cover to a nearby refuge, drawing a weapon, and/or using non-lethal force, depending on the situation. Furthermore, the system might record data about encountered threats, which may be used for later analysis, training, or legal purposes. In addition, the tactical gear 104 may also be linked to a communication system to ensure constant connectivity with command centers, database 706, and other team members (e.g., land vehicle 804) for real-time intelligence and coordination, according to one embodiment.

Figure 6:
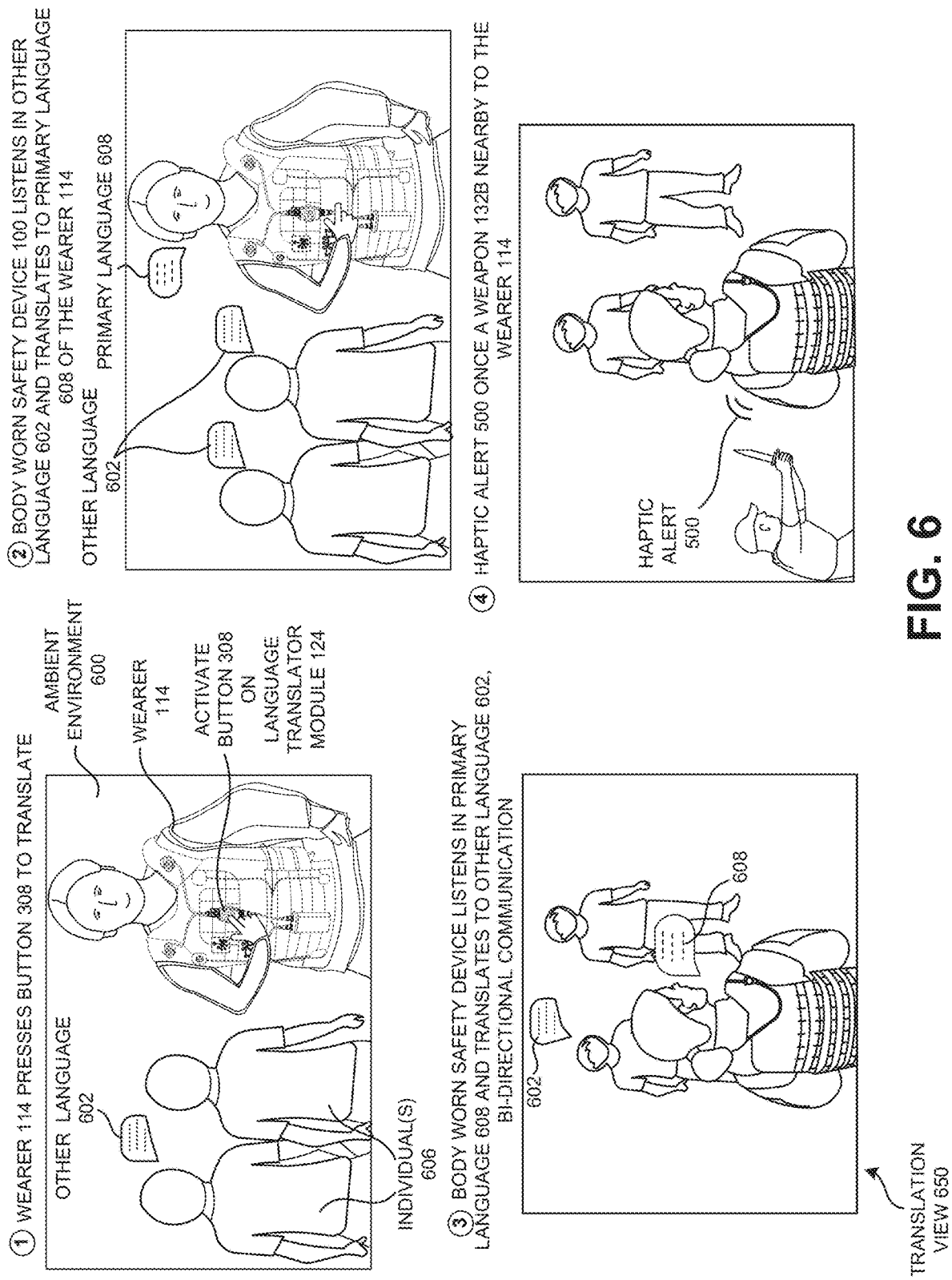
FIG. 6 is a translation view illustrating a bi-directional communication of a wearer of the body safety device of FIG. 1 illustrating communication with a group of individuals in an ambient environment using any language other than a primary language spoken by the wearer when the language translator module is activated by the wearer, according to one embodiment.

FIG. 6 is a translation view 650 illustrating a process flow of bi-directional communication with a group of individuals 606 by the wearer 114 of the body safety device 100 of FIG. 1. Particularly, FIG. 6 illustrates the communication with a group of individuals 606 in an ambient environment 600 using any other language 602 other than a primary language 608 spoken by the wearer 114 when the language translator module 124 is activated by the wearer 114. As shown in circle "1", two individual(s) 606 may speak in other languages 602 with the wearer 114 in an ambient environment 600. As the other language 602 is not understood by the wearer 114, it may activate the language translator module 124 using the activate button 308 on the tactical gear 104 he or she is wearing. In circle "2" of FIG. 6, upon activation, the language translator module 124 may listen to the other language 602 spoken by the individual(s) 606 and translates it to the primary language 608 of the wearer 114. In circle "3", the language translator module 124 may listen to the primary language 608 and translate it to the other language 602 enabling a bidirectional communication between the wearer and the individual(s) 606 in the ambient environment 600. In circle "4", while the wearer 114 is speaking with the individual(s) 606 in mitigating the hostile situation, the object detection module 122 of the tactical gear 104 may detect an ambient threat 112 from behind and trigger the haptic feedback device 106 to send a haptic alert 500 to the wearer 114 to make him/her aware of a threat approaching from its back, according to one embodiment.

Figure 7:
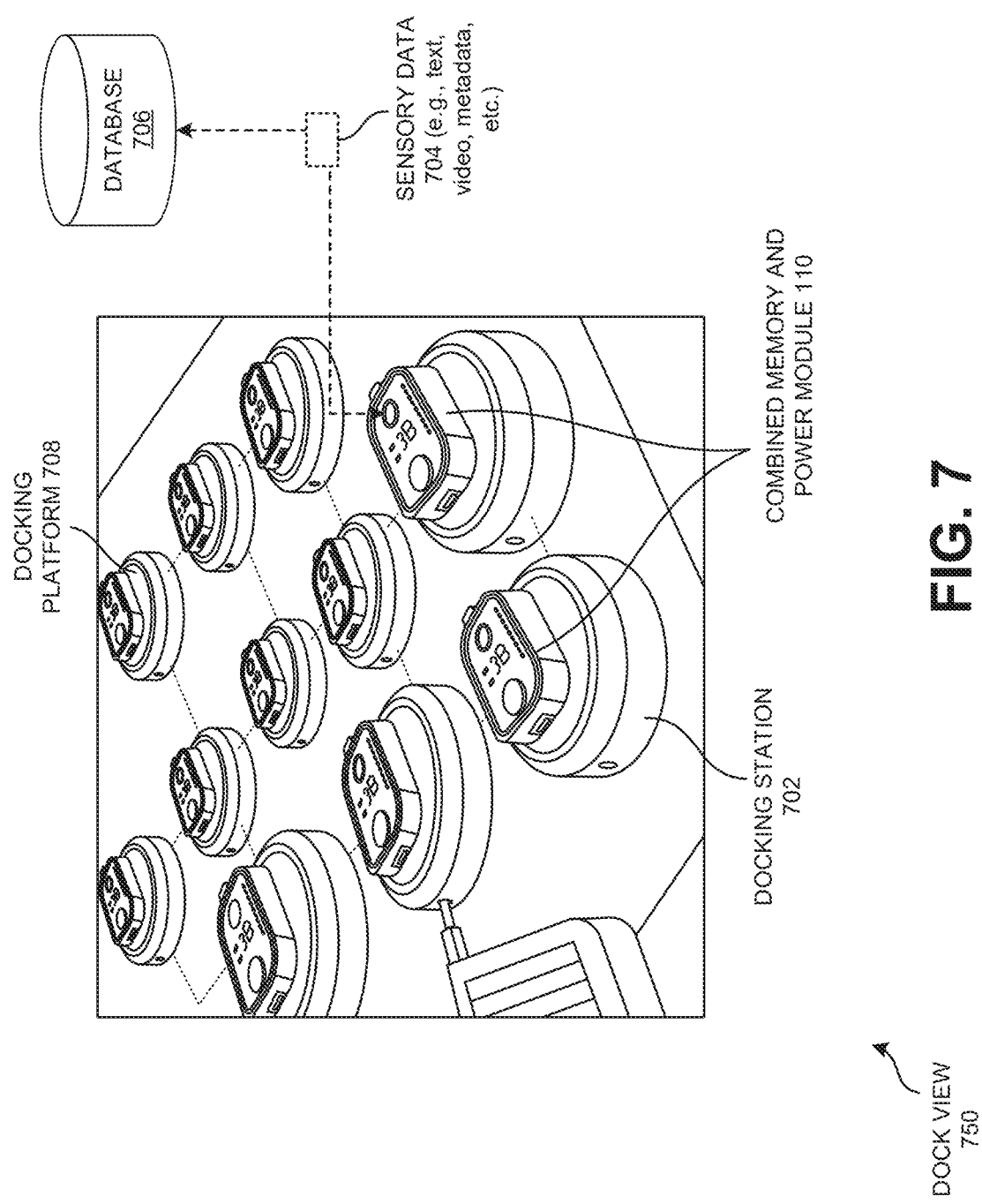
FIG. 7 is a dock view of the body safety device of FIG. 1 illustrating the automatic download of the sensory data captured from the visual sensor and the haptic feedback device when the combined memory and power module is docked in a docking station, according to one embodiment.

FIG. 7 is a dock view 750 of the body safety device of FIG. 1 illustrating the automatic download of the sensory data 704 captured from the visual sensor 102 and the haptic feedback device 106 when the combined memory and power module 110 is docked in a docking station 702, according to one embodiment.

As shown in the figure, the combined memory and power module 110 may be removable from the tactical gear 104. The docking station 702 may be a designated area with multiple docking platform(s) 708 for charging the combined memory and power module 110. The docking station 702 may provide a simplified way to plug-in and/or dock the combined memory and power module 110 for charging. The combined memory and power module 110 may power the visual sensor 102 and/or the haptic feedback device 106 of the tactical gear 104. The combined memory and power module 110 may include a memory storage which auto-downloads the sensory data 704 (e.g., text data, video data, metadata, etc.) captured from the visual sensor 102 and the haptic feedback device 106 when the combined memory and power module 110 is docked in a docking station 702. The combined memory and power module 110 may simultaneously charge multiple devices on the wearer 114 including a mobile phone, a body worn camera 216, and/or the visual sensor 102 during on-site operation, according to one embodiment.

The docking station 702 may enable the seamless uploading of critical information to a central server and/or database 706, facilitating post-incident analysis, according to one embodiment. By automating data transfer along with charging, the system may ensure that video footage and sensor data 704 are always up-to-date and readily available for review or evidence, according to one embodiment. Automatic data transfer may minimize the risk of data loss or delays in uploading important footage and ensures that data is backed up regularly and consistently, improving the integrity and availability of data for investigative and judicial processes, according to one embodiment.

The docking station 702 may have a robust and secure physical wireless and wired interface to accommodate the specific shape and connection means (e.g., docking platform 708) of the combined memory and power module 110. This design may ensure that the modules can be easily and securely placed into the station without the risk of damage and/or misalignment, according to one embodiment.

Each dock (e.g., docking platform 708) may include contacts and/or an induction surface to provide power to the hybrid memory and power module(s) 110 for recharging. The system can be engineered to manage the charging process efficiently, potentially using AI to optimize charging rates and the health of the combined memory and power modules 110 over time, according to one embodiment.

The docking station 702 may be equipped with high-speed data transfer capabilities, which can be facilitated through direct contact pins, USB connections, and/or wireless communication protocols like Bluetooth, Wi-Fi, or NFC. AI of the combined memory and power module(s) 110 may manage the prioritization and queuing of data transfer to ensure that the most critical data is uploaded first, according to one embodiment.

Upon docking, the docking station 702 may automatically recognize each individual module, perhaps by a unique identifier, and may know the status of its power levels and data storage. AI may be used to predictively analyze the data needs based on past usage patterns and prepare the necessary resources accordingly, according to one embodiment.

The docking station 702 may be connected to a central database 706 and/or cloud storage system where the data from the modules is uploaded. AI algorithms may process and analyze the incoming data for patterns, anomalies, and/or relevant tactical insights, which may then be relayed to command centers and/or back to the field operators. LED lights and/or screens may provide visual feedback on the charging status and data transfer progress. These indicators may change colors and/or display messages to inform the user of completion and/or any errors, according to one embodiment.

Given its application in tactical scenarios, the docking station 702 may be built to withstand harsh conditions and provide secure storage for the modules. It may also include security features to prevent unauthorized access to the data being transferred and stored. The docking station 702 may be part of a larger network of such stations, allowing for scalability and redundancy in data collection and power management across a fleet of tactical gears. AI may manage this network, ensuring optimal performance across all nodes, according to one embodiment.

The docking station 702 may also include self-diagnostic capabilities to detect and report any malfunctions. AI may predict maintenance needs and schedule services without interrupting the station's operation, according to one embodiment.

Figure 8:
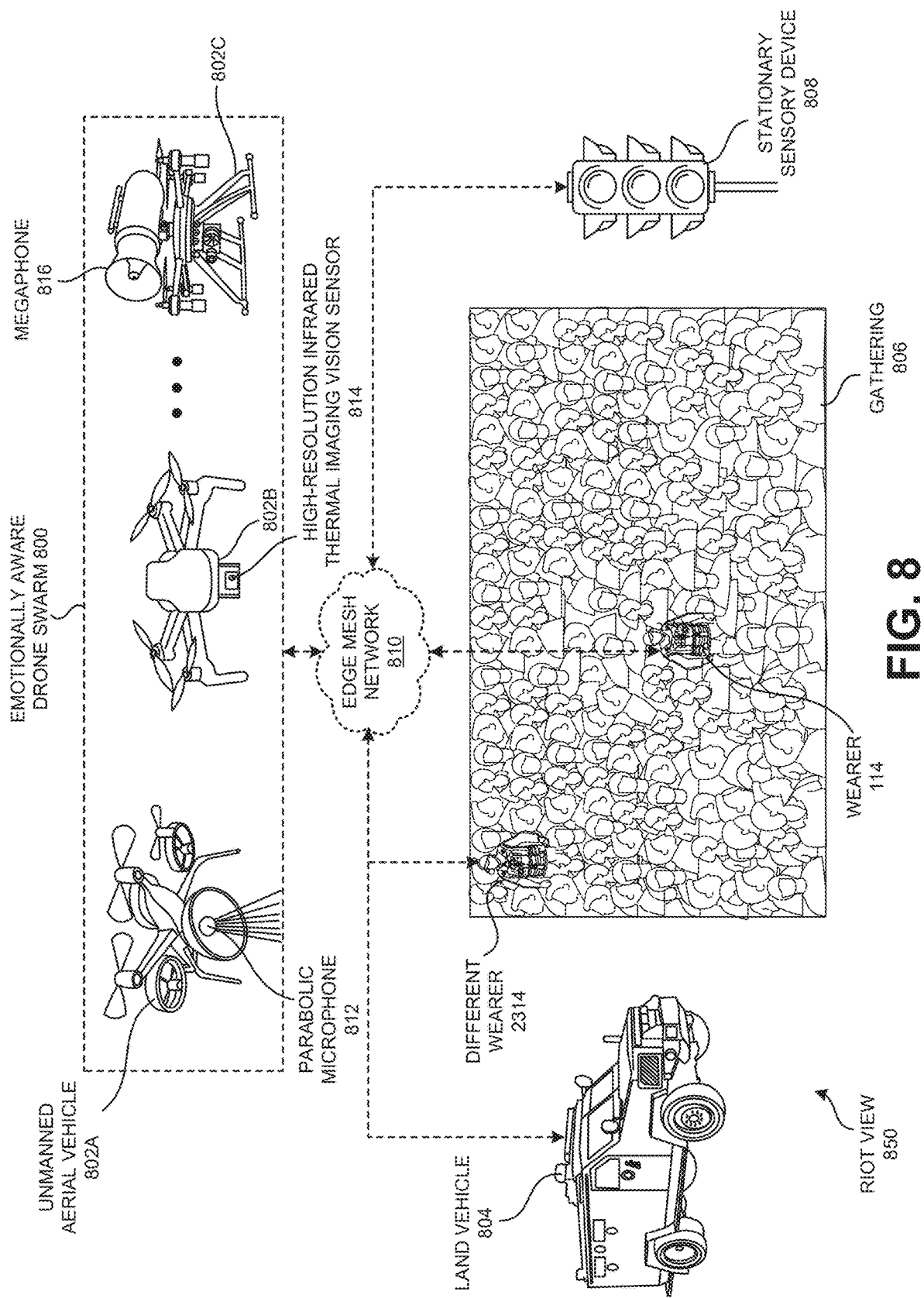
FIG. 8 is a riot view of a swarm of emotionally aware drones above a gathering using the body safety device of FIG. 1, according to one embodiment.

FIG. 8 is a riot view 850 of a swarm of emotionally aware drones 800 above a gathering 806, according to one embodiment. Particularly, FIG. 8 illustrates a sophisticated surveillance and response system designed for use in riot control and/or similar situations. It may include several components that work together to detect aggressive emotions in a crowd and alert a wearer 114 wearing an advanced tactical gear 104.

The unmanned aerial vehicle (UAV) 802 may be a part of an emotionally aware drone swarm 800. This UAV 802 may be equipped with sensors and algorithms capable of detecting emotional states, particularly aggressive emotions within a crowd and/or a gathering 806. These drones may use a combination of visual, thermal, and auditory sensors to analyze the crowd's behavior, according to one embodiment.

The UAVs 802 may be a part of a larger emotionally aware drone swarm 800, which works in a coordinated manner to cover a wide area and provide comprehensive data. The drones may share data and use AI to interpret the mood of the crowd, looking for specific patterns that indicate aggression and/or panic, according to one embodiment.

The drones of the emotionally aware drone swarm 800 may be focused on a large gathering 806 of people, which is described as riotous. The crowd's behavior may be the subject of the drones' surveillance, as detecting aggression quickly is crucial to preventing violence and/or responding effectively to it. In another embodiment, the drones of the emotionally aware drone swarm 800 may centrally launch from a police station in response to a request for service from a citizen within the jurisdiction and/or from police dispatch, according to one embodiment.

The system may include stationary sensory device(s) 808, such as surveillance cameras or other types of environmental sensors, that provide a fixed point of observation and data collection. The wearer 114 of the tactical gear 104 equipped with AI capabilities may receive and process the data collected by the drone swarm 800 and stationary sensory device(s) 808, according to one embodiment.

The system may be designed to alert wearer 114 of the tactical gear 104 when aggressive emotions are detected in the crowd. This alert may be of many forms, such as a visual signal on a heads-up display, an auditory alert through an earpiece, or a haptic signal (e.g., haptic alert 500) from the tactical gear 104 itself. The system may also be integrated with mobile command centers and/or support units (e.g., land vehicle 804, or naval ships), which can respond based on the data provided by UAVs 802 and the stationary sensor device(s) 808, according to one embodiment.

The threat detection model 108 of the advanced tactical gear 104 may process the data from the UAVs 802 and stationary devices 808 to provide real-time insights to the wearer 114, enabling a rapid and informed response to emerging threats within the gathering 806. This integrated system may enhance situational awareness and may be crucial for de-escalating potential violence or for coordinating a response with precision, according to one embodiment.

FIG. 8 illustrates an exemplary swarm scenario where multiple drones are deployed, according to one embodiment. In a swarm scenario with multiple drones, each drone may play a specific role in monitoring and highlighting different areas of concern within a large, complex situation, such as a widespread public protest or emergency incident. Here's how it can unfold:

Initial Deployment and Area Assessment: A swarm of drones 800 may be deployed to cover a large area. Each drone autonomously may navigate to different sections of the crowd, ensuring comprehensive coverage.

For example, unmanned aerial vehicle 802A may be equipped with a parabolic microphone 812 to increase the ability to capture audio on the ground. This type of parabolic microphone 812 on the drone may work by:

Directional Audio Capturing: The parabolic microphone 812 may focus on specific areas or individuals within a crowd, capturing clear audio despite the surrounding noise. This may be crucial for understanding the nature and direction of the riot, according to one embodiment.

Isolating Conversations: It may isolate speeches, chants, or commands that might indicate the intentions or mood of the crowd, or identify key figures like instigators or leaders, according to one embodiment.

Monitoring Changes in Crowd Dynamics: Sudden changes in audio levels (like escalation from murmurs to shouts) may signal a shift in the crowd's behavior, prompting early interventions, according to one embodiment.

Enhanced Situational Awareness: Audio insights complement visual surveillance, providing a more comprehensive picture of the situation, critical for law enforcement in strategizing their response, according to one embodiment.

Real-Time Data Transmission: Audio captured by the drone is transmitted in real-time to command centers, where it's analyzed for immediate decision-making, according to one embodiment.

FIG. 8 illustrates a UAV 802A equipped with a downward-facing parabolic microphone 812, designed for precision audio surveillance, according to one embodiment. The drone's design is sleek and aerodynamic, featuring a large parabolic microphone 812 may be prominently attached to its underside, according to one embodiment. The large parabolic microphone 812 may be oriented downwards to efficiently capture audio from the ground, according to one embodiment. Alongside this feature, the drone may include other advanced sensors and cameras for comprehensive monitoring, according to one embodiment. It may be depicted in flight above an urban landscape, demonstrating its capability to focus the parabolic microphone 812 directly below, gathering sound from specific ground locations while maintaining stable and controlled flight, according to one embodiment.

The design may also incorporate advanced sensors and cameras, supporting its surveillance functionalities, according to one embodiment.

Optimal Flight Height: The drone may fly at a height that allows for a broad view of the crowd while still being able to accurately detect individual behaviors and emotions. Typically, this may be around 100 to 150 feet. At this height, the drone can effectively cover a large area without compromising the detail needed for emotional analysis.

The UAV 802B may have a high-resolution infrared thermal imaging vision sensor 814 that may help in identifying individuals based on heat signatures, useful in low-visibility conditions and/or to identify individuals carrying weapons in the crowd. This may include visible weapons like firearms or concealed ones, detected through abnormal heat signatures, according to one embodiment.

The UAV 802C may have a megaphone 816 for law enforcement personnel to communicate with a crowd. This modern and sleek megaphone 816 may be equipped with an AI interface that analyzes data from sensors, capturing crowd stress and motivations. The megaphone 816 on the UAV 802C may adapt its tone, voice, and message content automatically, switching between different languages and modulating its tone to suit the crowd's mood, all based on real-time data.

The drone may position itself at an angle to direct the megaphone 816 to a particular area of a crowd. This megaphone attachment, designed for directional audio broadcasting, may be prominently featured and sleekly integrated into the drone's body, maintaining the drone's aerodynamic efficiency and mobility, according to one embodiment. The drone may be equipped with advanced sensors and communication equipment, all visible on its structure, according to one embodiment. This innovative design may enable the AeroMind™ to not only monitor and analyze crowd emotions but also to communicate directly with the crowd, delivering targeted audio messages as needed for effective crowd management and communication. The megaphone 816 on the UAV 802C, with its advanced AI capabilities, may play a unique and innovative role in crowd management by generating music or sounds specifically designed to calm a crowd. This feature works as follows:

Psychological Sound Design. The megaphone 816 may utilize AI algorithms to create or select music and sounds based on psychological principles known to induce calmness and reduce agitation, according to one embodiment. This may include certain frequencies, rhythms, and melodies that have a soothing effect on the human mind.

Real-Time Crowd Mood Analysis: The megaphone 816 may continuously analyzes the mood and stress levels of the crowd using data from integrated sensors and adjusts the music accordingly, according to one embodiment. For example, if the crowd is showing signs of increased stress or agitation, the megaphone 816 might play softer, slower-tempo music, according to one embodiment.

Customizable Soundscapes: The megaphone 816 may create customizable soundscapes that may be best suited for the specific crowd and context. This may include the ability to modify volume, tempo, and even musical composition in real-time.

Ambient Noise Integration: The megaphone 816 may intelligently integrate ambient sounds from the environment into the soundscape, according to one embodiment. For instance, in a noisy urban setting, the AI might overlay calming sounds that can effectively mask or blend with the background noise.

Voice and Music Balance: The megaphone 816 may maintain a balance between the use of calming music and necessary verbal announcements, according to one embodiment. This may ensure that important messages may be not drowned out by the music but are complemented by it.

Cultural Sensitivity: Recognizing the diversity in crowds, the megaphone 816 AI may consider cultural and demographic factors when selecting music or sounds, ensuring that they are appropriate and effective for the specific audience, according to one embodiment.

Non-Disruptive Deployment: The music may be deployed in a way that is non-disruptive and subtle, gradually blending into the crowd's soundscape to avoid sudden changes that might startle or have the opposite of the intended calming effect, according to one embodiment.

Feedback Loop for Effectiveness: There's a continuous feedback loop where the megaphone 816 may assess the effectiveness of the music or sounds in calming the crowd and makes real-time adjustments based on this feedback, according to one embodiment.

Recording and Analysis for Improvement: All interventions may be recorded and analyzed post-event to improve the effectiveness of sound-based crowd calming strategies in the future, according to one embodiment.

In one embodiment, the megaphone 816 may be physically on a movable vehicle rather than on each AeroMind™ themselves. This may minimize payload and weight of each AeroMind™, and allow for longer battery life.

Real-Time Analysis and Zone Identification: Each drone may use its onboard sensors to analyze the crowd below. They may identify various zones based on emotional and physical indicators—areas of high aggression, panic, peaceful protest, or medical emergencies.

Targeted Illumination and Marking: Drones hovering over areas of aggression or potential violence may use focused flood lights or colored strobes to mark these zones distinctly. This may alert ground personnel to potential hotspots.

Coordinated Responses: Drones over areas requiring immediate attention, like medical emergencies, may use a different colored light or pattern to guide emergency services directly to those in need.

Dynamic Adaptation: As the situation evolves, the drones may communicate with each other and with the command center through an edge mesh network 810, adapting their positions and focus areas. For example, if a new zone of conflict arises, nearby drones may converge to provide additional surveillance and illumination.

Crowd Movement Monitoring: Some drones may track the flow of the crowd, using lights to indicate safe exit routes or to guide people away from dangerous areas.

Data Collection for Command Decisions: The drones may continuously relay data back to the command center, where AI algorithms analyze patterns and make strategic recommendations for crowd control or emergency response.

Post-Event Analysis: After the event, data collected by the drone swarm may be analyzed to assess response effectiveness, may identify key areas for improvement, and may enhance future preparedness.

In this swarm scenario of FIG. 8, the coordinated use of multiple drones may maximize situational awareness and response effectiveness, showcasing the power of AI and drone technology in managing large-scale public events or emergencies.

Figure 9:
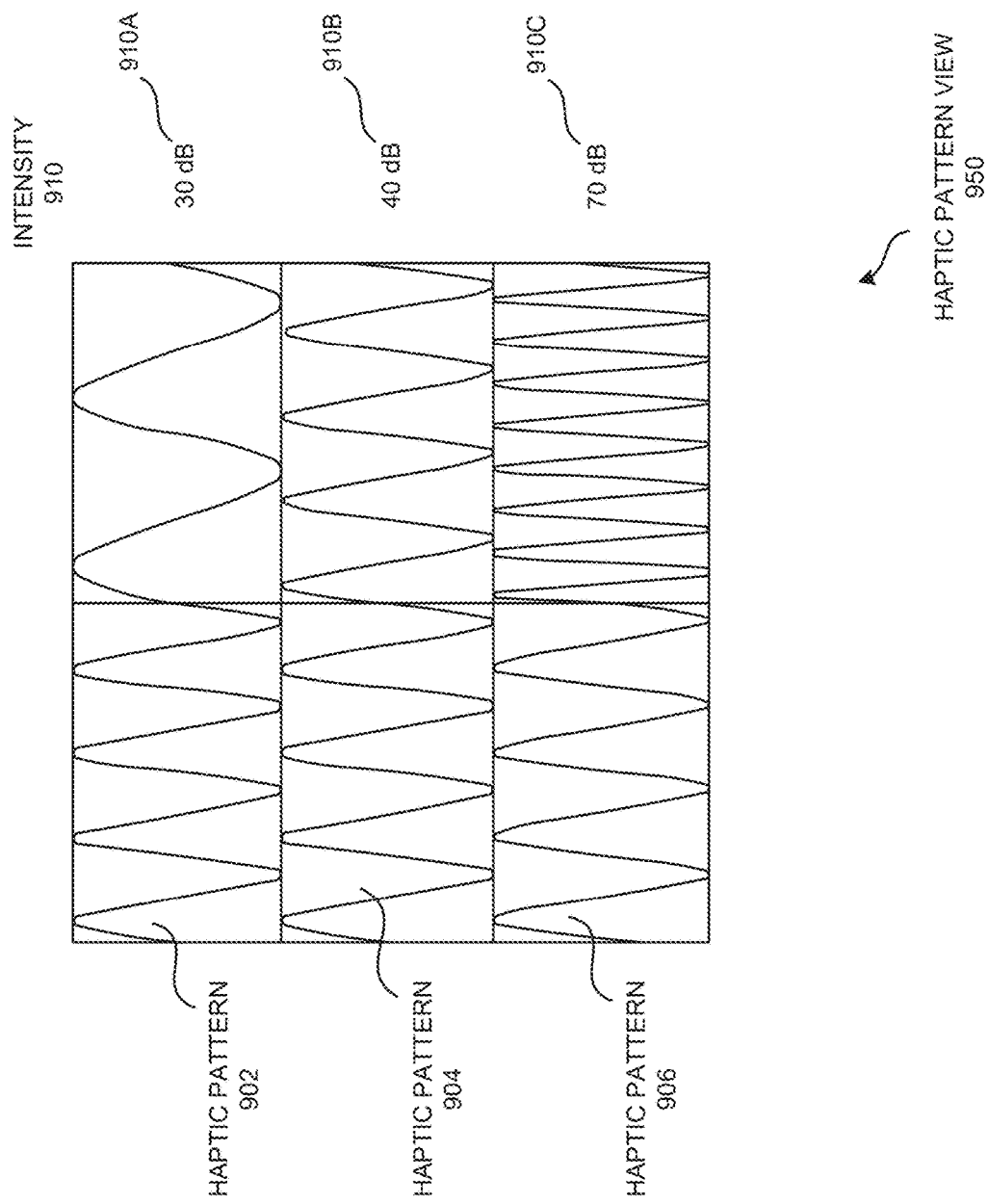
FIG. 9 is a haptic pattern view illustrating example haptic patterns of varying intensity generated by the haptic feedback device of the body safety device of FIG. 1, according to one embodiment.

FIG. 9 is a haptic pattern view 950 illustrating example haptic patterns 902, 904, 906 of varying intensity 910 generated by the array of haptic feedback device 210 of the tactical gear 104 in response to an ambient threat 112 detected by the sensors, according to one embodiment.

FIG. 9 illustrates different haptic feedback patterns 902, 904, and 906, each corresponding to a different intensity level 910A, 910B and 910C as indicated by decibels (dB) on the right-hand side. These patterns may be a part of haptic feedback system in the tactical gear 104 equipped with AI, where the intensity 910 of the vibration feedback provided by the haptic feedback device 106 varies depending on the proximity of a potential threat, according to one embodiment.

Haptic pattern 902 shows a waveform with a moderate amplitude and frequency of 30 dB, which can be a lower-intensity vibration. This pattern may indicate a distant or less immediate threat to the wearer 114, according to one embodiment.

Haptic pattern 904 has a higher amplitude than the first, suggesting a stronger vibration of 40 dB, indicating a medium intensity level. This may be indicative of a threat that is closer or more significant than the one associated with the first pattern, according to one embodiment.

Haptic pattern 906 shows a high amplitude and frequency waveform, with the highest intensity level at 70 dB. This may represent the most urgent vibration alert (e.g., haptic alert 500), signaling an immediate and/or very close threat, according to one embodiment.

The threat detection model 108 of the tactical gear 104 may process input from its sensors to evaluate the threat level and then activate the appropriate haptic feedback pattern to alert the wearer 114. The varying intensities allow for a nuanced response, giving the wearer 114 an immediate, non-visual indication of the threat level based on its proximity, enabling them to react accordingly without the need for visual and/or audio cues, according to one embodiment.

Figure 10:
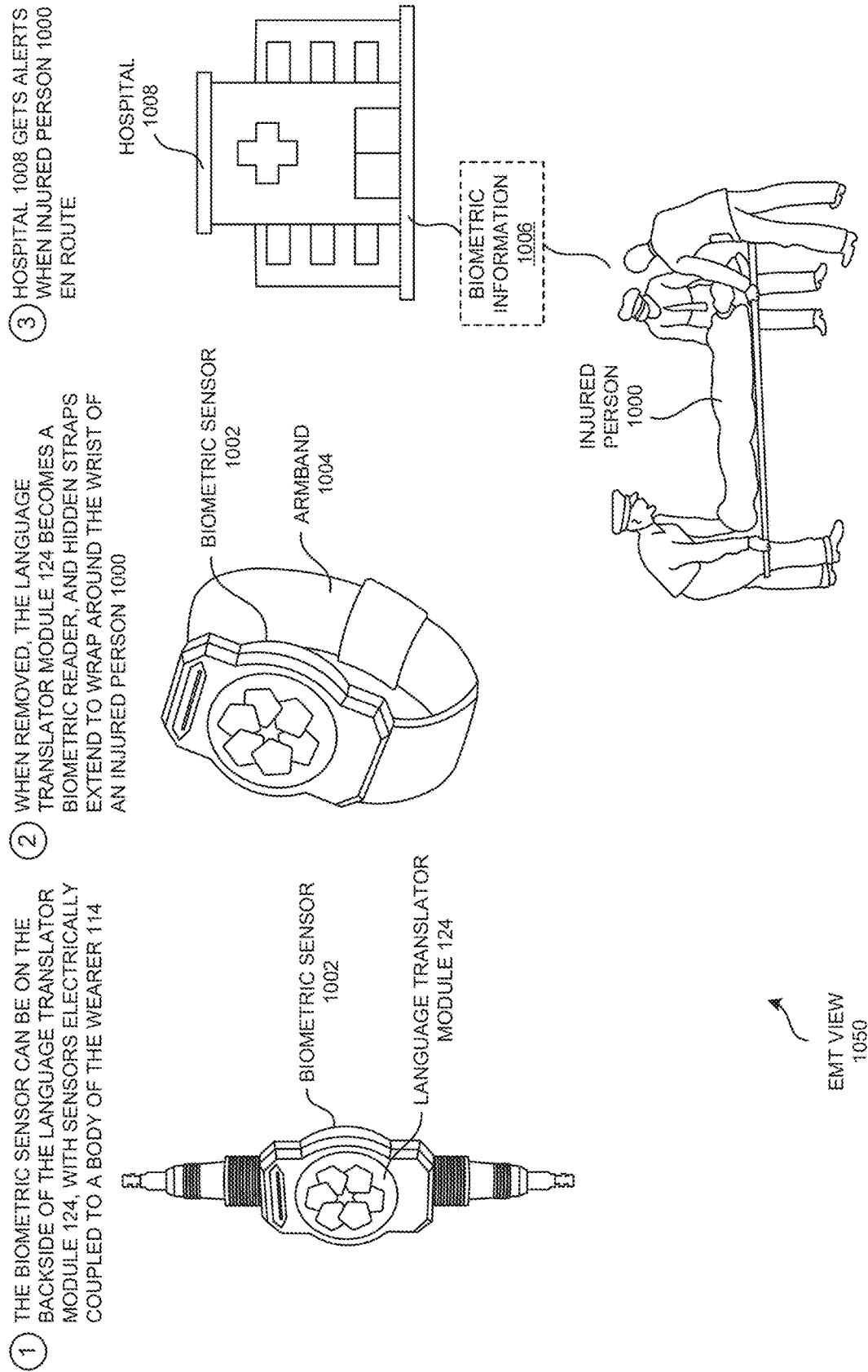
FIG. 10 is a medical emergency view illustrating a biometric sensor on a back side of the language translator module and touching a skin of the wearer of the body safety device of FIG. 1, and wherein the entire assembly is detachable and attachable to a wrist of an injured person through a hidden armband to communicate information biometric information to a hospital, according to one embodiment.

FIG. 10 is a medical emergency view 1050 illustrating a biometric sensor 1002 on a back side of the language translator module 124, and touching the skin of the wearer 114, and wherein the entire assembly is detachable and attachable to a wrist of an injured person 1000 through a hidden armband to communicate biometric information 1006 to a hospital 1008, according to one embodiment.

FIG. 10 depicts a multifunctional device that serves both as a language translator module 124 and a biometric sensor 1002, used in medical emergencies. This device is illustrated in three sequential use-case scenarios. In circle "1", the device may be a biometric sensor 1002 integrated with a language translator module 1002 worn by a medical professional and/or a first responder. This device may be a wrist-worn gadget. The biometric sensor 1002 may be located on the backside of the language translator module 124, allowing it to make contact with the skin of the wearer 114 and monitor vital signs and/or other biometric data, according to one embodiment.

The device may have a detachable and reconfigurable design. The device may be detachable from the wearer 114. Once removed, it may reveal hidden straps that allow it to be transformed into a standalone biometric reader. This reader may then be attached to the wrist of an injured person 1000 using the armband 1004, as shown in circle "2", according to one embodiment.

After attaching the device to the injured person's wrist, the biometric sensor 1002 may start collecting health data of the injured person 1000. This biometric information 1006 may then be wirelessly communicated to a hospital 1008 and/or other medical facility, as shown in circle "3". The hospital 1008, upon receiving this data, may get alerts and can monitor the injured person's condition en route to the facility, according to one embodiment.

This system is designed to provide real-time health monitoring of the injured person 1000 from the point of injury to the hospital 1008, improving the ability to begin assessment and preparation for treatment before the patient arrives. The dual functionality as a language translator may also be used to communicate with the injured person 1000 and/or responders who speak different languages, further aiding in the emergency response process, according to one embodiment.

A generative artificial intelligence (AI) body-worn apparatus equipped with haptic feedback modules designed to detect threats is described, according to one embodiment. The GovGPT DragonFly™ is a wearable technology designed for military personnel and law enforcement officers. It may combine advanced AI algorithms with a network of haptic feedback modules distributed across a specialized garment (e.g., tactical vest 104), according to one embodiment. The system's primary function is to provide real-time threat detection and situational awareness through tactile feedback, according to one embodiment.

FIG. 11 is a sentinel view 1150 illustrating a sentinel device 1100 integrated within the tactical gear 104 system of FIG. 1 to alert a soldier 1102 to movements and/or threats detected at potential entry and/or breaching points of a building, according to one embodiment.

During operations involving building entries, the system of body worn safety device 100 may alert a soldier 1102 (e.g., a wearer 114) to movements or threats detected at potential entry or breaching points, such as windows or back doors 1108, that are not in the immediate line of sight, according to one embodiment.

Particularly, FIG. 11 illustrates a sentinel view 1150 depicting the soldier 1102 with a weapon at the ready, within a room that is to be secured, according to one embodiment. The soldier 1102 may be a wearer 114 in an active combat zone. The soldier 1102 may be silently alerted by a haptic feedback module (e.g., using the array of haptic feedback device 210) in wearer's tactical gear 104 to a threat that is not visible to the wearer 114 (e.g., such as around the corner of a room, behind her, etc), according to one embodiment. In an alternative embodiment, the soldier 1102 in FIG. 9 may throw a sentinel device 1100 into the open door behind the wall, and enabling the pendant disc form of the sentinel device 1100 to unfurl and capture a sensory environment that is not within the direct line of sight of either the soldier 1102 and/or the body worn safety device 100, according to one embodiment.

FIG. 11 is a detailed illustration of the sentinel device 1100, according to one embodiment. This sentinel device 1100 may be a throwable, non-lethal reconnaissance tool designed for tactical applications, according to one embodiment. The sentinel device 1100 may be compact and sleek, resembling a small, futuristic grenade as shown in transport state 1100A of FIG. 11, according to one embodiment. The sentinel device 1100 may be equipped with advanced sensory equipment, including antennas, cameras, and environmental sensors, all integrated into its surface, according to one embodiment. The primary function of the sentinel device 1100 may be to scan and analyze environments that are not directly visible to the wearer 114 of the tactical gear 104 and/or a body worn pendant, according to one embodiment. Like a grenade, a single soldier 1102 may carry multiple sentinel device 1100 discs, according to one embodiment. Once thrown, it may deploy its sensors to gather critical information about potential threats and environmental conditions in the area, according to one embodiment. This data may then be relayed back to the soldier's 1102 body worn safety device 100, providing valuable intelligence and enhancing situational awareness, according to one embodiment.

The enhanced version of the sentinel device 1100 may feature a mechanical arm 1104 that extends once deployed. This advanced technology may allow the sentinel device 1100, when thrown into a location like behind a door 1108, to activate and unfurl a sophisticated mechanical arm 1100 equipped with a 360-degree panoramic camera 1106, according to one embodiment.

FIG. 11 depicts the unfurled state 1100B of the sentinel device 1100 deployed on the floor, actively monitoring enemy threats, according to one embodiment. Positioned just inside an open doorway, its mechanical arm 1104 with the 360-degree panoramic camera 1106 may be extended, to scan the area and capture images of enemy threats, according to one embodiment. In the background of FIG. 11, a soldier 1102, partially obscured and protected by the door 1108, may carefully monitor the situation, according to one embodiment. The soldier 1102 may rely on the data transmitted by the sentinel device 1100 to assess the threats and plan their next move, according to one embodiment. This scene captures the tension of the moment, contrasting the exposed sentinel device 1100 in the dangerous area with the soldier 1102 safely behind the door, illustrating the sentinel device's 1100 crucial role in providing intelligence, according to one embodiment. This unique feature may enable the sentinel device 1100 to capture a comprehensive view of the surrounding environment, transmitting detailed threat feedback (e.g., haptic alert 500) back to the haptic feedback device 106 on the body-worn safety device 100, according to one embodiment. The sentinel device's 1100 capabilities in environmental sensing and data collection may aid in capture of an environment even when not directly worn on a soldier 1102, in one embodiment.

Offensive Use of the Sentinel Device's 1100

In an exemplary embodiment, a command by the soldier 1102 may trigger the sentinel device 1100 to detonate like a grenade. The system may incorporate a tongue-based action that triggers the sentinel device 1100 disc to detonate like a grenade. It may be a specific and deliberate movement that minimizes the risk of accidental activation, according to one embodiment. The wearer 114 may execute a specific sequence of tongue presses against the roof of the mouth (e.g., bookmark location 402 of FIG. 4), designed to be distinct and unlikely to occur in normal speech or eating, according to one embodiment. For example, the sequence can be: press the tongue hard against the front roof of the mouth, then quickly slide it to the back, and finally press hard again at the back. For example, this sequence may be something like a "tap-slide-tap" pattern to request help 404, according to one embodiment.

Optionally, to ensure safety and prevent accidental detonation, the system may require a confirmation action after the initial sequence, according to one embodiment. This may be a simple but distinct action, like pressing the tongue against the cheek, according to one embodiment. After confirmation, a short delay may be implemented before detonation, allowing the wearer 114 and/or soldier 1102 time to ensure safety and distance from the sentinel device 1100, according to one embodiment. Extensive training may be essential for users (e.g., wearer 114, soldier 1102) to reliably and safely execute this command under various conditions, according to one embodiment. To enhance security, each unit may have the option to customize the detonation sequence, similar to setting a personal PIN, according to one embodiment. This function may be reserved for critical situations where a controlled explosion is necessary for mission success and/or for safety reasons, according to one embodiment.

Ideally, the sentinel device 1100 system may be designed to notify the command center before activation, ensuring coordination and safety, according to one embodiment. This tongue-based action for triggering a controlled detonation of the sentinel device 1100 may add a powerful capability to the device, according to one embodiment. However, due to the potential risks associated with such a function, it may be implemented with multiple layers of safety and security measures to ensure it's used appropriately and effectively, according to one embodiment.

Autodetonation of the Sentinel Device 1100 Disc

An embodiment of the sentinel device 1100 that features auto-detonation based on audio and/or video pattern recognition may involve integrating advanced AI algorithms capable of analyzing and confirming specific target patterns and location within a kill zone, according to one embodiment. Once deployed in a tactical environment, the sentinel device 1100 may continuously scan and process audio and visual data, according to one embodiment. When it detects a pattern that matches a predefined target—which can be a specific sound, visual signal, or combination of both—it may autonomously confirm the target's identity, according to one embodiment. Upon confirmation, the device may activate its auto-detonation mechanism, according to one embodiment. This feature may make the sentinel device 1100 highly effective for specific mission objectives where identifying and neutralizing a target swiftly is crucial, according to one embodiment. The sentinel device 1100 system may be equipped with safety protocols to minimize false positives and ensure operational security, according to one embodiment.

A spherical disc (e.g., sentinel device 1100) may be wirelessly coupled with the body worn safety device 100 that is carryable by the wearer 114 and which is throwable by the wearer 114, wherein the spherical disc may automatically unfurl when it is is thrown by the wearer 114 onto a level surface, such that a panoramic camera 1106 of the spherical disc is perpendicularly manifested and actively recording when in the unfurled state 1100B, and the haptic feedback device 106 on the body worn safety device 100 may vibrate when ambient threat 112 is visible to the camera of the spherical disc in the unfurled state 1100B, according to one embodiment.

Figure 12:
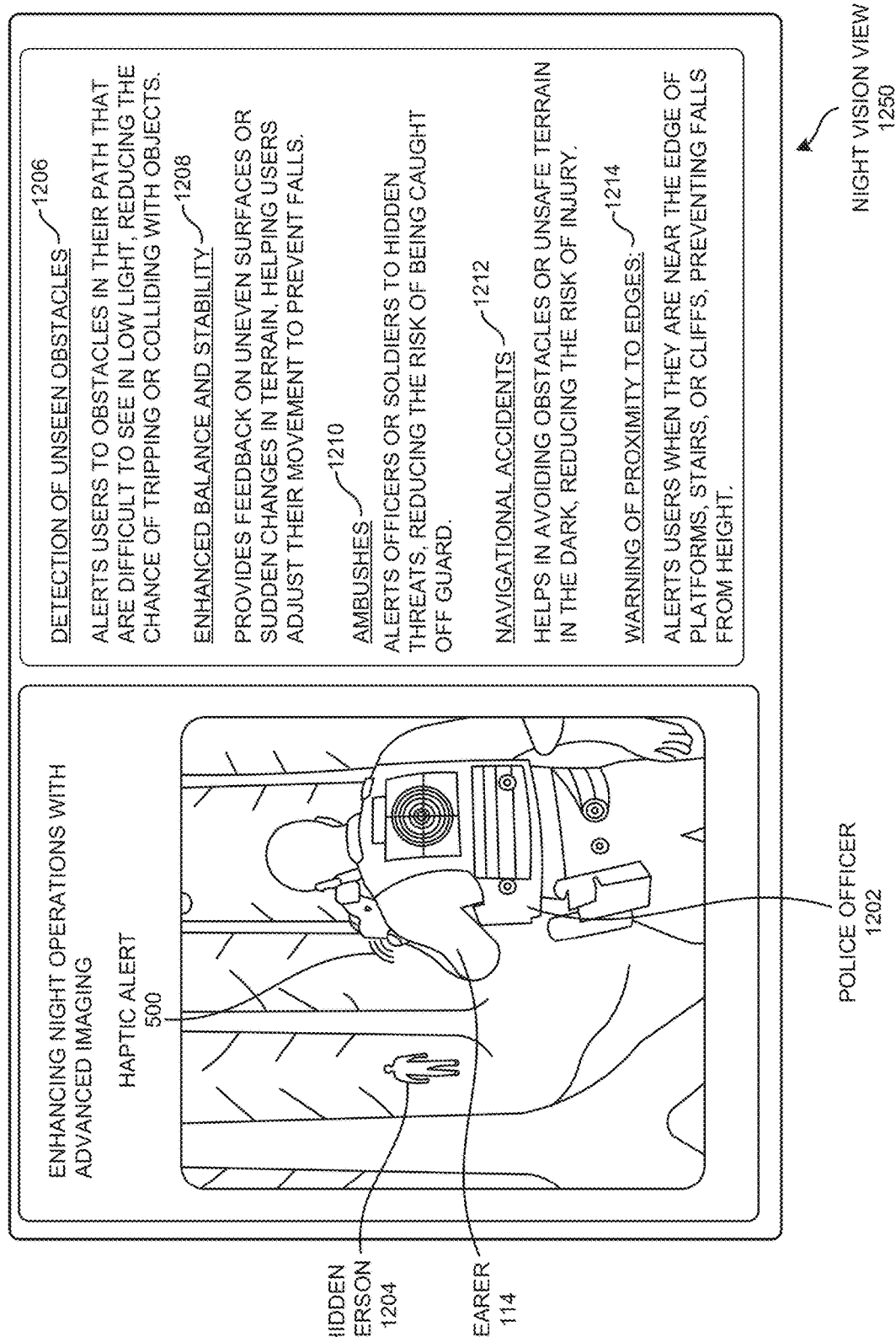
FIG. 12 is a night vision view illustrating a police officer wearing the body safety device of FIG. 1, searching in the woods at night for a suspect, receiving a haptic alert from low visibility sensors that detect a hidden person in a concealed position, according to one embodiment.

FIG. 12 is a night vision view 1250 illustrating a police officer 1202 searching in the woods at night for a suspect, receiving a haptic alert 500 from low visibility sensors that detect a hidden person 1204 in a concealed position, according to one embodiment.

In low-visibility conditions, the system of body worn safety device 100 of FIG. 1 may use infrared and/or thermal imaging to detect human presence or movement and provide haptic feedback to alert (e.g., using haptic alert 500) the wearer 114, compensating for reduced visual capability, according to one embodiment. In an embodiment designed for low-visibility conditions, the system of body worn safety device 100 of FIG. 1 incorporates infrared and/or thermal imaging technology combined with haptic feedback to detect human presence or movement, according to one embodiment. This embodiment may enhance the wearer's 114 situational awareness when visual capabilities are compromised, such as in fog, smoke, and/or complete darkness, according to one embodiment. These sensors may be integrated into the wearable device (e.g., retainer 400A, 400B), such as a helmet, goggles, and/or the body suit (e.g., tactical gear 104) itself, according to one embodiment. They may be capable of detecting heat signatures and differentiating between the ambient temperature and the warmth of a human body, according to one embodiment.

The suit and/or wearable device may be embedded with a network of haptic feedback device 106 (e.g., using array of haptic feedback device 210 of tactical gear 104) that can provide tactile feedback in various patterns (e.g., haptic pattern 902, 904, 906) and intensities (e.g., intensity 910, 910A, 910B, 910C), according to one embodiment. An onboard AI-driven processor (e.g., using modular compute assembly 324 of the threat detection model 108) may interpret the data from the infrared/thermal sensors and translate it into actionable insights, according to one embodiment. The infrared/thermal sensors may scan the environment continuously, according to one embodiment. When a human heat signature is detected, the system may calculate its position relative to the wearer 114, according to one embodiment. Upon detection of a human presence, the system may trigger the haptic feedback mechanism, according to one embodiment. The location of the feedback (e.g., haptic alert 500) on the wearer's body may correspond to the direction of the detected presence, according to one embodiment. For instance, a vibration on the right arm may indicate a presence to the right of the wearer 114, according to one embodiment.

The intensity (e.g., intensity 910, 910A, 910B, 910C) and pattern (e.g., haptic pattern 902, 904, 906) of the haptic feedback may convey additional information, according to one embodiment. A rapid, pulsating vibration (e.g., haptic pattern 906) may indicate an immediate threat, while a slow, rhythmic pattern (e.g., haptic pattern 902) may signify a non-threatening human presence, according to one embodiment. Besides human detection, the system may also identify terrain obstacles or other significant environmental features, providing haptic feedback (e.g., haptic alert 500) to guide the wearer 114 around these potential hazards, according to one embodiment.

The embodiments of body worn safety device 100 of FIG. 1 displayed in FIG. 12 may include detection of unseen obstacles 1206 capabilities to alert users to obstacles in their path that are difficult to see in low light using the infrared/thermal sensors, which may help reducing the chance of tripping and/or colliding with objects. The enhanced balance and stability 1208 feature may provide feedback on uneven surfaces and/or sudden changes in terrain, helping users adjust their movement to prevent falls. The ambushes 1210 feature tab may alert officers and/or soldiers to hidden threats, thus reducing the risk of being caught off guard. The navigational accidents 1212 capabilities may help in avoiding obstacles and/or unsafe terrain in the dark, reducing the risk of injury. The warning of proximity to edges 1214 feature may alert users when they are near the edge of platforms, stairs, or cliffs, preventing falls from height, according to one embodiment.

The system of the body worn safety device 100 of FIG. 1 may be linked with other devices such as a heads-up display (HUD) and/or a handheld monitor to provide a visual representation of the thermal imaging data. Users (e.g., Police officer 1202) may customize the type of haptic feedback they receive for different kinds of detections, tailoring the system to their preferences and operational needs. Over time, the AI processor (e.g., using modular compute assembly 324 of the threat detection model 108) may learn from the wearer's 114 (e.g., Police officer 1202) responses and environment, improving the accuracy and relevance of the feedback provided. The system may operate silently, making it ideal for stealth scenarios where noise discipline is critical, according to one embodiment.

Figure 13:
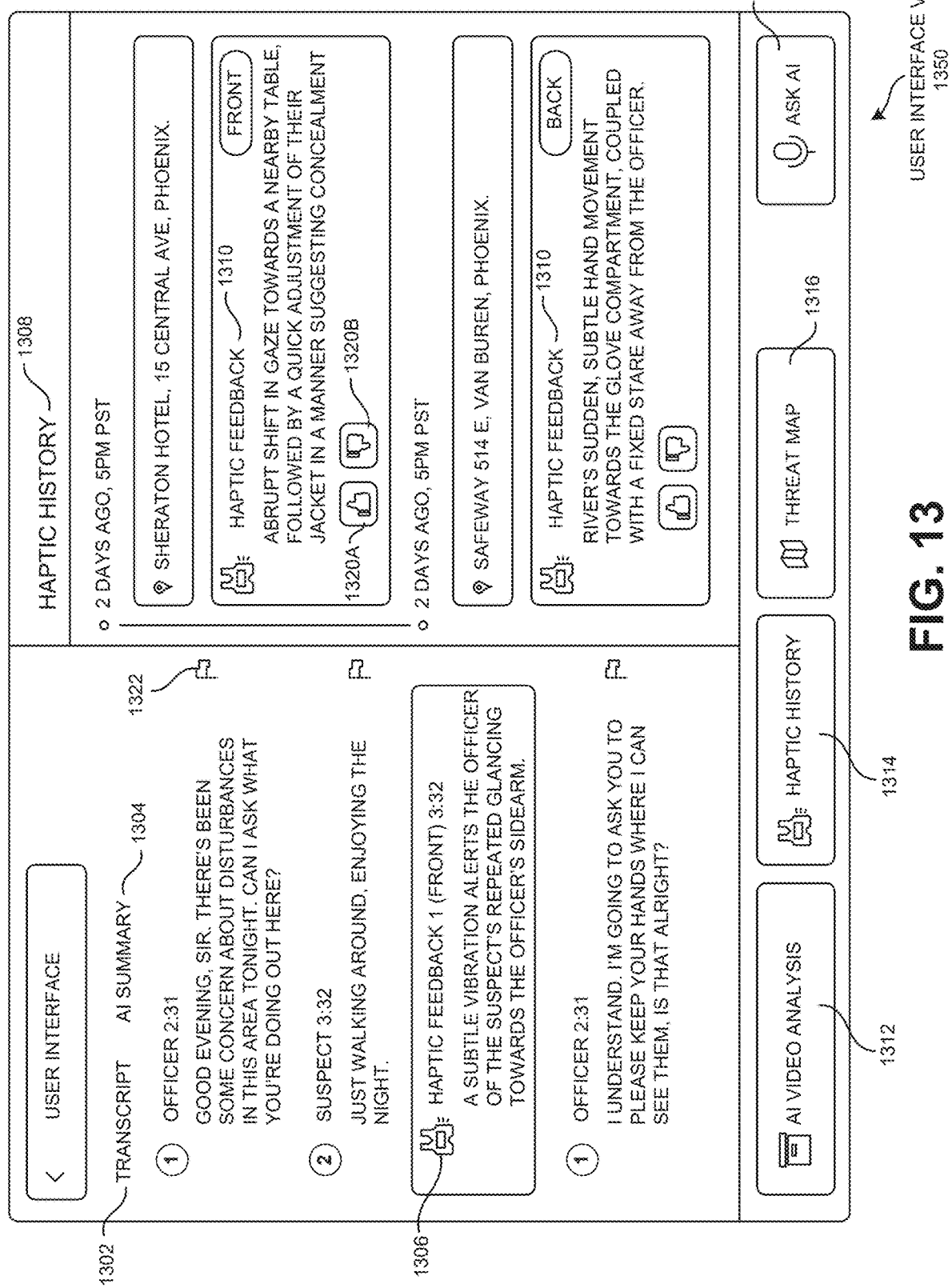
FIG. 13 is a user interface view of the system of the body worn safety device of FIG. 1, designed to provide real-time feedback and information to the user, according to one embodiment.

FIG. 13 is a user interface view 1350 of the system of the body worn safety device 100 of FIG. 1, designed to provide real-time feedback and information to the user, according to one embodiment.

A transcript 1302 tab may provide a transcript of communications or interactions, presumably captured by the tactical gear's audio equipment (e.g., using the body worn camera 216). It may include a timestamp indicating when the interaction occurred, and an AI summary 1304 may provide condensed information and/or analysis of the situation. The AI summary 1304 may include feature flag 1322 that may be used for confirmations, alerts, and acknowledgments that require minimal user interaction. The flag 1322 feature may turn certain functionality of the AI summary 1304 on and off during runtime, without deploying new code. This may allow for better control and more experimentation over the full lifecycle of features. Haptic feedback notifications 1306 tab may provide an indication of where on the tactical gear 104 the feedback was felt (e.g., front or back). These notifications may correspond to specific times and describe the nature of the haptic alert 500. For example, one alert may describe a "subtle vibration" that alerts the officer of the suspect's glances towards the officer's sidearm, according to one embodiment.

Haptic history 1308 tab may provide logs of previous haptic feedback 1310 instances with timestamps and locations. Each entry may provide context for the haptic feedback, describing the suspect's behavior that prompted the alert. For instance, one entry notes an "abrupt shift in gaze" by someone at a hotel, followed by a quick adjustment of their jacket in a way that suggests they may be concealing something, according to one embodiment. The haptic feedback 1310 may include feedback buttons 1320A and 1320B to enable a user to easily interact with status updates, content, photos and videos based on their preferences, and train the AI model based on human feedback to which alerts were accurate and which were not.

The user interface 1350 of the system may feature icons for additional functionalities. For example, an AI Video Analysis 1312 tab may allow the user (e.g., wearer 114, a law enforcement officer, a police officer 1202, a soldier 1102, etc.) to access video feeds, the Haptic History 1314 tab may allow the user to review historical haptic data, the Threat Map 1316 tab may allow the user to view a map with potential threats highlighted, and the Ask AI 1318 tab may allow the user to query the AI for information and/or advice, according to one embodiment.

The user interface 1350 of the system may be designed to be intuitive and informative, providing actionable intelligence and sensory alerts to enhance situational awareness. The integration of haptic feedback with visual data representations may indicate a sophisticated system that leverages multiple data sources to aid the user in assessing and responding to potential threats, according to one embodiment.

Figure 14:
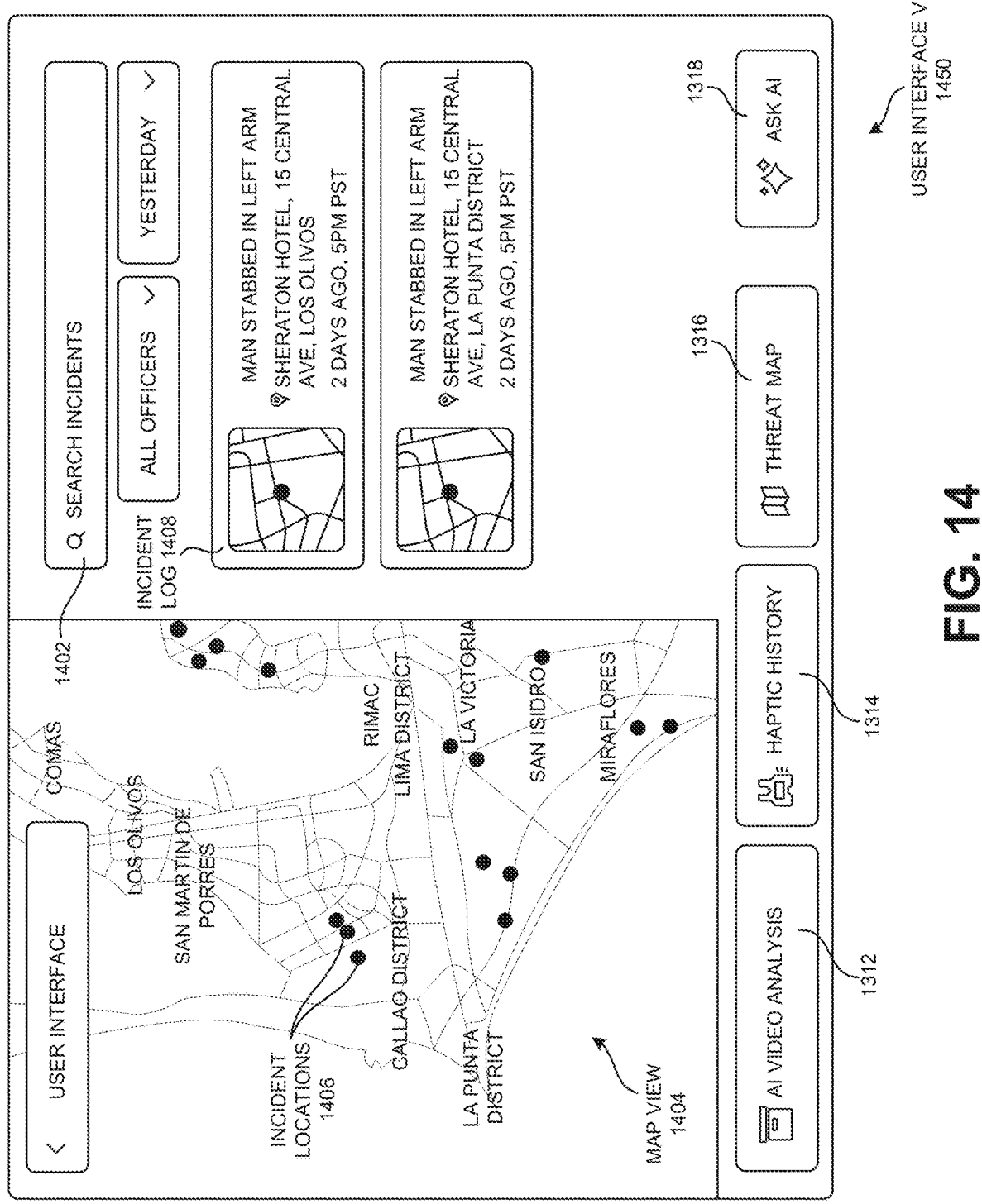
FIG. 14 is a user interface view of the system of the body worn safety device of FIG. 1, illustrating a realtime map view of a geographical location, according to one embodiment.

FIG. 14 is a user interface view 1450 of the system of the body worn safety device 100 of FIG. 1, illustrating a realtime map view 1404 of geographical locations with potential threats highlighted, according to one embodiment.

Particularly, FIG. 14 illustrates a map view 1404 of the incident locations 1406 with navigational tools for its user. This interactive map may be useful for situational awareness, allowing the wearer 114 (e.g., a law enforcement officer, a security personnel, a police officer 1202, a soldier 1102, etc.) to visualize the geographic distribution of incidents and resources, according to one embodiment.

The system may provide an incident log 1408 for its user. The interface may include a search bar 1402 with dropdown menus, to filter searches by officer (e.g., wearer 114, a law enforcement officer, a security personnel, a police officer 1202, a soldier 1102, etc.) and/or time frame. The system may list the incident based on the time frame and search query. Each incident may be accompanied by a description of the injury sustained with the affected area highlighted, providing a quick visual reference for the type of injury sustained, according to one embodiment.

Overall, the UI may be designed to provide real-time data and analytics to the wearer 114 of the advanced tactical vest 104, enhancing decision-making and response efficiency in the field. The integration of map-based data visualization with a searchable incident log 1408 may offer a comprehensive overview of the situation at hand, according to one embodiment.

FIG. 15 is another user interface view 1550 of the system of the body worn safety device 100 of FIG. 1, illustrating a realtime analysis of a video and a transcript of an incident displayed on the user device, according to one embodiment.

Particularly, FIG. 15 displays a user interface focusing on a real-time analysis and threat assessment feature of the system of the body worn safety device 100 of FIG. 1. The system may provide a navigation and control tool 1502 which may help the user to start and/or pause the real-time analysis 1504, a dropdown menu for navigating incident list 1506, and a share function 1508 key for the user to disseminate the information as needed, according to one embodiment.

The video analysis input may enable the system to analyze video footage in real-time. This feature of the interface may use machine learning to review and interpret video data. The system may have a live video and threat identification ability for active real-time video streaming. The interface may list the identified threats detected along with the specific timestamp observed by tagging and recording the location of incidents and/or threats, according to one embodiment.

The system may provide a real-time analysis 1504 summary with an overview of the environment (e.g., urban outdoor setting, likely in a developed city area), persons (e.g., with an example of an identified police officer), and an overall situation assessment (e.g., a controlled scene with no immediate indications of safety concerns). The system may also provide detailed reports and/or extended data for the incident recorded, identify individuals and classify them (e.g., suspect), provide details about them, and assess their attention and focus levels, according to one embodiment.

The interface may provide a sophisticated system designed to support law enforcement officers by providing situational awareness through live video analysis, threat detection, and real-time data reporting. The system's ability to analyze and summarize complex scenes in real-time may assist in decision-making during critical incidents, according to one embodiment.

Figure 16:
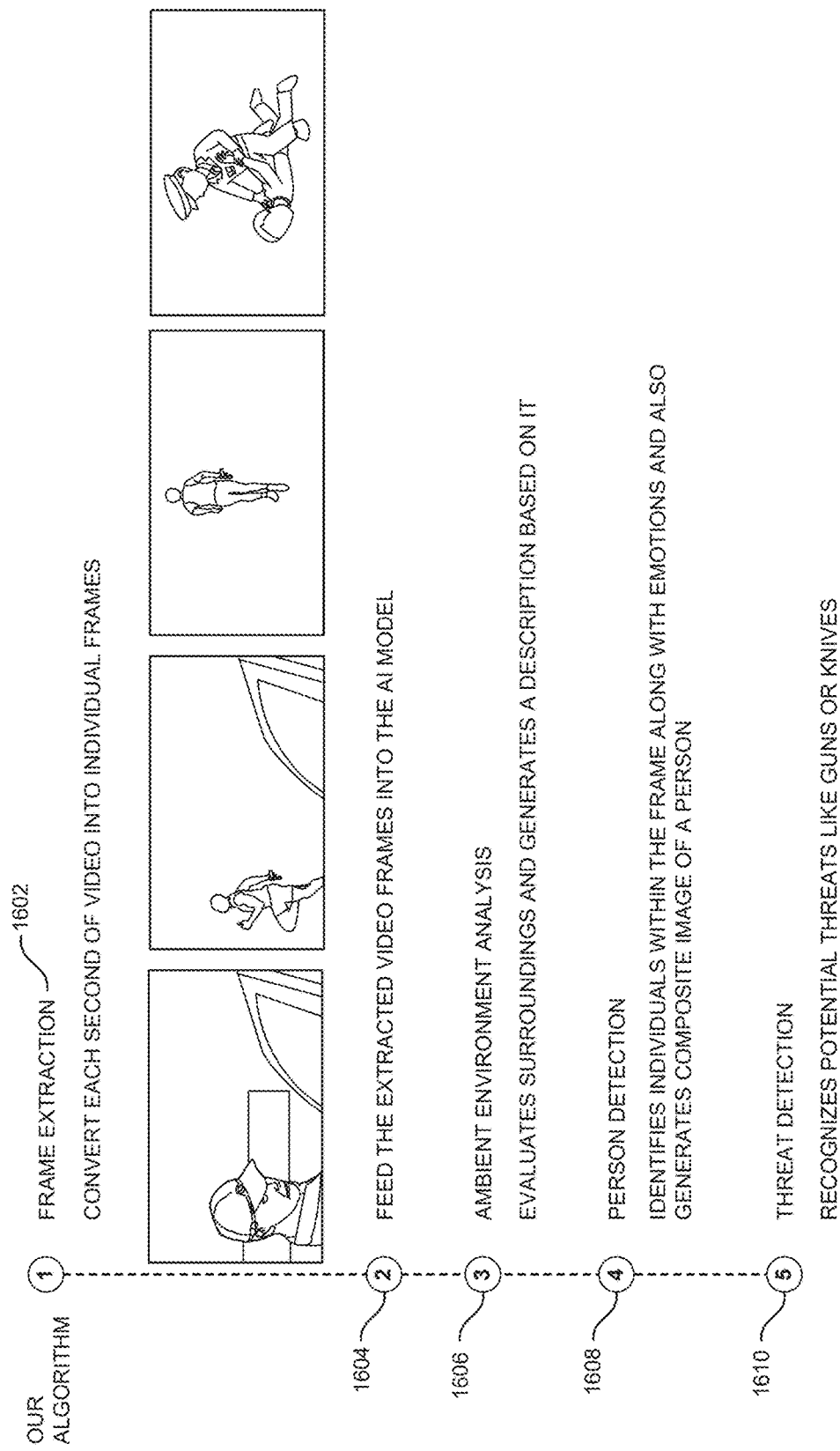
FIG. 16 outlines an algorithm used by the generative artificial intelligence (AI) of the body worn safety device of FIG. 1 to analyze a video footage, according to one embodiment.

FIG. 16 outlines an algorithm used by the generative artificial intelligence (AI) body worn safety device 100 of FIG. 1 to analyze a video footage, according to one embodiment. The process may be broken down into the following sequential steps:

Frame Extraction 1602: The first step may involve converting each second of video into individual frames. This may allow the AI to perform an in-depth analysis of each moment in the video, rather than trying to analyze a continuous stream, according to one embodiment.

Feed into AI Model 1604: After the frames are extracted, they are fed into the threat detection model 108 of the system and is trained to interpret and analyze the visual data within each frame, according to one embodiment.

Ambient Environment Analysis 1606: The threat detection model 108 may then evaluate the surroundings and generates a description based on it. This may involve identifying the type of location, assessing lighting conditions, and/or other environmental factors, according to one embodiment.

Person Detection 1608: In this step, the threat detection model 108 may identify individuals within the frames. The threat detection model 108 may not only assess the presence of people but also their emotions, which can be inferred from facial expressions, body language, etc. The threat detection model 108 may also generate a composite image of a person, which can be used for later identification or analysis, according to one embodiment.

Threat Detection 1610: The final step may involve recognizing potential threats, such as guns or knives. The threat detection model 108 may look for the shape, size, and other characteristics of objects that match known weapons, according to one embodiment.

This algorithm may be part of a system designed to provide real-time analysis to support individuals wearing the tactical vest 104. By breaking down video into frames and applying a multi-step analysis, the threat detection model 108 may offer detailed insights into both the environment and the individuals within it, highlighting potential threats and providing situational awareness to the wearer 114, according to one embodiment.

FIG. 17 is a table view 1750 illustrating the comparative analysis of the generative artificial intelligence (AI) of body worn safety device 100 of FIG. 1 to analyze video footage, according to one embodiment. The table view 1750 presents an analysis contrasting the features of body-worn cameras with those of the tactical gear 104 described in various embodiments of FIGS. 1-16 and FIG. 19. The table lists various functions and indicates whether each feature is present or absent in the respective equipment.

For example, the tactical gear 104 described in various embodiments of FIGS. 1-16 may be able to detect and alert an officer of weapons. However, this feature is not available in body-worn cameras. This implies that the tactical gear 104 may detect weapons and alert the wearer 114, according to one embodiment.

The tactical gear 104 described in various embodiments of FIGS. 1-16 may be able to detect and alert an officer of opioid and alcohol symptoms but this feature is missing from body-worn cameras. Tactical gear 104 may detect signs or symptoms related to opioid and alcohol use and notify the officer, according to one embodiment.

The tactical gear 104 described in various embodiments of FIGS. 1-16 may offer real-time language translation capabilities, while the body-worn cameras do not. The tactical gear 104 may interpret and translate spoken language on the spot, which is a sophisticated AI feature, according to one embodiment.

The tactical gear 104 described in various embodiments of FIGS. 1-16 may also provide a description of events in words, which body-worn cameras cannot do. This may refer to the AI's ability to analyze situations and articulate them in a textual format, for reports or briefings, according to one embodiment.

The body-worn cameras may have the capability to record video at the scene of incidents, which is their primary function. However, this feature may be optional in the tactical gear 104 indicating that the vest does not have video recording capabilities, or may not be its primary feature, according to one embodiment.

This comparative analysis showcases the advanced capabilities of AI-equipped tactical gear over traditional body-worn cameras, emphasizing enhanced situational awareness, detection capabilities, and language translation as key differentiators, according to one embodiment.

FIG. 18 is another table view 1850 illustrating the comparative analysis of the generative artificial intelligence (AI) of body worn safety device 100 of FIG. 1, according to one embodiment. The table view 1850 includes a comparative feature between a traditional tactical vest and an advanced tactical gear 104 described in various embodiments of FIGS. 1-16.

The advanced tactical gear 104 described in various embodiments of FIGS. 1-24 may be capable of detecting weapons and alerting the wearer 114 while the traditional tactical vests do not have this feature. The advanced tactical gear 104 described in various embodiments of FIGS. 1-24 may have the ability to detect and alert the wearer to signs of opioid and alcohol use while this feature is also absent in traditional vests. The advanced tactical gear 104 described in various embodiments of FIGS. 1-24 may have the ability to detect and alert the wearer to signs of opioid and alcohol use while the traditional vests lack this feature. Traditional vests do not offer real-time language translation, whereas the advanced tactical gear 104 does, showcasing its advanced communication capabilities are supported by AI, according to one embodiment.

The advanced tactical gear 104 described in various embodiments of FIGS. 1-24 has the ability to analyze and verbalize the context or events, but is not available in traditional tactical vests. The traditional tactical vest protects from gunshots. Despite its advanced AI capabilities, the tactical gear 104 does not compromise on the fundamental protective function of a tactical vest, according to one embodiment.

This comparative analysis highlights the enhanced technological capabilities of tactical gear 104 over a traditional tactical vest, offering not only protection from physical threats but also advanced detection and communication features, according to one embodiment.

Figure 19:
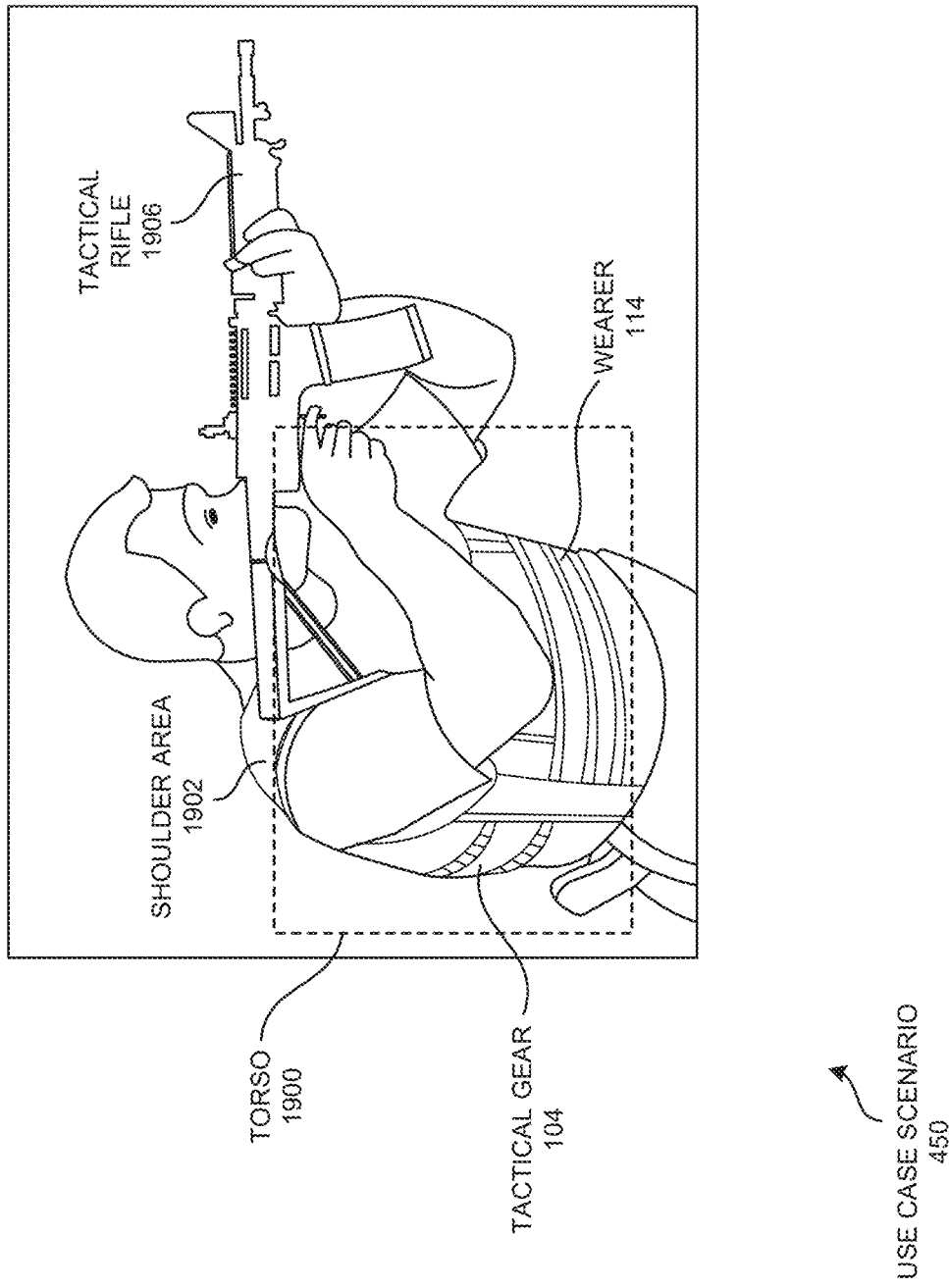
FIG. 19 is a use case scenario of the body worn safety device of FIG. 1, according to one embodiment.

FIG. 19 is a use case scenario of the body worn safety device 100 of FIG. 1. The scenario depicts a tactical situation where the wearer 114 may be engaged in law enforcement, military operations, and/or security activities. The tactical gear's 104 AI features might be actively used in this scenario to provide real-time data, enhance the wearer's decision-making, and/or alert them to threats as described in various embodiments of FIGS. 1-18. Particularly, FIG. 19 illustrates a practical application of the tactical gear 104 in a field operation where the advanced capabilities of the AI can assist the wearer 114 during critical tasks. As shown in figure, the tactical gear 104 may protect the torso 1900 region of the wearer 114. Despite its advanced capabilities, the tactical gear 104 may be designed to be unobtrusive and comfortable during tactical situations. The integration into the gear may distribute the weight evenly across the officer's torso 1900, avoiding the discomfort associated with traditional body cameras, according to one embodiment. The wearer 114 may be able to support its tactical rifle 1906 onto his shoulder area 1902 while field operation without obstructing his movement, according to one embodiment.

Figure 20:
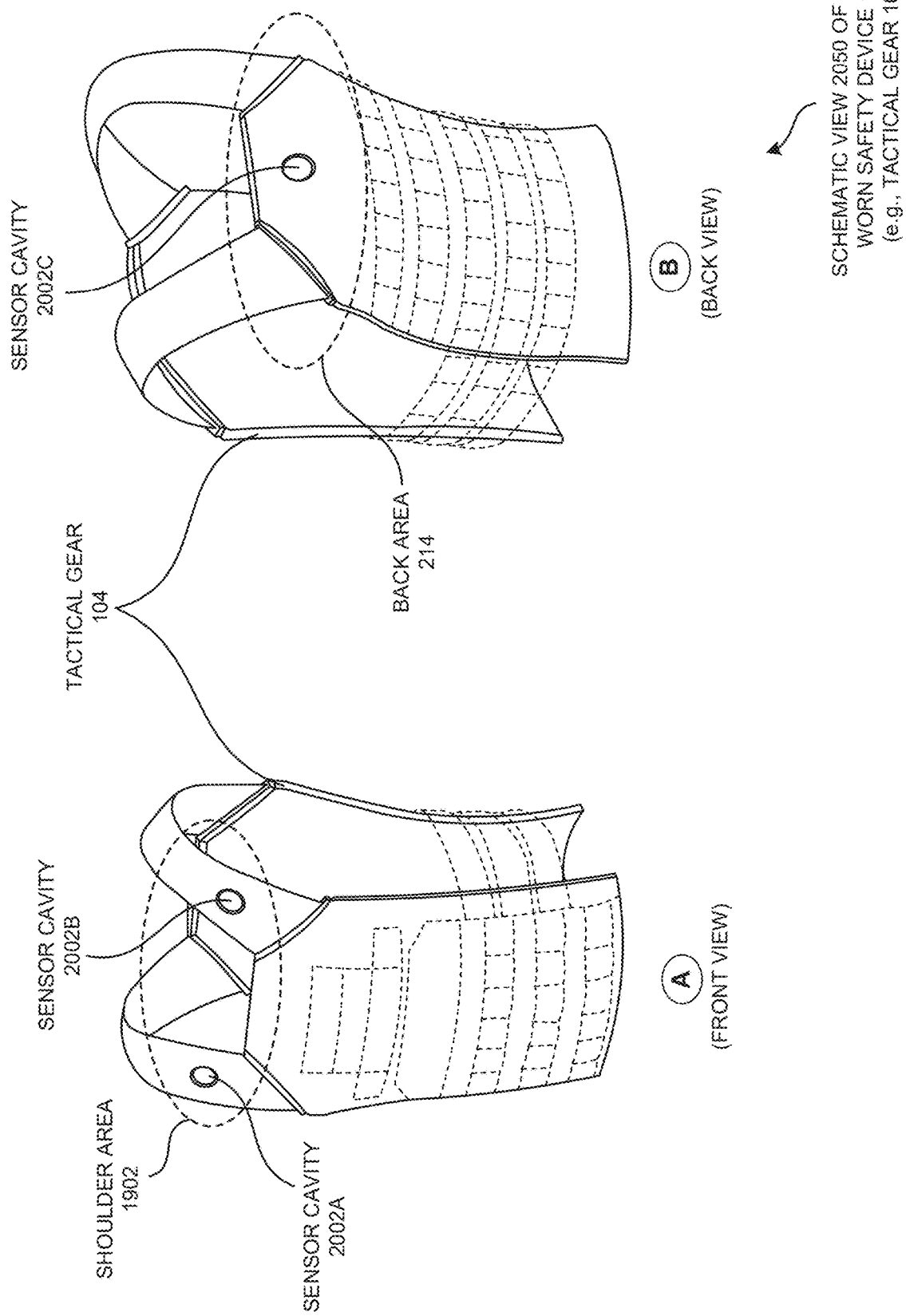
FIG. 20 is a schematic view of the body worn safety device of FIG. 1 illustrating the provision of cavities for installation of sensors in the shoulder area of the body worn safety device, according to one embodiment.

FIG. 20 is a schematic view 2050 of the body worn safety device of FIG. 1 illustrating the provision of cavities for installation of sensors in the shoulder area 1902 of the body worn safety device 100, according to one embodiment.

As shown in circle "A" front view of FIG. 20, the tactical gear 104 may have sensor cavity 2002A and sensor cavity 2002B in the shoulder area 1902 provided for installation of visual sensors 102 in the front portion of the tactical gear 104. In addition, as shown in circle "B" back view of FIG. 20, the tactical gear 104 may have sensor cavity 2002C in the back area 214 provided for installation of rear facing sensor 206 in the rear portion of the tactical gear 104, according to one embodiment. The provision of sensor cavities 2002A and 2002B in the shoulder area 1902 may enable easy installation of front facing sensors 202 to detect ambient threat 112 coming in the direction of a security personnel (e.g., wearer 114 of the tactical vest 104) from front. Also, the sensor cavity 2002C in the back area 214 of the tactical gear 104 may allow installation of a rear facing sensor 206 to detect ambient threat 112 coming in the direction of the security personnel (e.g., wearer 114 of the tactical vest 104), thereby activating the haptic feedback device 210 in the back area 214 to alert the wearer of the ambient threat 112 coming from rear, according to one embodiment.

In a combat zone, a soldier wearing the GovGPT DragonFly™ may receive an alert through a rapid vibration on their left arm, indicating a possible IED ahead to their left, according to one embodiment. Simultaneously, a patterned vibration on their back may suggest incoming indirect fire from behind, according to one embodiment. In an alternative embodiment, a shoulder-based 360-degree panoramic camera may be used. This multifaceted feedback allows the soldier to quickly assess the situation and make informed decisions, drastically increasing situational awareness and reaction times, according to one embodiment.

The components of the GovGPT DragonFly™ might include:

Haptic Display Suit: A lightweight, durable suit equipped with numerous haptic feedback modules, according to one embodiment. These modules may be strategically placed at key points on the body to provide accurate and immediate tactile feedback, according to one embodiment.

Central Processing Unit (CPU): A compact, yet powerful AI-driven CPU may be embedded within the suit, according to one embodiment. This unit may process sensor data, runs threat detection algorithms, and generates appropriate haptic feedback signals, according to one embodiment.

Communication Module: Integrated into the CPU, this module may ensure constant connectivity with command centers, databases, and other team members for real-time intelligence and coordination, according to one embodiment.

Near-Field Wireless System Network: The system may use a non-radiative, human-body-centered communication network to integrate haptic suit components.

Power Supply: The system may be powered by a lightweight, high-capacity battery designed for extended field use with options for solar charging or wireless recharging, according to one embodiment.

A preferred embodiment of the GovGPT DragonFly™ with water-resistant Wi-R technology and an automatic fallback mechanism can be highly advantageous in challenging environments, according to this embodiment. The body worn safety device may communicate without electronic signature through a non-radiative, human-body-centered communication network using Wi-R technology. Wi-R technology may provide body conduit communication, such that there is no electronic signature around the weare (see: (ttps://ixana.ai/). In this embodiment, Wi-R can transmit 10× higher data rate than Bluetooth (up to 30 Mbps demonstrated) to transfer video and multi-sensor data, according to one embodiment. In this embodiment, the haptic feedback modules can be battery-free without severe duty cycling, according to one embodiment. This can be achieved when the Wi-R components are encased in water-resistant materials, such as silicone or specialized polymers, ensuring functionality in wet conditions, including heavy rain, or brief submersions, according to this embodiment. All connectors and ports are designed with watertight seals to prevent water ingress, according to this embodiment. Electronic parts are coated with hydrophobic substances to repel water and protect against corrosion, according to this embodiment. The system includes sensors that detect water exposure beyond a certain threshold or compromise in integrity (like a breach in the casing), according to this embodiment. Upon detection, it automatically switches to a dormant mode to protect sensitive electronics, according to this embodiment. In dormant mode, the system conserves power by shutting down non-essential functions, according to this embodiment. It activates a fallback power source, like a secondary battery or supercapacitor, to maintain critical operations, according to this embodiment.

Essential functions, like basic communication or location tracking, remain operational, ensuring the user is still connected and locatable, according to this embodiment. Once the system detects that it is in a safe, dry environment again, it automatically reactivates full functionality, according to this embodiment. The user can manually override the dormant mode if necessary, depending on the operational requirements, according to this embodiment. The water-resistant feature makes the system more durable and versatile, suitable for amphibious or maritime operations, according to this embodiment. The automatic transition to dormant mode and fallback power ensures the system remains reliable even if the primary power source is compromised, according to this embodiment. The ability to maintain critical functions in adverse conditions enhances the safety and operational security of the personnel using the system, according to this embodiment. This embodiment of the GovGPT DragonFly™ can be particularly beneficial for special forces, maritime operations, and disaster response teams where exposure to water and challenging environments is common, according to this embodiment The GovGPT DragonFly™ may include threat detection algorithms that use AI to analyze data from a generative artificial intelligence body worn artificial intelligence apparatus and/or external sources (like drones, satellites, or ground intelligence) to identify potential threats, according to one embodiment. In addition, the GovGPT DragonFly™ may include Adaptive Haptic Feedback to provide intuitive and varied haptic signals based on the nature and proximity of the detected threat, according to one embodiment. For instance, a rapid pulsing may indicate an imminent IED threat, while a directional vibration may signal sniper fire, according to one embodiment. Sensors may detect environmental hazards, such as extreme temperatures or toxic agents, and alert the wearer through distinct haptic patterns to provide a police officer or soldier with environmental awareness, according to one embodiment.

In stealth operations, the apparatus may switch to a mode that minimizes electronic emissions and uses subtle haptic cues to communicate, according to one embodiment. In one embodiment, integrated biometric sensors may monitor the wearer's vital signs, providing health alerts and stress level assessments, according to one embodiment. The AI may adapt to the wearer's responses and fine-tune its alert system for personalized effectiveness, according to one embodiment. The generative artificial intelligence body-worn apparatus can interface with other military tech like drones, night vision, or mapping tools, integrating their data into its threat assessment, according to one embodiment.

Placing haptic feedback modules on a person, especially in a tactical context like the GovGPT DragonFly™, requires strategic positioning to maximize effectiveness and ensure the wearer remains comfortable and mobile, according to one embodiment.

Here's an outline of potential locations for these feedback modules:

Head/Neck Area: Haptic feedback modules here may alert the wearer to overhead threats or advise when to look up, according to one embodiment. They may be integrated into a helmet or a collar, according to one embodiment.

Shoulders: Ideal for indicating the direction of a threat or an objective, according to one embodiment. For instance, a tap on the right shoulder may mean a threat or point of interest to the right, according to one embodiment.

Upper Arms: Useful for indicating lateral threats or directions, according to one embodiment. They may also vibrate to suggest arm movements, like raising a weapon or blocking, according to one embodiment.

Wrists/Hands: Haptic feedback modules here may provide detailed feedback for tasks requiring precision, like defusing a bomb or handling sensitive equipment, according to one embodiment. Vibrations here may also remind the user to check their handheld devices or weapons, according to one embodiment.

Chest and Back: Large arrays of haptic feedback modules here are useful for more general alerts, such as a rapid heartbeat pattern indicating danger or a gentle wave-like motion for a cautionary alert, according to one embodiment. The back can also be used to indicate threats from behind, according to one embodiment.

Waist: Haptic feedback modules around the waist can be used to direct the wearer to turn left or right, or to move forward or backward, according to one embodiment. This may be critical for navigation or spatial orientation in low-visibility situations, according to one embodiment.

Thighs and Knees: Ideal for suggesting movement or crouching, according to one embodiment. A vibration on the front of the thigh may indicate the need to advance, while a vibration on the back may mean to retreat or take cover, according to one embodiment.

Ankles/Feet: Alerts here may indicate dangers on the ground, like tripwires or IEDs, or suggest when to stop or change walking speed, according to one embodiment.

Considerations for Haptic Feedback Module Placement:

Ergonomics: The haptic feedback modules must be placed in a way that does not impede movement or cause discomfort during extended wear, according to one embodiment.

Intuitive Responses: Placement should be intuitive, so the wearer can quickly and subconsciously understand and react to the feedback, according to one embodiment.

Environmental Factors: The haptic feedback modules should be robust enough to withstand various environmental conditions, like water, dirt, and extreme temperatures, according to one embodiment.

Discretion: For covert operations, the feedback modules should not be visible or easily detectable, according to one embodiment.

Customization: The system may allow for customization of feedback module placement based on user preference or specific mission requirements, according to one embodiment.

Besides haptic feedback modules, there are several other types of alerting mechanisms that can be integrated into advanced wearable systems like the GovGPT DragonFly™ to enhance situational awareness and safety, according to one embodiment. Each type of alert has its own advantages and can be used in different scenarios:

Auditory Alerts:

Earbuds or Bone Conduction Headphones: Delivering auditory information directly to the user without obstructing external sounds, according to one embodiment.

Directional Sound Alerts: Sounds that appear to come from the direction of the threat, helping in quick spatial orientation, according to one embodiment.

Visual Alerts:

Heads-Up Display (HUD) in Glasses/Visor: Displaying critical information like maps, threat locations, or health stats in the user's field of vision, according to one embodiment.

LED Indicators: Small lights on the suit or equipment that can change color or blink to signal different alerts or statuses, according to one embodiment.

Tactile Alerts:

Texture Change: Certain parts of the wearable may change texture (e.g., becoming rough or smooth) to convey messages or warnings, according to one embodiment.

Pressure Feedback: Parts of the wearable may include a number of actuators that apply various pressures on the skin of the wearer to convey information on varying intensities and patterns of signals, according to one embodiment.

Vibrotactile Feedback: Localized vibration alerts in parts of the wearable may be used for less specific, but urgent alerts, according to one embodiment.

Electrotactile Feedback: Electrodes placed on various areas on the surface of the skin can electrically stimulate nerves to convey information and provide warnings, according to one embodiment.

Mechano-Tactile Feedback: Certain parts of the wearable may brush or tap on the surface of the skin to provide sensory feedback on the location or threats and convey messages, according to one embodiment.

Thermal Feedback: Changes in the suit's temperature in certain areas to signal different types of alerts, like a warming sensation for caution or a cool patch for a need to remain alert and focused, according to one embodiment.

Electrical Muscle Stimulation (EMS):

Muscle Activation: Very mild electrical stimulation can be used to prompt muscle groups to react, guiding movement or alerting to danger, according to one embodiment.

Voice Alerts:

AI-Powered Voice Assistant: Providing verbal warnings or suggestions, especially useful in complex scenarios where detailed information is needed quickly, according to one embodiment.

These diverse alerting mechanisms can be employed singularly or in combination, depending on the context and requirements of the mission, according to one embodiment. The key is to ensure that the alerts are intuitive, non-intrusive, and enhance the user's ability to respond effectively to various situations, according to one embodiment.

The GovGPT DragonFly™ System is an innovative solution designed to revolutionize the way law enforcement and security professionals utilize body-worn camera technology, according to one embodiment. This cutting-edge system seamlessly integrates advanced camera capabilities into a police gear, offering unprecedented flexibility, comfort, and functionality, according to one embodiment. The DragonFly™ system is built on a modular framework, allowing for easy customization and upgrades to meet the evolving needs of modern policing and security operations, according to one embodiment.

The invention described is a modular tactical gear designed to enhance the efficiency and flexibility of equipment use, particularly suited for scenarios requiring mobility and adaptability, according to one embodiment.

The core innovation revolves around integrating a camera and haptic feedback device into the gear, ensuring that these components are seamlessly incorporated without disrupting the wearer's existing workflow, according to one embodiment. Key features of this invention include:

Camera Integration: The gear houses a camera, allowing for hands-free operation and eliminating the need for manual handling and mounting of traditional cameras, according to one embodiment. This integration supports continuous recording without the need to detach and reattach the device, according to one embodiment.

Haptic Feedback Device: Vibration modules are optionally embedded within the gear to provide tactile feedback or alerts, enhancing situational awareness and operational efficiency, according to one embodiment.

Modular Battery Packs with SIM and SD Card Slots: A distinctive aspect of this invention is the detachable battery pack, which incorporates a SIM card for connectivity and an SD card for storage (or future non-volatile or volatile storage means), according to one embodiment. This modular approach allows for easy swapping of battery packs, facilitating extended use without the need for frequent recharging or data transfer interruptions, according to one embodiment.

Magnetic Attachment and Electrical Coupling: The detachable components, such as battery packs and optional processing units, are designed to attach magnetically to the gear, according to one embodiment. This design ensures secure attachment while allowing for easy removal and replacement, according to one embodiment. The magnetic attachment also enables electrical coupling, ensuring that power and data are seamlessly integrated across the modular components, according to one embodiment.

Optional Processing Power Upgrade: An additional module can be attached to enhance the gear's processing capabilities, potentially transforming the gear into a powerful computing platform, according to one embodiment. This modular processor can support advanced functions, analytics, or real-time data processing, further extending the gear's utility, according to one embodiment.

Charging existing Body Cameras: The GovGPT DragonFly™ battery pack is capable of charging USB-C or similar connector body cameras (e.g. such as Axon® Body 4), mobile phones and other existing portable devices, as it effectively serves as a battery storage capacitor, according to one embodiment. This means officers only need to charge one battery, without the need to remove their Axon® cameras for charging. DragonFly™'s battery pack serves as a universal energy base for all connected devices, offering convenience and efficiency, according to one embodiment. This innovation streamlines equipment management, ensuring officers remain fully charged and ready, according to one embodiment.

In other words, the DragonFly™'s battery pack acts as a universal power hub, capable of charging multiple devices simultaneously, according to one embodiment. This eliminates the need for officers to manage and charge multiple batteries for different devices, simplifying the charging process and reducing equipment downtime, according to one embodiment. By serving as the energy base for connected devices, the DragonFly™'s battery pack ensures that all equipment remains charged and operational, according to one embodiment. This feature is vital for long shifts or operations where access to charging facilities is limited, according to one embodiment. Officers can trust their devices to last through their duties, providing peace of mind and allowing them to focus on their essential responsibilities, according to one embodiment.

The GovGPT DragonFly™'s battery pack innovation closely mirrors the concept of a portable charging capacitor commonly used for mobile phones, but it's tailored specifically for the rigorous demands of law enforcement equipment, according to one embodiment. Incorporating such a portable and efficient charging solution addresses a critical need for law enforcement operations that extend over long hours or across vast areas, according to one embodiment. The battery pack ensures that all connected devices can be kept charged and ready, providing a reliable power source that supports continuous operation, according to one embodiment. This operational efficiency is crucial in situations where every second counts and equipment readiness can make a significant difference in outcomes, according to one embodiment.

Eco-Friendly and Cost-Effective: Reducing the need for multiple chargers and batteries not only simplifies logistics but also promotes a more eco-friendly approach to equipment management, according to one embodiment. By consolidating charging solutions, law enforcement agencies can decrease electronic waste and lower the costs associated with maintaining a wide array of charging equipment and batteries, according to one embodiment.

Wireless Charging Compatibility: To simplify recharging, the gear and its components can be designed to support wireless charging, reducing the need for physical connectors and facilitating easier maintenance and readiness, according to one embodiment.

Robustness and Durability: The design emphasizes the need for the gear and its components to withstand operational demands, ensuring that attachments remain secure under various conditions, according to one embodiment.

This invention aims to revolutionize the way tactical equipment is utilized, offering unprecedented modularity, flexibility, and efficiency, according to one embodiment. By disaggregating essential components such as the camera, battery, and processing power, the gear allows for tailored configurations to meet specific operational needs, according to one embodiment. This modular approach not only enhances operational effectiveness but also reduces downtime associated with equipment maintenance and data management, according to one embodiment. The invention's potential applications span various fields, including law enforcement, military operations, and any scenario requiring robust, flexible, and efficient mobile equipment solutions, according to one embodiment.

Access Control

The addition of optional advanced user authentication methods to the modular tactical gear introduces a new layer of security and personalization, ensuring that only authorized users can access and utilize the gear's functionalities, according to one embodiment. These methods are designed to work in harmony with the gear's existing modular design, leveraging integrated sensors and components for multifaceted authentication, according to one embodiment.

Authentication might work with a number of methods, described here:

Voice Recognition: Utilizes an ambient sensor to recognize the user's voice pattern, according to one embodiment. The gear activates or unlocks its functionalities when it detects a pre-registered voice pattern, ensuring secure and personalized access, according to one embodiment.

Fit Detection: Employs sensors integrated into the gear to detect the fit on the person, considering factors like size and shape, according to one embodiment. Authentication based on how the gear fits the user, providing a unique method of ensuring that the gear is used by the intended person, according to one embodiment.

Fingerprint Recognition: Incorporates a fingerprint sensor on the gear or the detachable battery pack, allowing users to authenticate by touching the sensor, according to one embodiment.

Biometric Patterns and Rhythms: Considers unique individual biometrics such as heartbeat, breathing rate, and possibly walking patterns through integrated sensors, according to one embodiment. These methods offer high-security access control, ensuring that only the user with matching biometric data can use the gear, according to one embodiment.

Gait Analysis: Utilizes gyroscopes or similar sensors to analyze the user's walking pattern and speed, according to one embodiment. The gear can learn and recognize the user's gait, providing a non-intrusive and continuous form of authentication, according to one embodiment.

Front and Back Cameras for Facial Recognition: Incorporates cameras capable of capturing images in a 360-degree range, potentially including facial recognition capabilities, according to one embodiment. Enables authentication by recognizing the user's face, offering a secure and convenient access method that can be passively implemented as the user wears the gear, according to one embodiment.

Modular Component Authentication: The modular design allows for authentication mechanisms to be part of the detachable components, such as the battery pack with SIM and SD card slots, according to one embodiment. This can include embedding biometric sensors into these components, according to one embodiment. This can ensure that the gear and its functionalities are only operational when authenticated modules are attached, adding an additional layer of security and personalization.

These embodiments enhance the tactical gear's security by ensuring that its advanced functionalities are accessible only to authorized users, according to one embodiment. The inclusion of multiple authentication methods caters to varying operational requirements and user preferences, providing flexibility in securing the gear while maintaining its modular and adaptive design, according to one embodiment. The integration of these security features underscores the gear's potential as a highly personalized, secure, and efficient tool for various applications, including military, law enforcement, and specialized civilian use, according to one embodiment.

The invention designed to overcome the limitations of bulky and cumbersome body cameras is a modular body camera system integrated directly into police officers' gears, according to one embodiment. This innovative system features a base module embedded within the gear itself, onto which various kinds of sensors and processing power chips can be easily interchanged depending on the operational requirements or advancements in technology, according to one embodiment.

The core of this invention lies in its modularity and flexibility, according to one embodiment. Sensors can range from standard video recording cameras to advanced sensors capable of night vision, thermal imaging, or even biometric scanning. Similarly, the processing chips can be upgraded to enhance data processing capabilities, storage capacity, or battery life.

The visual sensor may be a front-facing visual sensor embedded in a flush manner in a shoulder area of the tactical gear such that movement of a tactical rifle is not impeded by the visual sensor. The body worn safety device may not permanently store real-time threat analysis.

One of the key benefits of this system is its seamlessness and convenience, according to one embodiment. Officers no longer need to worry about attaching a bulky camera unit to their uniforms or the hassle of removing it for recharging or data download, according to one embodiment. The camera system is always on and ready whenever they wear their gear, significantly reducing preparation time and ensuring continuous operation throughout their shift, according to one embodiment.

Recharging and data transfer can be streamlined through wireless technologies, according to one embodiment. For instance, when an officer enters a designated area, such as the police station or a vehicle equipped with the necessary infrastructure, the gear can automatically start charging and uploading the recorded data to a secure server without any physical intervention required, according to one embodiment. For example, the back of the gear can be electronically coupled with a chair in a patrol vehicle to enable wireless charging, according to one embodiment.

In this specific embodiment, the system is equipped with a wireless charging capability that activates when an officer sits in a car, allowing the battery pack integrated into the back of the gear to charge wirelessly, according to one embodiment. This feature addresses one of the key operational challenges with portable electronic devices: ensuring that they are always charged and ready for use without necessitating manual intervention for charging, according to one embodiment. Embedded within the gear, particularly in the back area where it is least obtrusive to the wearer, is a wireless charging receiver, according to one embodiment. This module is designed to capture energy from a wireless charging transmitter installed in the officer's vehicle seat, according to one embodiment. The vehicle's seat is equipped with a wireless charging transmitter that connects to the vehicle's electrical system, according to one embodiment. When the vehicle is started, or when it's in operation, the transmitter is activated, creating an electromagnetic field capable of transferring power wirelessly to the receiver in the gear, according to one embodiment.

The system includes a smart charging management circuit within the gear that regulates the charging process, according to one embodiment. This circuit ensures that the battery is charged efficiently and safely, preventing overcharging and optimizing battery life, according to one embodiment. It also intelligently prioritizes power distribution to different modules based on their current energy needs and usage patterns, according to one embodiment. The gear incorporates a high-efficiency, lightweight battery pack designed for quick recharging and extended use, according to one embodiment. This battery not only powers the camera and sensors but also ensures that the system's processing and communication capabilities are maintained, according to one embodiment. Officers no longer need to remove their gears and manually dock them for charging, according to one embodiment. The charging begins automatically when they sit in their vehicle, ensuring the camera system is always ready for use, according to one embodiment. This automatic, in-vehicle charging capability significantly reduces the risk of camera systems running out of power during critical moments, enhancing overall operational readiness and reliability, according to one embodiment.

The embodiment allows for the camera system to be used continuously without the need for officers to take breaks for charging, thereby ensuring uninterrupted recording and data collection, according to one embodiment. By eliminating the need for manual charging processes, this feature adds to the overall comfort and convenience of the system, making it more user-friendly and acceptable to officers, according to one embodiment.

This embodiment exemplifies GovGPT's advanced DragonFly™ technology to solve practical challenges faced by law enforcement personnel, according to one embodiment. It ensures that officers are not bogged down by the logistics of keeping their equipment charged, allowing them to focus on their primary duties with the assurance that their body camera system is always operational, according to one embodiment.

This invention not only addresses the ergonomic and operational challenges posed by traditional body cameras but also offers enhanced flexibility and future-proofing, allowing law enforcement agencies to adapt to technological advancements without needing to replace the entire body camera system, according to one embodiment.

In an advanced embodiment of the DragonFly™ System, the wireless charging feature is complemented by wireless data transfer capabilities, further enhancing the system's functionality and convenience for law enforcement and security personnel, according to one embodiment. This dual-function system allows not only for the battery pack integrated into the gear to be charged wirelessly when an officer sits in a car but also enables the automatic wireless synchronization of data between the gear's storage module and a secure data storage system within the vehicle or at the police station, according to one embodiment. Alongside the wireless charging receiver, the gear is equipped with wireless communication technology, such as Wi-Fi or Bluetooth, enabling the automatic transfer of data when the charging process is initiated, according to one embodiment. This ensures that all recorded data from the cameras and sensors is backed up securely and efficiently without manual intervention, according to one embodiment.

The vehicle is outfitted with a corresponding data relay system that not only transmits power wirelessly to the gear but also serves as a conduit for data transfer, according to one embodiment. This system is connected to the vehicle's onboard computer or a dedicated module that securely communicates with the law enforcement agency's data network, according to one embodiment. The system includes sophisticated data management software that automatically initiates data synchronization when the wireless charging connection is established, according to one embodiment. It intelligently manages data transfer, ensuring that new and unbacked-up data is prioritized and securely transmitted to the agency's central data storage or cloud-based system, according to one embodiment. To protect sensitive information, all data transferred wirelessly is encrypted using advanced encryption standards, according to one embodiment. This ensures that any data captured by the gear's cameras and sensors remain secure from unauthorized access during transmission and storage, according to one embodiment.

This embodiment significantly streamlines the process of data management for officers and administrative staff, according to one embodiment. By automating data transfer along with charging, it ensures that video footage and sensor data are always up to date and readily available for review or evidence without requiring physical docking stations or manual uploads, according to one embodiment. Automatic wireless data transfer minimizes the risk of data loss or delays in uploading important footage, according to one embodiment. It ensures that data is backed up regularly and consistently, improving the integrity and availability of evidence for investigative and judicial processes, according to one embodiment. The dual wireless charging and data transfer capability free up officers from administrative tasks related to equipment management, allowing them to focus more on their core responsibilities, according to one embodiment. This efficiency gain not only benefits the officers on the ground but also streamlines back-office operations, according to one embodiment. With automatic, encrypted data transfers, the system helps law enforcement agencies maintain high standards of data security and compliance with legal requirements regarding the handling of evidence and personal information, according to one embodiment.

This advanced embodiment of the DragonFly™ System represents a significant leap forward in the usability and functionality of body-worn camera systems, offering law enforcement personnel a highly efficient, secure, and user-friendly solution for managing both the power needs and data integrity of their essential equipment, according to one embodiment.

Expanding on the concept of the modular body camera system integrated into police gears, this invention is designed to revolutionize how law enforcement officers capture, store, and manage video footage and other data during their patrols, according to one embodiment. The system is built around a lightweight, durable, and flexible base module embedded within the officer's gear, according to one embodiment. This module acts as the central hub for a variety of interchangeable components, including a range of sensors and processing units, tailored to the needs and challenges of modern policing, according to one embodiment.

Key Features and Innovations

Interchangeable Sensors: Beyond standard high-definition video cameras, the system can be equipped with modular infrared sensors for night vision, thermal imaging cameras for search and rescue operations in low visibility conditions, and body sensors to monitor the health and stress levels of the officer, according to one embodiment. This versatility ensures that officers are equipped with the right tools for any scenario, according to one embodiment.

Advanced Processing Units: These can be swapped to enhance specific functionalities, such as facial recognition software for identifying suspects in real-time, encryption modules for securing sensitive data, and AI-driven analytics to flag important events automatically. The processing units are designed for easy upgrades, ensuring the system remains at the cutting edge of technology, according to one embodiment.

Seamless Connectivity: Utilizing the latest in wireless technology, including 5G and Wi-Fi 6, the system ensures uninterrupted data transmission to central servers, facilitating real-time sharing of video and sensor data with command centers and other units, according to one embodiment. This connectivity also supports remote activation or deactivation of specific sensors, allowing command centers to tailor the data collection based on evolving situations, according to one embodiment.

Effortless Recharging and Data Syncing: With wireless charging capabilities, officers can recharge the system simply by entering a vehicle or station equipped with a charging mat or dock, according to one embodiment. Similarly, data syncing happens automatically, minimizing the need for manual intervention and ensuring all recorded data is securely backed up without delay, according to one embodiment Ergonomic and Comfortable Design: Despite its advanced capabilities, the system is designed to be as unobtrusive and comfortable as possible, according to one embodiment. The integration into the gear distributes the weight evenly across the officer's torso, avoiding the discomfort associated with traditional body cameras, according to one embodiment. The materials used are breathable, water-resistant, and durable, suitable for the various environments officers find themselves in, according to one embodiment.

Benefits

Increased Officer Safety and Efficiency: With hands-free operation and automatic data management, officers can focus more on their immediate surroundings and less on managing their equipment, according to one embodiment. Real-time data transmission can also provide command centers with valuable information to support officers in the field more effectively, according to one embodiment.

Enhanced Transparency and Accountability: Continuous, automatic recording ensures that all interactions and incidents are captured, providing clear evidence for investigations and increasing public trust in law enforcement, according to one embodiment.

Future-Proof: The modular nature of the system means that it can easily adapt to future technological developments, extending its lifecycle and providing better return on investment compared to traditional body cameras, according to one embodiment.

Customizable for Different Missions: The ability to swap sensors and processors means the system can be quickly reconfigured for a wide range of law enforcement activities, from routine patrols to specialized operations like search and rescue or surveillance, according to one embodiment.

This modular body camera system signifies a leap forward in law enforcement technology, combining innovation in wearable tech with the practical needs of modern policing to create a solution that is not only more effective but also more adaptable and user-friendly than existing body cameras, according to one embodiment.

Enhancing the modular tactical gear invention further involves incorporating a variety of sensors tailored to specific operational roles, along with a unique customization and integration strategy, according to one embodiment. This approach aims to address diverse needs across different fields, such as firefighting, law enforcement, and military operations, according to one embodiment:

Flexibility in Sensor Placement: Sensors can be integrated into different parts of the gear depending on the user's role and operational needs, according to one embodiment. For example, firefighters might require thermal sensors placed strategically to monitor temperatures, while law enforcement may benefit from night vision capabilities, according to one embodiment.

Modular Sensor Ports: The gear can feature magnetic ports at various locations, allowing users to attach and detach sensors as needed, according to one embodiment. This modularity supports customization and adapts to a wide range of missions and environmental conditions, according to one embodiment.

Thermal Sensors for Firefighters: Integrating thermal sensors or enhancing compatibility with existing thermal imaging devices (like thermal guns) used by firefighters, according to one embodiment. This can allow them to assess heat sources without needing additional equipment, according to one embodiment.

Night Vision and Auditory Sensors: For operations in low-light conditions or environments where auditory sensing is crucial, integrating night vision sensors and sensitive microphones can provide enhanced situational awareness, according to one embodiment.

Compatibility with Current Equipment: The system can be designed to integrate or enhance existing tools (like radios or thermal guns) without requiring additional bulk, according to one embodiment. This can be achieved by embedding compatible technologies within the gear or creating interfaces that allow existing devices to connect seamlessly with the gear's system, according to one embodiment.

Enhancing the modular tactical gear with optimized camera placement and integrated communication features addresses both situational awareness and communication needs in various operational environments, according to one embodiment. This approach leverages strategic camera positioning and incorporates audio capabilities to ensure comprehensive coverage and efficient communication for the user, according to one embodiment.

Optimal Camera Placement

Front and Back Cameras: To ensure 360-degree coverage and situational awareness, cameras are ideally placed on the front and back of the gear, according to one embodiment. This configuration captures both forward-facing views and potential threats from behind, ensuring no blind spots, according to one embodiment.

Shoulder-Mounted Cameras: Adding shoulder mounts for cameras can provide an elevated viewpoint, offering broader coverage and angles that are impossible with only front and back cameras, according to one embodiment. Shoulder mounts also facilitate a panoptic view, crucial for operations requiring full environmental awareness, according to one embodiment.

Audio Integration

Stereo Microphones: Integrated microphones along with the cameras can enable stereo audio capture, enhancing the situational context provided by video footage, according to one embodiment. This setup can be essential for operations in visually obstructed environments, according to one embodiment.

Speaker and Microphone for Communication: Incorporating a speaker and microphone system enables direct communication without the need for an external radio, according to one embodiment. This system can be optimized to work in noisy environments, such as firefighting scenarios, by using noise-cancellation technologies and positioning the microphone close to the mouth while minimizing interference, according to one embodiment.

Sensor Integration

Visual and Audio Sensors: The gear can include various sensors, such as smoke detectors or thermal sensors, alongside visual and audio capture devices, according to one embodiment. This multi-sensor approach provides a rich data set for situational analysis and decision-making, according to one embodiment.

Microphone Placement for Radio Communication: Considering the operational habits of users, such as how and where they carry and use their radios, the gear can incorporate a microphone positioned to capture voice commands clearly when the user is speaking into the radio, according to one embodiment. This can be near the chest or shoulder, where a radio is typically worn or held, according to one embodiment.

Design Considerations

Modular Design for Customization: The gear maintains a modular design, allowing users to customize sensor and camera placements based on their operational needs, according to one embodiment. This flexibility ensures that the gear can adapt to a wide range of missions and user preferences, according to one embodiment.

Ergonomics and Comfort: While enhancing the gear with additional capabilities, it's crucial to consider the ergonomics and comfort of the wearer, according to one embodiment. The design should not restrict movement or add unnecessary bulk, ensuring that the gear remains practical for extended use in various conditions, according to one embodiment.

Communication and Control

Integrated Control System: An integrated system that allows the user to control camera angles, focus, and zoom directly from the gear can enhance operational efficiency, according to one embodiment. This system can be voice-activated or accessible through a simple touch interface on the gear, according to one embodiment.

Real-Time Data Transmission: Utilizing the SIM card for connectivity, the gear can transmit video, audio, and sensor data in real time, enabling remote monitoring and command center support during operations, according to one embodiment.

These enhancements to the modular tactical gear aim to provide a comprehensive solution that addresses both the visual and auditory aspects of situational awareness and communication, according to one embodiment. By carefully considering the placement and integration of cameras and audio components, alongside ergonomic design and modular flexibility, the gear represents a significant advancement in tactical and operational gear, designed to meet the complex demands of modern operational environments, according to one embodiment.

Enhanced Operational Efficiency: By allowing for the integration of role-specific sensors and the compatibility with existing equipment, users can perform their duties more effectively, with all necessary tools integrated into a single wearable platform, according to one embodiment.

Personalization and Flexibility: The ability to customize the gear online and easily modify its configuration on the field ensures that each user has equipment perfectly suited to their needs and mission parameters, according to one embodiment.

The modular body camera system integrated into police gears can not only addresses the operational and ergonomic challenges of traditional body-worn cameras but also can introduce a range of additional benefits that extend its utility and impact:

Holistic Incident Reconstruction: The ability to integrate data from various sensors (video, audio, biometric, environmental) allows for a more comprehensive reconstruction of incidents, according to one embodiment. This can be invaluable in complex investigations, providing a multi-faceted perspective that goes beyond standard video footage, according to one embodiment.

Real-time Feedback for Training: The system can be used in training scenarios to provide real-time feedback to officers, according to one embodiment. For example, biometric sensors can help in stress management training, while video analytics can be used to review and improve tactical decisions, according to one embodiment. Optional sensors and option can include:

Performance Analysis: Data collected over time can be analyzed to identify patterns in behavior, decision-making, and tactics, offering insights that can be used to enhance overall police performance and effectiveness, according to one embodiment.

Transparency and Engagement: The comprehensive recording capabilities of the system can play a crucial role in enhancing transparency, thereby building public trust, according to one embodiment. Making footage available for public review (while respecting privacy concerns) can demystify police operations and foster community engagement, according to one embodiment.

Evidence for Judicial Processes: High-quality, tamper-proof recordings (with meta-data intact) can provide reliable evidence for courts, reducing the reliance on eyewitness accounts and potentially speeding up judicial processes, according to one embodiment.

Officer Health Monitoring: Biometric sensors can monitor vital signs, alerting command centers to officers in distress due to health issues or physical exertion, according to one embodiment. This feature can save lives by ensuring timely medical intervention, according to one embodiment.

Environmental Hazard Alerts: Environmental sensors can detect hazards such as smoke, toxic gasses, or extreme temperatures, providing early warnings that can prevent harm to officers and the public, according to one embodiment.

Reduced Equipment Overhead: By integrating multiple functions into a single system, agencies can reduce the need for multiple pieces of equipment, lowering costs and simplifying logistics, according to one embodiment.

Lower Training and Maintenance Costs: A standardized system with interchangeable parts simplifies training and maintenance, reducing the resources required to keep the system operational, according to one embodiment.

Adaptability to Various Policing Needs: The modular design allows for customization to fit the specific needs of different units within a police force, from patrol officers to SWAT teams, without requiring completely different equipment, according to one embodiment.

Scalable Deployment: Agencies can start with a basic setup and scale up their capabilities as budgets allow or needs evolve, adding more advanced sensors and processing units over time, according to one embodiment.

Environmental Impact

Reduced Waste: The upgradeable and interchangeable nature of the system components means less electronic waste is generated compared to replacing entire units of traditional body cameras, according to one embodiment.

This modular body camera system represents a forward-thinking approach to law enforcement technology, offering benefits that extend beyond the immediate needs of capturing video footage to enhancing officer safety, operational efficiency, and public trust in a comprehensive and sustainable manner, according to one embodiment.

This expansion of the modular tactical gear invention emphasizes a highly adaptable, user-centered design that can meet the dynamic needs of various professional fields, according to one embodiment. By focusing on customization, sensor integration, and compatibility with existing equipment, the gear represents a significant advancement in personal operational gear, potentially setting a new standard for tactical and professional wearables, according to one embodiment.

DragonFly™'s core innovation lies in its modular approach, enabling users to interchange various sensors and processing chips, according to one embodiment. This flexibility ensures that the system can adapt to a wide range of scenarios, from routine patrols to specialized missions requiring advanced surveillance technology, according to one embodiment. Unlike traditional body cameras, the DragonFly™ system is built into a lightweight, ergonomic gear, distributing weight evenly and reducing the physical burden on the wearer, according to one embodiment. This design minimizes discomfort and fatigue, even over long periods of use, according to one embodiment. The system supports a variety of sensors, including high-definition video cameras, infrared for night vision, thermal imaging, and environmental sensors, according to one embodiment. This array of sensors provides comprehensive situational awareness and enhances the safety and effectiveness of officers on the ground, according to one embodiment.

Equipped with the latest in processing technology, DragonFly™ can offer optional real-time data analysis, facial recognition, and encrypted communications, according to one embodiment. These capabilities ensure that critical information is processed and relayed efficiently, supporting decision-making in the field, according to one embodiment. DragonFly™ utilizes state-of-the-art wireless technology for seamless data transmission and cloud integration, according to one embodiment. This feature enables automatic data syncing and ensures that all recorded information is securely stored and easily accessible for review or evidence, according to one embodiment. The system features advanced battery technology and wireless charging capabilities, eliminating the need for frequent battery replacements or cumbersome charging processes, according to one embodiment. Officers can recharge the system simply by returning to their vehicle or station, without removing their gear or body camera, according to one embodiment. By providing real-time data and analytics, DragonFly™ enhances situational awareness and decision-making, thereby improving officer safety and operational efficiency, according to one embodiment.

The modular nature of the system allows for easy upgrades and customization, ensuring that DragonFly™ remains at the forefront of technology without the need for complete system replacements, according to one embodiment. The gear integration reduces the physical strain on officers, promoting better compliance with body camera policies and improving overall job satisfaction, according to one embodiment.

In an innovative embodiment of the DragonFly™ system, the camera unit is reimagined as a generative GovGPT™ AI pendant, a compact and advanced wearable device that combines the functionalities of a body camera with the capabilities of generative artificial intelligence (AI). This pendant-shaped camera is designed to be worn as part of the officer's uniform, offering a discreet yet powerful tool for recording, analysis, and interaction in a law enforcement context. The AI pendant is sleek and lightweight, designed for comfort and minimal visibility. It can be integrated to the gear (e.g., does not have to be detachable or worn around a neck), blending seamlessly with the officer's uniform.

Paired within the GovGPT™ pendant may be a detachable, integrated, or remotely accessible (e.g., through edge computing or through an Intranet) a generative AI processor that can analyze live video feeds, generate real-time alerts, and even produce synthesized images or videos for various operational purposes, according to one embodiment. Different processors might be possible with differing levels of sophistication. This GovGPT™ AI may support facial recognition, behavior analysis, and can simulate potential outcomes of encounters based on historical data. Despite its compact size, the pendant features a high-definition camera capable of recording in various lighting conditions, ensuring clear and actionable footage is captured at all times, according to one embodiment. Officers can control the device using voice commands, allowing for hands-free operation, according to one embodiment. This feature is particularly useful in situations where manual interaction with the device is impractical or unsafe, according to one embodiment.

Similar to the broader DragonFly™ system, the GovGPT™ pendant supports wireless charging and automatic data transmission, according to one embodiment. When the officer returns to their vehicle or a designated station, the pendant charges and syncs data without the need for cables or manual uploads, according to one embodiment. The generative AI can provide officers with real-time insights and alerts, enhancing their situational awareness, according to one embodiment. For example, it can identify known suspects in a crowd or alert the officer to potentially dangerous behaviors or situations, according to one embodiment. By analyzing real-time data and referencing historical incidents, the AI pendant can offer decision support to officers, suggesting actions that have historically led to peaceful resolutions in similar situations, according to one embodiment.

The device not only records video but also tags and categorizes footage automatically, streamlining evidence collection and analysis, according to one embodiment. This capability reduces administrative burdens on officers and accelerates the investigation process, according to one embodiment. The pendant's design ensures that it is less conspicuous than traditional body cameras, potentially reducing the escalation of tense situations due to the overt presence of recording equipment, according to one embodiment. The AI pendant can interact with other digital devices and systems, providing a platform for integrated law enforcement operations, according to one embodiment. For instance, it can automatically run checks against databases and communicate with other officers or command centers in real-time, according to one embodiment.

This embodiment of the DragonFly™ system, with the generative AI pendant, represents a leap forward in wearable law enforcement technology and handling pre-assaultive threats, according to one embodiment. It combines advanced recording capabilities with AI-driven analysis and support, offering a versatile, efficient, and discreet tool for modern policing, according to one embodiment. Pre-assaultive threats in police and military contexts refer to verbal, non-verbal, or environmental indicators that suggest an individual or group is likely to initiate a physical attack or aggressive action, according to one embodiment. Recognizing these threats is crucial for law enforcement and military personnel to prevent violence, protect themselves, and diffuse potentially dangerous situations, according to one embodiment. These threats can take various forms, according to one embodiment:

Verbal Threats
  Explicit Threats: Direct statements of intent to harm, such as threats to attack, use weapons, or cause damage.
  Implicit Threats: Indirect statements that suggest a threat without explicitly stating it, such as veiled threats or using aggressive tone or language that suggests hostility.

Non-Verbal Threats
  Body Language: Aggressive stances, clenched fists, fixed stares, or other body movements that indicate readiness for physical aggression.
  Facial Expressions: Expressions of anger, contempt, or other emotions that might precede an assault.
  Gestures: Sudden movements or gestures that can indicate an imminent threat, such as reaching into clothing or a bag where a weapon might be concealed.

Environmental Indicators
  Presence of Weapons: Visible weapons or objects that can be used as weapons increase the risk of assault.
  Numerical Superiority: Being outnumbered by a group showing hostile intent.
  Tactical Positioning: Individuals positioning themselves in a way that can facilitate an assault, such as cornering an officer or soldier or blocking exits.

Situational Awareness
  Understanding and recognizing these pre-assaultive cues require high situational awareness and training. Personnel are trained to notice these signs and use de-escalation techniques, call for backup, or prepare for defensive actions as appropriate. The goal is to address the potential threat before it escalates into actual violence, ensuring the safety of all involved, including the potential aggressor. When issues are detected, the DragonFly™ system activates a haptic response on the wearer alerting them to the issue.

GovGPT DragonFly™ system Aids in Proper Response to Pre-Assaultive Threats

DragonFly™ system underscores the importance of recognizing pre-assaultive threats to enable early intervention and the use of force continuum principles, where force is applied in a measured, appropriate manner depending on the threat level, according to one embodiment. The DragonFly™ system delivers proper response to these indicators is critical to preventing harm and ensuring the safety and security of both the personnel and the public they serve, according to one embodiment. When issues are detected, the DragonFly™ system activates a haptic response on the wearer alerting them to the issue.

GovGPT DragonFly™ System Aids in Proper Response to Mental Health Crisis

The DragonFly™ system underscores the detection of mental health issues using a combination of observation, and interaction artificial intelligence, according to one embodiment. Law enforcement officers often encounter individuals with mental health issues in the course of their duties. Recognizing and appropriately responding to these situations is crucial for ensuring the safety and well-being of all involved. DragonFly™ system's AI model includes best practices of Crisis Intervention Training (CIT) which provides the AI model with the tools and knowledge to recognize signs of mental illness and de-escalate potentially volatile situations safely and effectively, according to one embodiment.

DragonFly™ system's AI model is trained to observe specific behaviors and indicators that may suggest an individual is experiencing a mental health crisis or has underlying mental health issues, according to one embodiment. These observations can include:

Unusual Behavior: Actions that are not typical for the situation, such as talking to oneself, showing extreme paranoia, or exhibiting inappropriate emotional responses.

Signs of Distress: Visible signs of emotional or psychological distress, such as crying, shouting, or expressions of fear or confusion.

Non-Verbal Cues: Body language that may indicate anxiety, depression, or disorientation.

DragonFly™ system's AI model observes direct interaction to gather further information to assess the mental state of an individual, according to one embodiment. For example, DragonFly™ system's AI model observes, according to one embodiment:

Communication: Engaging in dialogue to assess the person's coherence, thought process, and ability to understand the situation.

Questioning: Asking questions to determine the individual's awareness of time and place, their current emotional state, and any immediate needs they may have.

Listening: Paying close attention to what the individual says and how they say it, which can provide valuable insights into their mental health status.

When issues are detected, the DragonFly™ system activates a haptic response on the wearer alerting them to the issue, according to one embodiment.

GovGPT DragonFly™ System Aids in Proper Response to Intoxicated Individuals

Detecting intoxication is a critical aspect of GovGPT DragonFly™ duties, particularly when assessing individuals during traffic stops, public disturbances, or criminal investigations, according to one embodiment. GovGPT DragonFly™ AI model uses a variety of methods and tools to determine if an individual is under the influence of alcohol, drugs, or other substances, according to one embodiment. Here are some key approaches used by GovGPT DragonFly™ AI model, according to one embodiment:

Observation of Physical Symptoms and Behavior

Appearance: Bloodshot eyes, flushed face, and disheveled appearance may indicate intoxication.

Odor: The smell of alcohol on the breath or clothing, or the scent of marijuana, can be a strong indicator of recent use if the GovGPT DragonFly™ AI sensor array includes an optional olfactory sensor, according to one embodiment.

Slurred Speech: Difficulty speaking clearly or coherently detected by GovGPT DragonFly™ AI can be a sign of alcohol or drug impairment, according to one embodiment.

Impaired Motor Skills: Difficulty with balance, coordination, and fine motor skills detected by GovGPT DragonFly™ AI. For example the DragonFly™ AI may observe the individual swaying, stumbling, or having trouble standing still.

Altered Mental State: DragonFly™ AI may observe signs of confusion, difficulty concentrating, or erratic behavior can suggest intoxication.

DragonFly™ AI may observe and evaluate live Field Sobriety Tests (FST)s.

Horizontal Gaze Nystagmus (HGN) Test: DragonFly™ AI may observe the eyes of the individual as they follow a moving object (like a pen) to look for involuntary jerking of the eyes, which can be a sign of alcohol impairment.

Walk-and-Turn Test: When the individual is asked to walk a straight line, heel-to-toe, then turn and walk back, DragonFly™ AI may observe to assess balance, coordination, and the ability to follow directions.

One-Leg Stand Test: When an individual is asked to stand with one foot approximately six inches off the ground and count aloud until instructed to put the foot down, DragonFly™ AI may observe to evaluate balance, coordination, and concentration.

DragonFly™ AI model may be trained on Drug Recognition Experts (DREs) level training. In cases where drug use is suspected, DragonFly™ AI may observe administration of the 12-step protocol that includes physical, mental, and medical examinations to identify drug impairment and determine the category of drugs that may be influencing the individual, to make an assessment.

Observing Driving Behavior

Especially in cases of DUI (Driving Under the Influence), DragonFly™ AI may look for driving behaviors that indicate impairment, such as weaving, erratic braking, failing to obey traffic signals, and driving too slowly or too quickly.

GovGPT DragonFly™ System Aids in Proper Response to Opioid Addiction

Detecting opioid addiction in individuals encountered by police and law enforcement can be challenging due to the complexity of addiction and the variety of opioids that may be involved, ranging from prescription medications like oxycodone and hydrocodone to illegal substances like heroin and synthetic opioids such as fentanyl. However, DragonFly™ AI may observe several signs to identify possible opioid addiction:

Physical Signs and Symptoms

DragonFly™ AI model is trained to recognize physical signs that may indicate opioid use or addiction, according to one embodiment. The model may observe, according to one embodiment:

Pupillary Constriction: DragonFly™ AI model may detect pupils that become pinpoint or very small, even in well-lit conditions to make an evaluation of addicted state, according to one embodiment.

Drowsiness or Sedation: DragonFly™ AI model may detect individuals may appear unusually tired, lethargic, or unable to stay awake, according to one embodiment.

Slowed Breathing: DragonFly™ AI model may detect significantly reduced respiratory rates, leading to shallow or slow breathing, according to one embodiment.

DragonFly™ AI model may detect Flushed Skin: Particularly in the face, according to one embodiment.

Behavioral Indicators

DragonFly™ AI model may detect behavioral changes such as unexplained shifts in mood, ranging from euphoria to aggression or depression, according to one embodiment. DragonFly™ AI model may detect agitation, anxiety, muscle aches, sweating, and nausea.

DragonFly™ AI model may observe paraphernalia (e.g., objects) that indicates opioid use:

Needles or Syringes: For injecting drugs.

Spoons with Burn Marks: Used to heat drugs for injection.

Small Bags or Containers: Often used to hold drugs.

Prescription Bottles: Especially if they are for someone else or if there are multiple bottles from different doctors.

DragonFly™ AI model may be specially trained to identify drug impairment, including opioids, through a series of evaluations that can include examining the individual's physiological responses, behavior, and the environment, according to one embodiment. DragonFly™ AI model may be supplemented with information obtained during an arrest or through accessible medical records may provide evidence of opioid addiction, such as a history of multiple prescriptions for opioids from different doctors (doctor shopping) or previous drug-related offenses, according to one embodiment.

Figure 21:
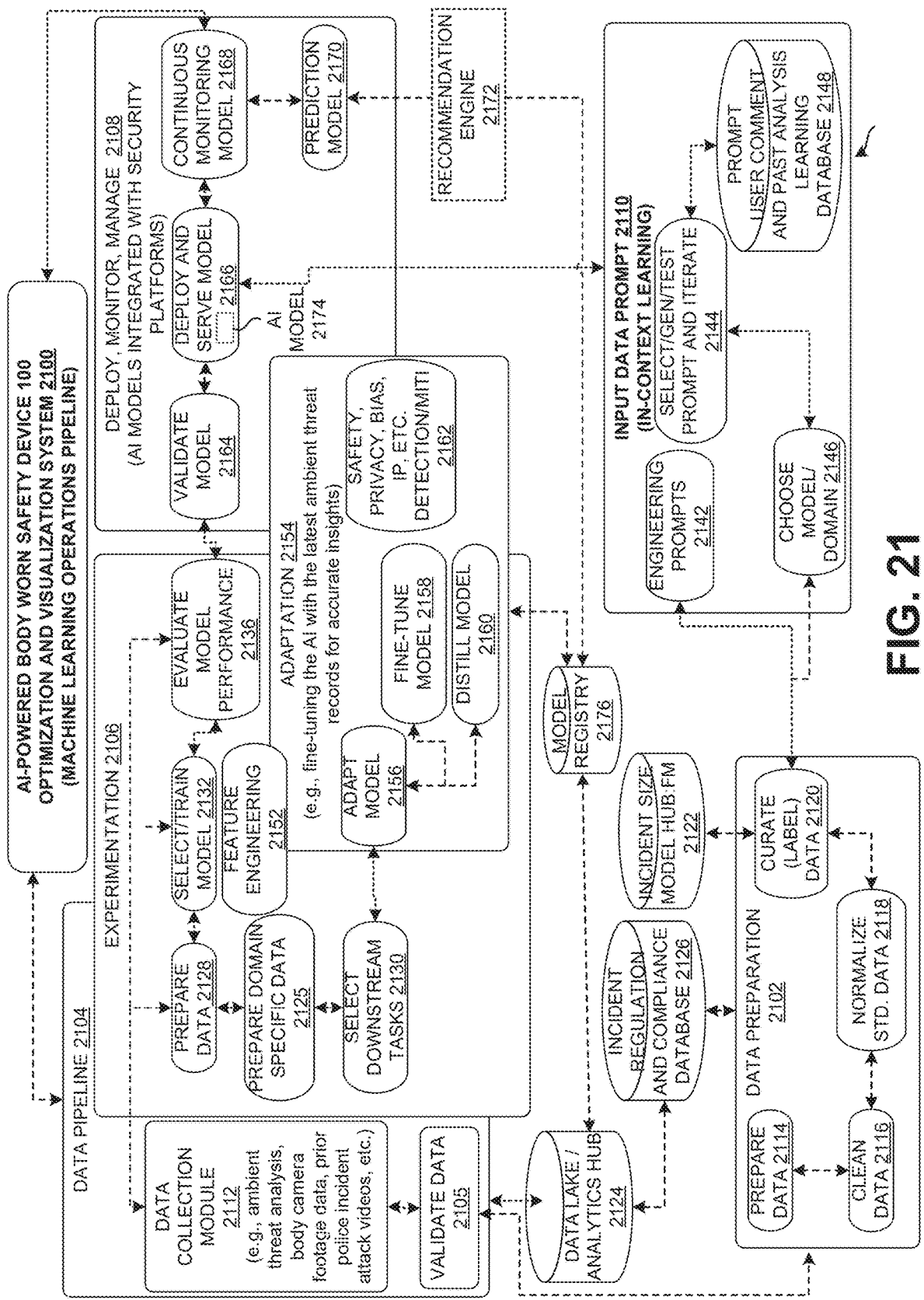
FIG. 21 is a system interaction view that visually represents the intricate process of developing and implementing generative AI models within the body worn safety device of FIG. 1, according to one embodiment.

FIG. 21 is a system interaction view 2150 that visually represents the intricate process of developing and implementing generative AI models within the context of Gov-GPT™ AI-powered body worn safety device 100 optimization and visualization system 2100. The lifecycle of this system ensures that it not only processes and categorizes tactical gear 104 ambient data efficiently but also provides insightful analytics and interactive visualizations to users. Below is a summary of each element:

Data Pipeline 2104: This involves collecting (e.g., using data collection module 2112 of the data pipeline 2104) and validating a wide range of data (e.g., using validate data 2105 of the data pipeline 2104), including the body worn safety device 100 ambient data, captured conversations, and sentiment analysis. The ambient data may include the body camera footage data, the incident sensory data, ambient threat analysis, and the prior police incident attack videos, etc. The data then flows into a data lake or analytics hub 2124 and feature store 2126 for subsequent tasks. In Gov-GPT™ pendant's context, the Data Pipeline 2104 may involve collecting and validating data pertinent to public opinions, pre-incident video data, public record with prior police incident videos of police being attacked by ambient threats, body camera footage, history of crowd dynamics and behavior, etc., according to one embodiment The data preparation 2102 may be the process of preparing raw data extracted from the data lake and/or analytics hub 2124 based on the prompt received from a user so that it is suitable for further processing and analysis by the AI-powered body worn safety device 100 optimization and visualization system 2100. The data preparation 2102 may include collecting, cleaning, and labeling raw data into a form suitable for machine learning (ML) algorithms and then exploring and visualizing the data. The data preparation 2102 phase may include prepare data 2114, clean data 2116, normalize standardized data 2118, and curate data 2120. The prepare data 2114 may involve preprocessing the input data (e.g., received using the data collection module 2112) by focussing on the data that is needed to design and generate a specific data that can be utilized to guide data preparation 2102. The prepared data 2114 may further include conducting geospatial analysis to assess the physical attributes of each incident, etc. In addition, the prepared data 2114 may include converting text to numerical embeddings and/or resizing images for further processing, according to one embodiment.

The clean data 2116 may include cleaning and filtering the data to remove errors, outliers, or irrelevant information from the collected data. The clean data 2116 process may remove any irrelevant and/or noisy data that may hinder the AI-powered optimization and visualization system 2100, according to one embodiment.

The normalize standardized data 2118 may be the process of reorganizing data within a database (e.g., using the data lake and/or analytics hub 2124) of the AI-powered body worn safety device 100 optimization and visualization system 2100 so that the AI model 2174 can utilize it for generating and/or address further queries and analysis. The normalize standardized data 2118 may the process of developing clean data from the collected data (e.g., using the collect data module 2112) received by the database (e.g., using the data lake and/or analytics hub 2124) of the AI-powered body worn safety device 100 optimization and visualization system 2100. This may include eliminating redundant and unstructured data and making the data appear similar across all records and fields in the database (e.g., data lake and/or analytics hub 2124). The normalize standardized data 2118 may include formatting the collected data to make it compatible with the AI model of the AI-powered body worn safety device 100 optimization and visualization system 2100, according to one embodiment.

The curate data 2120 may be the process of creating, organizing and maintaining the data sets created by the normalize standardized data 2118 process so they can be accessed and used by people looking for information. It may involve collecting, structuring, indexing and cataloging data for users of the AI-powered body worn safety device 100 optimization and visualization system 2100. The curate data 2120 may clean and organize data through filtering, transformation, integration and labeling of data for supervised learning of the AI model 2174. Each data in the AI-powered body worn safety device 100 optimization and visualization system 2100 may be labeled based on whether they are suitable for processing. The normalize standardized data 2118 may be labeled based on the incident size model hub 2122 and input data prompt 2110 of the database (e.g., using incident regulation and compliance database 2126), according to one embodiment.

The data lake and/or analytics hub 2124 may be a repository to store and manage all the data related to the AI-powered body worn safety device 100 optimization and visualization system 2100. The data lake and/or analytics hub 2124 may receive and integrate data from various sources in the network to enable data analysis and exploration for optimization and visualization, according to one embodiment.

Experimentation 2106: This phase includes preparing data 2128, engineering features 2152, selecting and training models 2132, adapting the model 2156, and evaluating the model's performance 2136. Experimentation 2106 in GovGPT™ body worn safety device's case can encompass the AI analyzing various ambient scenarios and sensors of the tactical gear 104 to suggest the most prevalent concerns and sentiments, according to one embodiment.

In the adaptation 2154 phase, the machine learning models may adapt and improve their performance as they are exposed to more data by fine tuning (e.g., using the fine-tune model 2158) the adapt model 2156 for a specific threat incident and include additional domain specific knowledge. The adapt model 2156 may modify the model architecture to better handle a specific task. The fine-tune model 2158 may train the model on a curated dataset of high-quality data by optimizing the hyperparameters to improve model performance. The distill model 2160 may simplify the model architecture to reduce computational cost by maintaining and improving model performance. The system may implement safety, privacy, bias and IP safeguards 2162 to prevent bias and discrimination while predicting a threat incident. The system may ensure model outputs are fair and transparent while protecting the sensitive data as well.

Maturity Level 1: Prompt (e.g., using engineering prompts 2142), In-Context Learning, and Chaining: At this stage, a model is selected from the model registry 2176 using the choose model/domain 2146 and prompted (e.g., input data prompt 2110 in-context learning of the data pipeline 2104) to perform a task, according to one embodiment. The responses are assessed and the model is re-prompted using the select/gen/test prompt and iterate 2144 if necessary. In-context learning (ICL) allows the model to learn from examples without changing its weights (e.g., using the prompt user comment and past analysis learning database 2148 in-context learning of the data pipeline 2104). In GovGPT tactical gear 104, Prompt and In-Context Learning can involve prompting the AI with specific ambient and sensor data and learning from past analyses to enhance its predictive capabilities, according to one embodiment.

Chain it: This involves a sequence of tasks starting from data extraction, running predictive models 2170, and then using the results to prompt a generative AI model 2174 to produce an output. In GovGPT tactical gear 104, Chain it can mean applying predictive analytics to ambient signal data to inform civic engagement and policy decisions, according to one embodiment.

Tune it: Refers to fine-tuning the model 2158 to improve its responses. This includes parameter-efficient techniques and domain-specific tuning (e.g., using the prepare domain specific data 2125 and select downstream tasks 2130). In GovGPT™ tactical gear 104, Tune it can involve fine-tuning the AI using the fine-tune model 2158 with the latest ambient data captured from tactical gears deployed, according to one embodiment.

Deploy, Monitor, Manage 2108: After a model is validated (e.g., using the validate model 2164), it is deployed (e.g., using the deploy and serve model 2166), and then its performance is continuously monitored using the continuous monitoring model 2168, according to one embodiment. Deployment in GovGPT™ tactical gear's case can see the AI being integrated into municipal platforms, where it can be monitored and managed as users interact with it for tactical gear 104 ambient data analysis, according to one embodiment.

Maturity Level 3: RAG it & Ground it: Retrieval Augmented Generation (RAG) is used to provide context for the model by retrieving relevant information from a knowledge base, according to one embodiment. Grounding ensures the model's outputs are factually accurate. In GovGPT™ tactical gear 104, RAG and Grounding can be utilized to provide contextually relevant information from civic databases to ensure recommendations (e.g., generated using the recommendation engine 2172 of the data pipeline 2104) are grounded in factual, up-to-date ambient signal and policy data, according to one embodiment.

FLARE it: A proactive variation of RAG that anticipates future content and retrieves relevant information accordingly. In GovGPT™ tactical gear 104, FLARE it can predict future trends in opinion or emerging community concerns that can affect policy-making.

Figure 22:
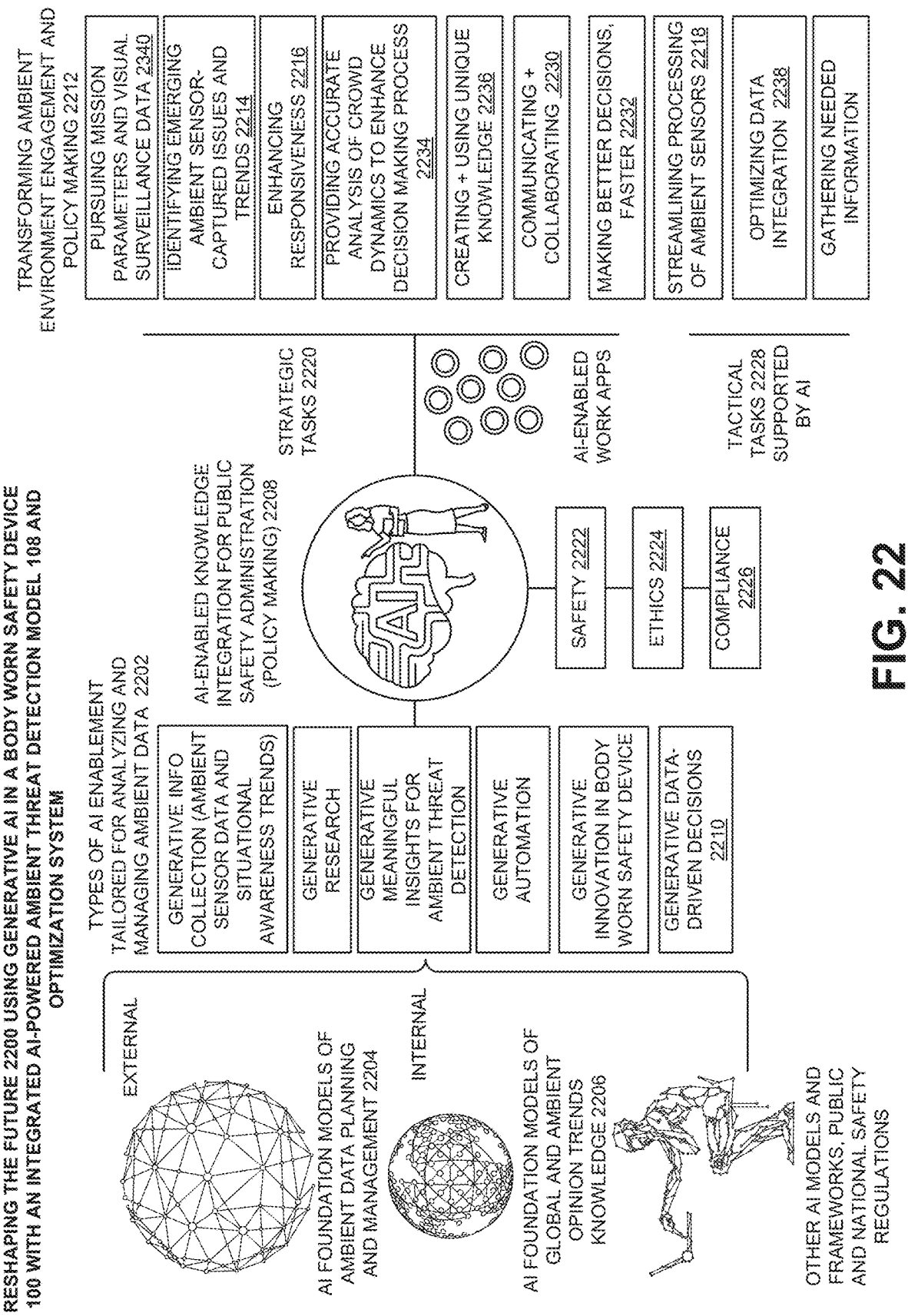
FIG. 22 illustrates the innovative application of "Generative AI in Body Worn Safety Device Management using an Integrated Threat Detection Model," as conceptualized in one embodiment of the GovGPT™ body worn safety device of FIG. 1, according to one embodiment.

CoT it or ToT it. GoT it: These are frameworks for guiding the reasoning process of language models, either through a Chain of Thought, Tree of Thought, or Graph of Thought, allowing for non-linear and interconnected reasoning. In GovGPT™ tactical gear 104, CoT, ToT, GoT frameworks can guide the AI's reasoning process as it considers complex opinion patterns, ensuring it can explore multiple outcomes and provide well-reasoned, data-driven insights FIG. 22 illustrates the innovative application of "Generative AI in Body Worn Safety Device 100 Management using an Integrated Threat Detection Model 108," as conceptualized in one embodiment of the GovGPT™ tactical gear 104 system. It highlights how artificial intelligence, particularly generative AI, can revolutionize the way ambient data are processed, analyzed, and utilized in governmental, military, law enforcement, fire and civic uses, according to one embodiment. The image is divided into three sections:

Types of AI Enablement Tailored for Analyzing and Managing Ambient Data 2202: This section showcases generative AI foundation models specifically tailored for analyzing and managing ambient data 2204. It emphasizes the system's capability to understand global and ambient opinion trends 2206 and to extract meaningful insights from a vast array of ambient sensors. This process may particularly involve generative info collection such as ambient sensor data and situational awareness trends, generative research and meaningful insights for ambient threat detection, generative automation and innovation in body worn safety device 100, according to one embodiment.

AI-Enabled Knowledge Integration for Public Safety Administration 2208: This part emphasizes the AI's capabilities in transforming the way government officials and agencies engage with their constituents. It highlights how the AI aids in making data-driven decisions 2210, ensuring public safety 2222, ethics 2224, and compliance 2226 within the realms of public safety administration and policy-making.

Transforming Ambient Environment Engagement and Policy-making 2212: The final section is divided into strategic tasks 2220 such as identifying emerging ambient sensor-captured concerns and trends 2214 that can influence policy decisions, and tactical tasks 2228 like streamlining the processing of ambient sensors 2218 and enhancing the responsiveness 2216 of military, law enforcement, and first responder bodies, according to one embodiment. The visualization serves as a powerful explanation of GovGPT™ tactical gear's role in pioneering the future of ambient body worn safety device 100 computing, according to one embodiment.

FIG. 22 demonstrates the transformative impact of AI on governance, particularly through the analysis of ambient signals, according to one embodiment. Strategically, the AI identifies emerging issues and trends 2214 in ambient signals, informing policy-makers (e.g., communicating+collaborating 2230) about the pressing concerns of their constituents. This insight can be crucial in addressing societal challenges and improving community relations. It also enhances the decision-making process (e.g., making better decisions faster 2232) by providing accurate analysis of crowd dynamics to enhance the decision making process 2234, using unique knowledge 2236, optimizing data integration 2238, and pursuing mission parameters and visual surveillance data 2240, according to one embodiment. This integration of AI in public administration represents a significant advancement in enhancing democratic engagement, making the public consultation process more accessible and impactful, according to one embodiment.

Figure 23:
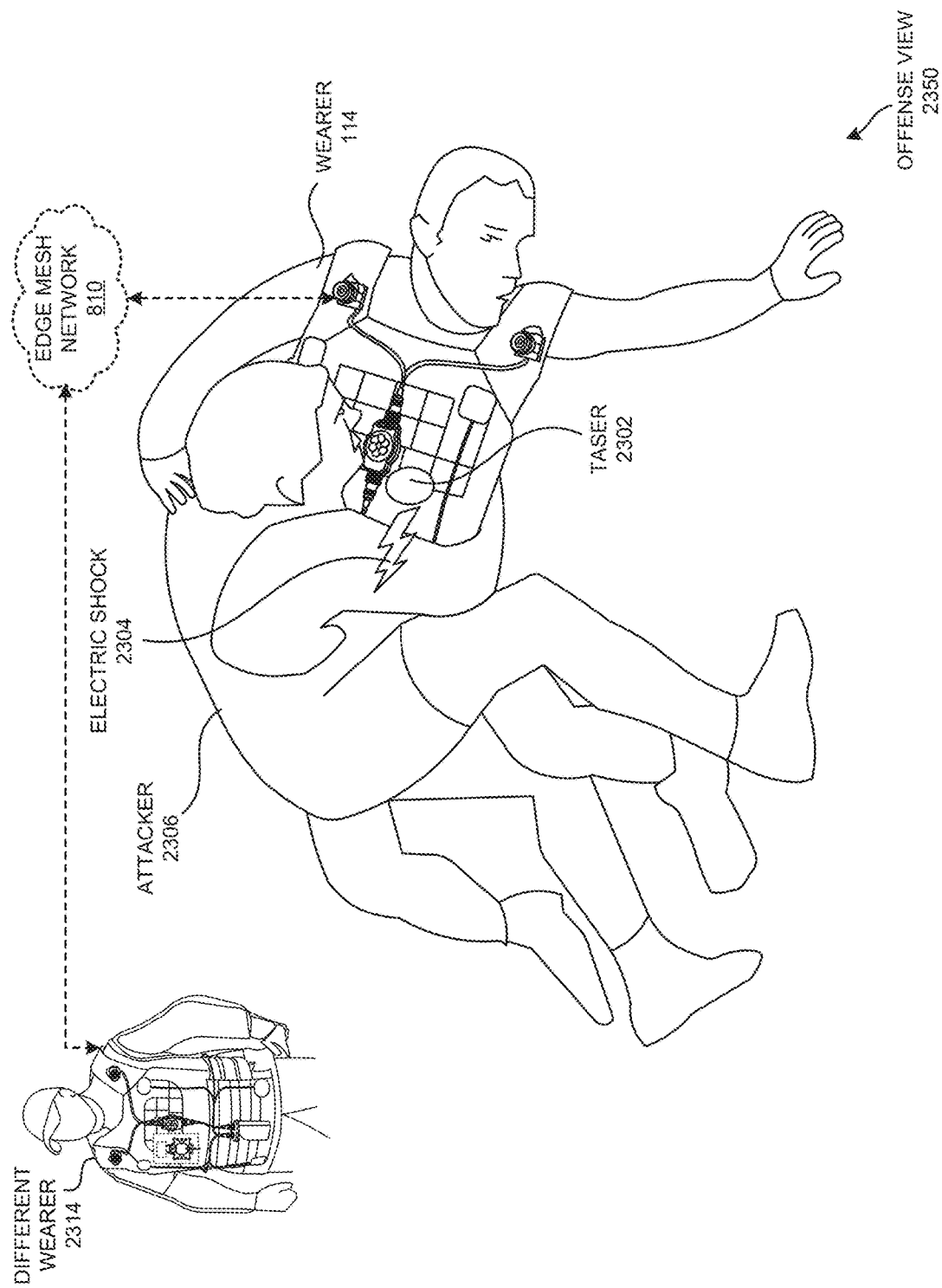
FIG. 23 is an offense view of a taser integrated into the tactical gear to automatically deliver an electric shock to an attacker who is physically wrestling with the wearer when the artificial intelligence based threat detection model detects a physical assault, according to one embodiment.

FIG. 23 is an offense view 2350 of a taser 2302 integrated into the tactical gear 104 to automatically deliver an electric shock 2304 on an attacker 2306 who is physically wrestling with the wearer 114 when the artificial intelligence based threat detection model 108 detects a physical assault 2308, according to one embodiment. The taser 2302 may be an electroshock weapon that uses electrical current to disrupt voluntary control of muscles. The electric shock 2304 may be a sudden discharge of electricity that passes through the body, potentially causing pain, muscle contractions, and involuntary movements. In this case, the threat detection model 108 may be designed to recognize physical assaults or attacks against the wearer 114 of the tactical gear 104. In this embodiment, the primary function of this integrated setup is to automatically administer an electric shock 2304 to an assailant 2306 when the wearer 114 of the tactical gear 104 is physically engaged in a struggle with them. This automatic response is triggered by an artificial intelligence-based threat detection model 108. Specifically, when the AI-based threat detection model 108 identifies a physical assault 2308, it activates the mechanism within the tactical gear 104, which deploys the taser 2302. This deployment delivers an electric shock 2304 to the attacker 2306, potentially incapacitating them and providing a momentary advantage to the wearer 114. The different wearer 2314 may be notified when the wearer 114 is being attacked, as described in FIG. 23 through a network (e.g., the edge mesh network 810 of FIG. 8, or the internet), according to one embodiment.

The integration of the taser 2302 into the tactical gear 104 may enhance the wearer 114's ability to defend themselves in close combat situations. By automating the response to physical assault, the system can improve the wearer's safety and potentially deter aggressors from initiating attacks, according to one embodiment. This embodiment showcases the convergence of advanced technologies, such as AI-based threat detection and electroshock weaponry, to enhance personal protection and security measures of the tactical gear 104, according to one embodiment.

A body-worn taser 2302 integrated into a tactical gear 104 may activate in response to a detected physical attack can work through a combination of sensors, data processing, and actuation mechanisms. Here is a detailed description of how such a system might operate:

A visual sensor 102 (or camera) may be equipped with advanced detection algorithms mounted on the tactical gear 104. This visual sensor 102 may be responsible for real-time monitoring of the wearer 114's surroundings. It may employ machine learning models trained to recognize aggressive postures, sudden movements, or specific threat indicators. The system may use skin detection technology to distinguish between an inanimate object and a human, according to one embodiment. This can be part of the visual sensor 104's capabilities, using color, texture, and pattern recognition to identify human skin according to one embodiment.

Upon detecting a potential threat, the system's modular compute assembly 324 can analyze the data to determine the likelihood of a physical attack. This decision-making process may consider the speed, trajectory, and/or the nature of the object or attacker approaching the wearer 114. If the system identifies a high probability of a physical attack, and specifically recognizes skin within a predetermined proximity to the wearer 114, it can move to the next phase of defense activation.

Before delivering a shock, the system might issue a warning (audible, visual, or both) intended to deter the assailant such as the attacker 2306. If the threat persists, the system may activate the taser 2302. This may involve extending electrodes from the tactical gear 104 towards the direction of the assailant's skin, maintaining safety protocols to minimize harm. The taser 2302 may deliver a controlled, non-lethal electrical shock designed to incapacitate the assailant temporarily. The shock's intensity, duration, and pattern may be carefully calibrated to ensure non-lethality while effectively neutralizing the threat.

The outermost part of the tactical gear 104, may be designed to be both durable and functional. It may serve as the first line of defense against external elements. Sandwiched between the fabric and the lining, this layer may house a network of soft, pressure-activated sensors, according to the embodiment of FIG. 23. The taser 2302 may in fact be soft sensors which are highly sensitive to changes in force or pressure applied to any part of the tactical gear 104. The lining may include an innermost layer that ensures wearer 114 comfort. It also may protect the embedded sensors from direct contact with the body, preventing any discomfort from the sensors' activation. The soft sensors embedded between the fabric and lining may be crucial for detecting assaultive or unusual forces, such as grabbing, attacking, or pinning actions against the wearer. These sensors may be pressure-activated, meaning they respond to specific thresholds of force. Once these thresholds are exceeded, the sensors may trigger a signal, indicating potential danger.

To prevent accidental activation, the system may include multiple safety protocols or a manual override that the wearer can engage. One embodiment may have a pressure sensor and a touch sensor to determine and provide data on how much pressure is applied to a fabric, according to one embodiment. In embodiment the tactical gear 104 can deliver a non-lethal 3000-volt shock to anybody who touches the wearer 114. The main goal may be to separate two people from each other so that the wearer 114 can escape. The tactical gear 104 may be water repellant and antibacterial, and a fabrication technique may be a sew free method of stitching. Given the potential for harm, the system may need to follow local laws and ethical standards regarding self-defense and non-lethal weapons. After activation, the system can automatically alert law enforcement or emergency services, providing them with the location and a brief overview of the incident. The tactical gear 104 might also have a recording feature, capturing video footage for evidence purposes. This concept can require advanced sensor technology, machine learning algorithms for threat detection, and safe, effective taser integration. Ethical, legal, and safety considerations can be paramount, necessitating comprehensive testing and regulatory approval before such a device should be deployed.

Figure 24:
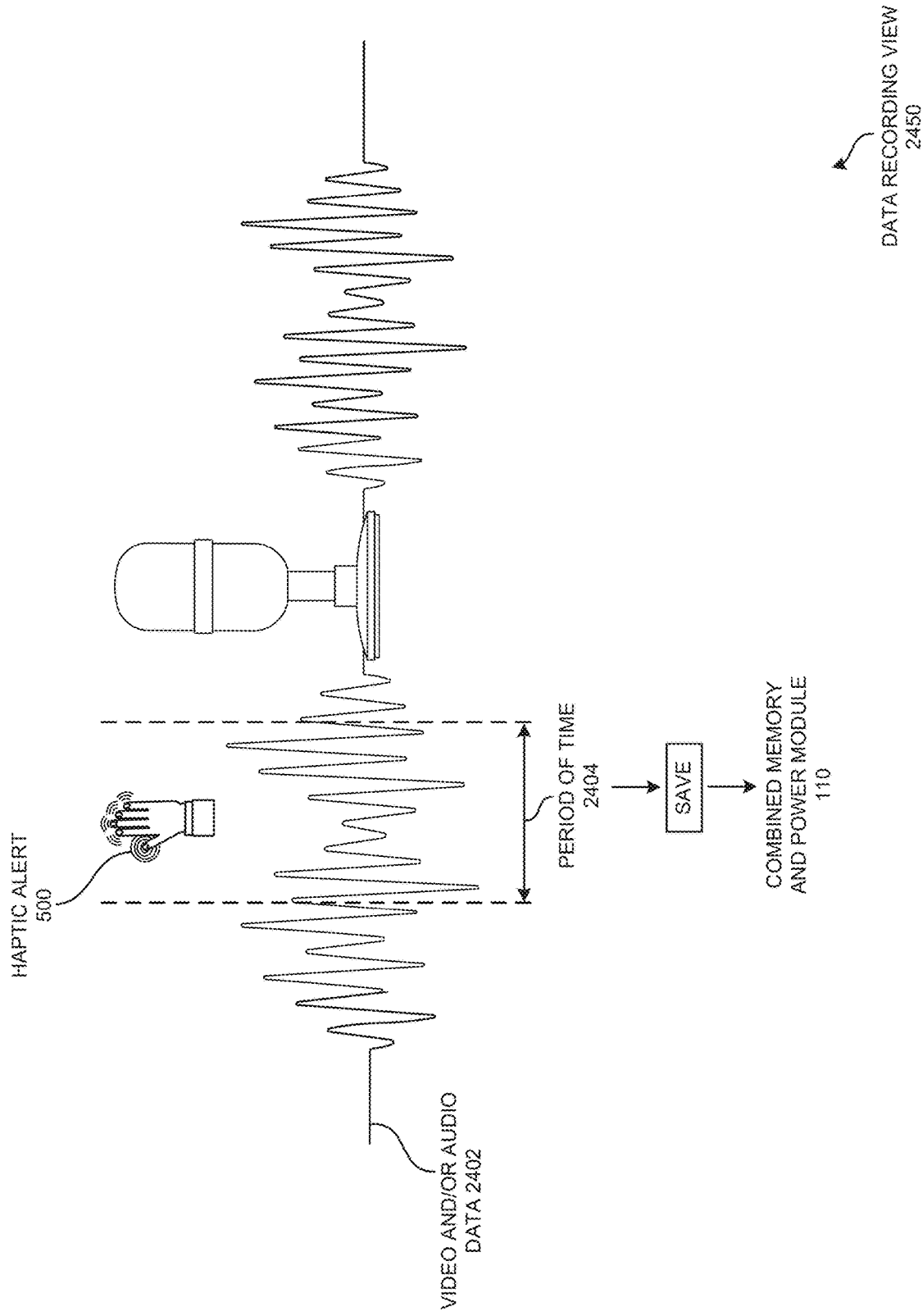
FIG. 24 is a data recording view that demonstrates that the combined memory and power module saves video and audio data associated with a period of time prior to the activation of a haptic feedback device from a visual sensor closest to a haptic feedback device that is activated using of the body safety device of FIG. 1, according to one embodiment.

FIG. 24 is a data recording view 2450 that demonstrates that the combined memory and power module 110 saves video and/or audio data 2402 associated with a period of time 2404 prior to the activation of a haptic feedback device 210 from a visual sensor 102 closest to a haptic feedback device 210 that is activated, according to one embodiment. Video and/or audio data 2402 may be visual and/or auditory information captured by sensors within the system. It may include video footage from cameras and audio recordings from microphones. This data may be associated with a specific time period. The period of time 2404 may be a duration or interval during which data is recorded before, during, and/or shortly after the activation of a specific sensor or event. The body worn safety device 100 may be designed to record footage through the combined memory and power module 110, which may be a detachable battery 314 combined with a solid-state storage module. This module 110 may be removed from the tactical gear 104 while leaving the sensor array and haptic feedback device 210 intact. Users can easily swap these battery/memory modules, allowing for uninterrupted recording. By having multiple modules, users can ensure continuous recording throughout the day, according to this embodiment.

The recorded data may be stored locally on the device. When users dock the combined memory and power module 110, the data may be uploaded to a server. Three types of data may be uploaded: a log file, an audio file, and video footage. The body worn safety device 100 may capture footage continuously, but may specifically save a segment of data before and after a triggered event, such as a haptic alert 500. For example, it may save 60 seconds of footage before the haptic alert 500, during the haptic alert 500 activation of the haptic feedback device 106, and/or 60 seconds after. This approach may minimize storage requirements while ensuring critical moments are captured and privacy to the wearer 114. For example, it reduces the risk of irrelevant footage being stored, such as when the wearer 114 takes a break, according to one embodiment.

In addition to saving video footage, the body worn safety device 100 may also stores a descriptive AI log file detailing the events leading up to the triggered response. This log file may provide valuable context for understanding why the alert was activated. Furthermore, this embodiment may permit live streaming from one or more visual sensors on the tactical gear 104. The live streaming functionality may be implemented using a secure streaming protocol to ensure the privacy and integrity of the transmitted data. Encryption techniques may be employed to protect the video feed from unauthorized access or interception, according to one embodiment.

In addition, it will be appreciated that the various operations, processes and methods disclosed herein may be embodied in a non-transitory machine-readable medium and/or a machine-accessible medium compatible with a data processing system. Accordingly, the specification and drawings are to be regarded in an illustrative rather than a restrictive sense.

Many embodiments have been described. Nevertheless, it will be understood that various modifications may be made without departing from the spirit and scope of the claimed invention. For example, the GovGPT™ Body-worn safety device may be the GovGPT™ tactical gear in any form including helmet form). Also, embodiments described for one use case, such as for law enforcement, may apply to any of the other use cases described herein in any form. In addition, the logic flows depicted in the Figures do not require the particular order shown, or sequential order, to achieve desirable results. In addition, other steps may be provided, or steps may be eliminated, from the described flows. Other components may be added or removed from the described systems. Accordingly, other embodiments are within the scope of the following claims.

It may be appreciated that the various systems, methods, and apparatus disclosed herein may be embodied in a machine-readable medium and/or a machine-accessible medium compatible with a data processing system (e.g., a computer system), and/or may be performed in any order.

The structures and modules in the Figures may be shown as distinct and communicating with only a few specific structures and not others. The structures may be merged with each other, may perform overlapping functions, and may communicate with other structures not shown to be connected in the Figures. Accordingly, the specification and/or drawings may be regarded in an illustrative rather than a restrictive sense.

In one embodiment, specialized processors are used for vision processing and sensors. For example, advanced AI vision processors designed by Ubicept (https://www.ubicept.com/). Ubicept's technology, which enhances computer vision by counting individual photons, can significantly enhance the GovGPT DragonFly™'s capabilities, according to one embodiment. By integrating Ubicept's advanced imaging technology, the GovGPT DragonFly™ can offer unparalleled visual clarity in all lighting conditions, including extreme low light or high-contrast environments, according to one embodiment. This can allow for more accurate threat detection and environmental analysis, according to one embodiment. The ability to capture sharp images in high-speed motion can improve the system's responsiveness in dynamic scenarios, according to one embodiment. Additionally, the technology's potential to see around corners can provide a strategic advantage in complex, urban combat zones or in reconnaissance missions, according to one embodiment. This integration can make the GovGPT DragonFly™ an even more powerful tool for military and law enforcement personnel, offering enhanced situational awareness and operational effectiveness, according to one embodiment.

In another embodiment, Ambarella's Oculii radar technology (https://www.oculii.com/), combined with 4D imaging radar (e.g., single-chip Software-Defined Vision Sensor (SDVS), can significantly enhance the GovGPT Dragon-Fly™. It can offer advanced angular resolution, LIDAR-like point cloud density, and long-range radar sensing, according to one embodiment. By dynamically adapting radar waves and reducing data size, it enables high-performance imaging radar systems, according to one embodiment. This technology can improve TactiGuard's detection capabilities in various environmental conditions, particularly in rain, snow, and fog, where visual systems might fail, according to one embodiment. The integration can lead to a more comprehensive sensing suite, combining camera, radar, and AI processing for a complete autonomous mobility solution, according to one embodiment. The SVDS with integrated neuromorphic sensing and processing can deliver real time vision intelligence with privacy at source to the body worn safety device to detect an obstacle and/or an ambient threat in a path of the wearer during low light conditions and may trigger the haptic feedback device 106 when the the obstacle and/or the ambient threat is detected.

For example, for training the GovGPT DragonFly™, the NVIDIA A100 Tensor Core GPU (https://www.nvidia.com/en-us/data-center/a100/) can be an optimal choice, according to one embodiment at the time of this patent application. It should be understood that future generations of AI specific chips might be preferred in years ahead. At the current time of this writing, the A100 offers significant acceleration for deep learning and machine learning tasks, making it ideal for processing the complex algorithms and vast data sets involved in training the GovGPT DragonFly™, according to one embodiment. The A100's advanced architecture provides enhanced computational power, enabling faster training times and more efficient handling of large neural networks, which are crucial for the sophisticated AI capabilities required in the GovGPT DragonFly™, according to one embodiment.

Using NVIDIA®'s A100 Tensor Core GPU to train the GovGPT DragonFly™ involves leveraging its powerful computational abilities for handling deep learning tasks, according to one embodiment. The A100's architecture (and future generations of similar or better computational chips) is well-suited for processing large and complex neural networks, which are fundamental in the AI algorithms of TactiGuard™. Its high throughput and efficient handling of AI workloads can significantly reduce training times, enabling rapid iteration and refinement of models, according to one embodiment. This is particularly useful in developing the sophisticated pattern recognition, threat detection, and decision-making capabilities of the TactiGuard™ system, according to one embodiment. Through its advanced AI acceleration capabilities, the A100 can effectively manage the voluminous and diverse datasets that GovGPT DragonFly™ can require for comprehensive training at this time, according to one embodiment.

To train the GovGPT DragonFly™ using NVIDIA's A100 Tensor Core GPU, GovGPT™ intends to follow these steps, according to one embodiment:

Data Collection: Gather extensive datasets that include various scenarios TactiGuard™ might encounter, like different environmental conditions, human behaviors, and potential threats, according to one embodiment.

Data Preprocessing: Clean and organize the data, ensuring it's in a format suitable for training AI models, according to one embodiment. This might include labeling images, segmenting video sequences, or categorizing different types of sensory inputs, according to one embodiment.

Model Selection: Choose appropriate machine learning models for tasks such as image recognition, threat detection, or decision-making, according to one embodiment.

Model Training: Use the A100 GPU to train the models on the collected data, according to one embodiment. This involves feeding the data into the models and using algorithms to adjust the model parameters for accurate predictions or classifications, according to one embodiment.

Evaluation and Testing: Regularly evaluate the models against a set of test data to check their accuracy and reliability, according to one embodiment. Make adjustments to the model as needed based on performance, according to one embodiment.

Optimization: Fine-tune the models for optimal performance, according to one embodiment. This includes adjusting hyperparameters and potentially retraining the models with additional or refined data, according to one embodiment.

Integration: Once the models are adequately trained and optimized, integrate them into the TactiGuard™ system's software framework, according to one embodiment.

Real-World Testing: Deploy the system in controlled real-world scenarios to test its effectiveness and make any necessary adjustments based on its performance, according to one embodiment.

Continuous Learning: Implement a mechanism for continuous learning, allowing the system to adapt and improve over time based on new data and experiences, according to one embodiment. Throughout these steps, the power of the A100 GPU can be utilized to handle the heavy computational load, especially during the training and optimization phases, ensuring efficient and effective model development, according to one embodiment.

Apart from NVIDIA's A100 GPU framework, emerging chipsets offer enhanced computational capabilities. For example, integrating SambaNova® technology (https://sambanova.ai/) into the GovGPT DragonFly™ can offer significant benefits. At the time of this writing, SambaNova® develops both computer chips and machine learning software, intended for enterprise customers to train their own GPTs and other AI models on proprietary data; the company is partnered with Accenture and clients include Argonne National Labs. In a recent interview, director Vijay Tatkar claimed SambaNova has "trained a large language model six times faster than an Nvidia A100' . . . enabling companies to stand up their own ChatGPT equivalent in a matter of days." (https://visionfund.com/insights/dancing-with-ai)

Training based on SambaNova® SN40L may involve a multi-step process, according to one embodiment:

Hardware Installation: Embed SambaNova's SN40L chips within TactiGuard's processing units, ensuring compatibility and efficient communication between components, according to one embodiment.

Software Integration: Adapt TactiGuard's software to leverage SambaNova's machine learning capabilities, optimizing algorithms for enhanced performance, according to one embodiment.

Model Training: Utilize SambaNova's powerful processing to train complex AI models for TactiGuard™, particularly in areas like pattern recognition and threat analysis, according to one embodiment.

Testing and Validation: Rigorously test the integrated system to ensure reliability and accuracy in various operational scenarios, according to one embodiment.

Deployment and Updates: Deploy the enhanced GovGPT DragonFly™ and establish a protocol for regular updates to leverage ongoing advancements from SambaNova, according to one embodiment.

Integrating SambaNova's SN40L and SambaNova® chips into the GovGPT DragonFly™ can substantially enhance its AI capabilities, according to one embodiment. With the SN40L's ability to handle a 5 trillion parameter model, significantly more than the GPT-4's 1.76 trillion parameters, the TactiGuard™ can process and analyze more complex data at an unprecedented scale, according to one embodiment. This can enable more advanced pattern recognition, faster decision-making, and highly efficient real-time analysis in various operational environments, according to one embodiment. Additionally, the claim that SambaNova's technology can train large models six times faster than an Nvidia A100 suggests that the TactiGuard's AI models can be developed and updated much more rapidly, keeping the system at the forefront of AI advancements in security and defense, according to one embodiment.

Although the present embodiments have been described with reference to specific example embodiments, it will be evident that various modifications and changes may be made to each of the embodiments in FIGS. 1-24 without departing from the broader spirit and scope of the various embodiments. Features in one embodiment and use case may be applicable to other use cases as described, and one with skill in the art will appreciate this and those interchanges are incorporated as embodiments of each use case—fire, military, police, civilian, journalism, EMT etc. For example, the various devices and modules described herein may be enabled and operated using hardware circuitry (e.g., GPUs, CMOS based logic circuitry), firmware, software or any combination of hardware, firmware, and software (e.g., embodied in a non-transitory machine-readable medium). For example, the various electrical structures and methods may be embodied using transistors, logic gates, and electrical circuits (e.g., graphics processing units (GPUs), application-specific integrated (ASIC) circuitry and/or Digital Signal Processor (DSP) circuitry).

The invention claimed is:

1. A body worn safety device, comprising:
   a visual sensor integrated into a tactical gear; and
   a haptic feedback device integrated in the tactical gear,
      wherein the haptic feedback device to vibrate when the visual sensor detects an ambient threat to a wearer of the tactical gear, and at least one of:
         an intensity of vibration of the haptic feedback device is dependent on a proximity of the ambient threat to the wearer, and
         a pattern of vibration of the haptic feedback device is dependent on a type of threat.

2. The body worn safety device of claim 1 wherein the body worn safety device to detect the ambient threat using an artificial intelligence based threat detection model.

3. The body worn safety device of claim 2:
   wherein the visual sensor is part of an array of visual sensors around a torso of the wearer, and
   wherein the artificial intelligence based threat detection model to detect and analyze human emotion of an individual in an ambient area to the wearer using computer vision and auditory sensing to detect the presence or absence of the ambient threat.

4. The body worn safety device of claim 1 wherein the visual sensor is a front-facing visual sensor embedded in both shoulder areas of the tactical gear such that the wearer is able to sense the ambient threat through the haptic feedback device-when the ambient threat approaches the wearer of the tactical gear.

5. The body worn safety device of claim 1 wherein the visual sensor is embedded in a center back area of the tactical gear such that the wearer is able to sense the ambient threat through the haptic feedback device when the ambient threat approaches from behind the wearer of the tactical gear.

6. The body worn safety device of claim 1 wherein a language translator module is integrated in a center front area through which the wearer is able to bi-directionally communicate with an individual in the ambient environment using any language other than a primary language spoken by the wearer when the language translator module is activated.

7. The body worn safety device of claim 1 further comprising:
   a combined memory and power module which is removable from the tactical gear and which provides power to the visual sensor and the haptic feedback device,
      wherein the combined memory and power module includes a memory storage which auto downloads sensory data captured from the visual sensor and the haptic feedback device when the combined memory and power module is docked in a docking station, and
      wherein in the combined memory and power module to simultaneously charge multiple devices on the wearer comprising any one of a mobile phone, a body worn camera, and the visual sensor.

8. The body worn safety device of claim 1 further comprising a processing unit which is removable from the tactical gear and which provides optional processing and sensor capabilities to the body worn safety device.

9. The body worn safety device of claim 1 further comprising a user authentication means to activate the visual sensor and the haptic feedback device the wearer is an authorized user, and wherein the visual sensor also serves as a visual recording device.

10. The body worn safety device of claim 1 wherein the haptic feedback device is part of an array of haptic feedback devices to vibrate at different locations of a body of the wearer depending on a directional location of the ambient threat.

11. The body worn safety device of claim 1 wherein the visual sensor to automatically document a health condition of an injured individual in the ambient environment and communicate that information to a nearby hospital where the injured individual is to be transported.

12. The body worn safety device of claim 1:
    wherein the haptic feedback device to vibrate when a different wearer of a different body worn safety device to detect a different ambient threat in a same ambient environment of the wearer, and
    wherein the different body worn safety device is communicatively coupled with the body worn safety device through an ad-hoc edge mesh network formed between the body worn safety device and the different body worn safety device.

13. The body worn safety device of claim 1 wherein the body worn safety device is solely a real time observation device that provides early warnings to the wearer of any one of a pre-assaultive threat, an opioid addiction warning, an intoxicated state warning, and a mental health warning in an ambient environment.

14. The body worn safety device of claim 1:
    wherein the body worn safety device to vibrate when an unmanned aerial vehicle networked with the body worn safety device in an active incident area perceives an ambient threat nearby to the wearer, and
    wherein the unmanned aerial vehicle is part of an emotionally aware drone swarm which uses any one of a plurality of sensors to detect aggressive emotions in a riotous gathering.

15. The body worn safety device of claim 1 wherein the body worn safety device to vibrate when a land vehicle networked with the body worn safety device perceives an ambient threat nearby to the wearer.

16. The body worn safety device of claim 1 wherein only a subset of an array of haptic feedback devices on the body worn safety device closest to the ambient threat to vibrate based on a directionality of the ambient threat, and wherein the body worn safety device to include a global positioning system.

17. The body worn safety device of claim 1 wherein the body worn safety device to vibrate when a stationary sensory device networked with the body worn safety device perceives an ambient threat nearby to the wearer.

18. The body worn safety device of claim 1 wherein the visual sensor is embedded in a flush manner in a shoulder area of the tactical gear such that movement of a tactical rifle is not impeded by the visual sensor.

19. The body worn safety device of claim 1 wherein the body worn safety device does not permanently store real-time threat analysis.

20. The body worn safety device of claim 1 further comprising a biometric sensor of the tactical gear to measure a biometric information of the wearer,
  wherein the biometric sensor is detachable from the tactical gear and placeable on an injured person nearby to the wearer through an armband extendable from biometric sensor when it is removed from the tactical gear, and
  wherein the biometric sensor to automatically communicate the biometric information of the injured person to a hospital when removed from the tactical gear and placed on an arm of the injured person, when the injured person is en route to the hospital.

21. The body worn safety device of claim 1 wherein the body worn safety device to detect at least one of an obstacle and the ambient threat in a path of the wearer during low light conditions and to trigger the haptic feedback device when the at least one of the obstacle and the ambient threat is detected.

22. The body worn safety device of claim 1 further comprising a spherical disc wirelessly coupled with the body worn safety device that is carryable by the wearer and is throwable by the wearer, wherein the spherical disc to automatically unfurl when it is thrown by the wearer onto a level surface, such that a camera of the spherical disc is perpendicularly manifested and actively recording when in the unfurled state, and wherein the haptic feedback device on the body worn safety device to vibrate when ambient threat is visible to the camera of the spherical disc in the unfurled state.

23. The body worn safety device of claim 1 wherein a retainer placed in a mouth of the wearer to at least one of bookmark a geospatial location based on an action in the mouth of wearer, and request help to arrive at the geospatial location.

24. The body worn safety device of claim 1 wherein the body worn safety device communicates without electronic signature through a non-radiative, human-body-centered communication network.

25. The body worn safety device of claim 1 further comprising a taser integrated into the tactical gear to automatically deliver an electric shock to an attacker who is physically wrestling with the wearer when the artificial intelligence based threat detection model detects a physical assault.

26. The body worn safety device of claim 1 wherein an audiovisual data of the visual sensor closest to the haptic feedback device is automatically stored in a combined memory and power module for at least one of a short period of time prior to the vibration of the haptic feedback device, during the vibration of the haptic feedback device, and another short period of time after the vibration of the haptic feedback device stops vibrating.

27. The body worn safety device of claim 1 wherein the visual sensor is a thermal imaging sensor that detects heat signatures emitted by objects and converts them into visual data.

28. A body worn safety device, comprising:
  a visual sensor integrated into a tactical gear; and
  a haptic feedback device integrated in the tactical gear,
    wherein the haptic feedback device to vibrate when the visual sensor detects an ambient threat to a wearer of the tactical gear, and
    wherein the body worn safety device to detect at least one of an obstacle and the ambient threat in a path of the wearer during low light conditions and to trigger the haptic feedback device when the at least one of the obstacle and the ambient threat is detected.

29. A body worn safety device, comprising:
  a visual sensor integrated into a tactical gear; and
  a haptic feedback device integrated in the tactical gear,
    wherein the haptic feedback device to vibrate when the visual sensor detects an ambient threat to a wearer of the tactical gear, and
    wherein the body worn safety device is a real time observation device that provides early warnings to the wearer of any one of a pre-assaultive threat, an opioid addiction warning, an intoxicated state warning, and a mental health warning in an ambient environment.

30. A body worn safety device, comprising:
  a visual sensor integrated into a tactical gear; and
  a haptic feedback device integrated in the tactical gear,
    wherein the haptic feedback device to vibrate when the visual sensor detects an ambient threat to a wearer of the tactical gear, and at least one of:
      an intensity of vibration of the haptic feedback device is dependent on a proximity of the ambient threat to the wearer, and
      a pattern of vibration of the haptic feedback device is dependent on a type of threat, and
    wherein the body worn safety device to vibrate when an unmanned aerial vehicle networked with the body worn safety device in an active incident area perceives an ambient threat nearby to the wearer.

\* \* \* \* \*